United States Patent [19]
Bestwick et al.

[11] Patent Number: 5,859,330
[45] Date of Patent: *Jan. 12, 1999

[54] REGULATED EXPRESSION OF HETEROLOGOUS GENES IN PLANTS AND TRANSGENIC FRUIT WITH A MODIFIED RIPENING PHENOTYPE

[75] Inventors: Richard Keith Bestwick, Portland; Adolph J. Ferro, Lake Oswego, both of Oreg.

[73] Assignee: Epitope, Inc., Beaverton, Oreg.

[*] Notice: The term of this patent shall not extend beyond the expiration date of Pat. No. 5,723,746.

[21] Appl. No.: 331,355

[22] Filed: Oct. 27, 1994

Related U.S. Application Data

[63] Continuation-in-part of Ser. No. 261,677, Jun. 17, 1994, Ser. No. 46,583, Apr. 9, 1993, and Ser. No. 255,833, Jun. 8, 1994, Pat. No. 5,416,250, which is a continuation of Ser. No. 613,858, Dec. 12, 1990, abandoned, which is a continuation-in-part of Ser. No. 448,095, Dec. 12, 1989, abandoned.

[51] Int. Cl.$^6$ .............................. A01H 5/00; A01H 5/08; C12N 15/82
[52] U.S. Cl. .................................. 800/205; 800/DIG. 64; 800/DIG. 65; 435/69.1; 435/172.3; 435/320.1; 435/419; 536/23.1; 536/24.1; 536/23.6; 536/23.7
[58] Field of Search ........................... 800/205, DIG. 64, 800/65; 435/69.1, 172.3, 240.4, 320.1, 419; 536/23.1, 24.1, 23.6, 23.7

[56] References Cited

U.S. PATENT DOCUMENTS 5,416,250  5/1995  Ferro et al. .............................. 800/205

FOREIGN PATENT DOCUMENTS

WO 91/09112   6/1991   WIPO .
WO 92/12249   7/1992   WIPO .
WO A 94 24294  10/1994   WIPO .

OTHER PUBLICATIONS

Bestwick, R.K., et al., "Decreased Ethylene Synthesis and Altered Fruit Ripening in Transgenic Tomatoes Expressing S-Adenosylmethionine Hydrolase," *HortScience* 29:474, abstract No. 306 (1994).

Bestwick, R.K., et al., Reduced Ethylene Synthesis and Supended Fruit Ripening in Transgenic Tomatoes Expressing S-Adenosylmethionine Hydrolase, *J. Cell. Biochem. Suppl.* 0(16 part a):98 abstract No. X1-208 (1994).

Deikman, J., et al., Organization of Ripening and Ethylene Regulatory Regions in a Fruit-Specific Promoter from Tomato (*Lycopersicon esculentum*) *Plant Physiol.* 100:2013-2017 (1992).

Langhoff, D., et al., "Effect of S-Adenosylmethionine Hydrolase Expression on Ethylene Biosynthesis in Transgenic Tomatoes," *J. Chem. Biochem. Suppl.* 0 (16 part F), abstract No. Y307 (1992).

Lincoln, J.E., et al., "Regulation of Gene Expression by Ethylene During *Lycopersicon esculentum* (Tomato) Fruit Development," *Proc. Natl. Acad. Sci. USA* 84:2793-2797 (1987).

Lincoln, J.E., and Fischer, R.L., "Regulation of Gene Expression by Ethylene in Wild-Type and vin Tomato (*Lycopersicon esculentum*) Fruit," *Plant Physiol.* 88:370-374 (1988).

Lincoln, J.E., and Fischer, R.L., "Diverse Mechanisms for the Regulation of Ethylene-Inducible Gene Expression," *Mol. Gen. Genet.* 212:71-75 (1988).

Mathews, H., et al., "Genetic Transformation of Red Raspberry with a Gene to Control Ethylene Biosynthesis," *HortScience* 29:445, abstract No. 180 (1994).

Montgomery, J., et al., "Identification of an Ethylene-Responsive Region in the Promoter of a Fruit-Ripening Gene," *Proc. Natl. Acad. Sci. USA* 90:5939-5943 (1993).

Lewin (1987) Science 237:70.
Benfey et al (1990) Science 250:959-966.
Smith et al (1988) Nature 334:724-726.
Hughes et al. (1987) Nucleic Acids Res 15(2) 717-729.
Klee et al. (1991) The Plant Cell 3: 1187-1193.
Cordes et al (1989) The Plant Cell 1:1025-1034.

*Primary Examiner*—Elizabeth F. McElwain
*Attorney, Agent, or Firm*—Gary R. Fabian; Susan T. Evans

[57] ABSTRACT

The present invention relates to chimeric genes having (i) a DNA sequence encoding a product that is effective to reduce ethylene biosynthesis in fruit from the plant, and (ii) a promoter whose expression is induced during fruit ripening or by ethylene synthesis by the fruit, where the DNA sequence is heterologous to the promoter and the DNA sequence is operably linked to the promoter to enable expression of the product. The invention describes vectors and transgenic plants, vegetables, flowers and fruits carrying the chimeric gene, as well as methods related thereto.

35 Claims, 37 Drawing Sheets

Fig. 11A

```
                                                                    pUC19SAM-K

XhoII
                                                            Sau3AI
                                                              NlaIV
                                                      TaqI  NdeII
                                                      SalI XbaI MboI
                                                       MnlI     CpfI
                                                  PstI HinfI    BstI
                              HindIII        SphI HincII
                              EcoVIII        NlaIII AccI MaeI BamHI
            NlaIII              AluI          |  ||| |||| ||    |
    AluI      |                  |  |          |  ||| |||| ||    |
     |        |                  |  |          |  ||| |||| ||    |
  1 ACAGCTATGACCACCATGATTACGCCAAGCTTGCATGCCTGCAGGTCGACTCTAGAGGATCC MnlI             NlaIII
             MnlI    MnlI                  HphI               |
              |        |                    |                 |
115 CTTTCCGTTCTAACCTCTGCGATGAGGTGAATATGAGCAGACACCGCCACATGGTAAGC
    laPheArgSerAsnLeuCysAspGluValAsnMETSerArgHisArgHisMETValSer MnlI
         HlnPlI
         HhaI
         CfoI DdeI                                RsaI
          ||   |                                   |
235 ATCGTGAGGCAATCTCAAGGCGCCACCAACTGAGGAAAAAACTGTTCGTGTACGCTACAAG
    yrArgGluAlaIleSerSerAlaProThrGluLuLysThrValArgValArgTyrLys
```

Fig. 11B

```
                         XmnI
                 MboII   Asp700         RsaI
NcoI               |       |              |
 |
GCCACCATGGTTTCACTAAAGAGCCTGCGAACGTCTTCTATGTACTGGTTTCCG  114
  METValPheThrLysGluProAlaAsnValPheTyrValLeuValSerA

ScrFI
                 ScrFI                              NcII
                 NcII                               MspI
                 MspI                HinfI          HpaII  MnlI
                 HpaII      NlaIV      |    HincII    ||    |
           Fnu4HI  ||         |        |      |
             |     ||         |
ACTTTACGTGCCGCCACCGGGTCTTTATGGCTCCGTTGAGTCAACCGATTTGACCGGGTGCT  234
 ThrLeuArgAlaAlaProGlyLeuTyrGlySerValGluSerThrAspLeuThrGlyCysT HinP1I
 HhaI
 Fnu4HI         MaeI
 CfoI    BbvI   AluI
  ||      |      |
GACAAGGCAGGCACTCAATGTGCACGCCTAGCTTGTAATGAGTGGGAGCAAGATTGCG  354
 AspLysAlaGlnAlaLeuAsnValAlaArgLeuAlaCysAsnGluTrpGluGlnAspCysV
```

```
      RsaI  AccI         HinfI                        RsaI              TaqI
       -     -            -                            -                 -
355 TACTGGTATACAAATCACAGACTCACACGGCTGGTCTGGTGTACGCTAAAGGTATCGAC
    alLeuValTyrLysSerGlnThrHisThrAlaGlyLeuValTyrAlaLysGlyIleAsp Fnu4HI            Fnu4HI        RsaI
           -                  -           -
474 AAGGCTGCTTCACTATTGATGAGTTCGGTCGCCGCTGGCAAGTACAATAAGTGTTAAAC
    lnGlyCysPheThrIleAspGluPheGlyArgArgTrpGlnValGln***
```

Fig. 11C

```
                                        HinPlI
                                        HhaI
         ScrFI                           CfoI
         NcII               NlaIV        BbvI    Fnu4HI
         MspI               BbvI
         HpaII MnlI                                                     474
         |  -  -               -  -       -  -    -
GGGTATAAGGCTGAACGTCTGCCGGGTAGTTCCAAGAGGTTCCTAAAGGCCACCGCTGC
GlyTyrLysAlaGluArgLeuProGlySerPheGlnGluValProLysGlyAlaProLeuG

TaqI
                                        SstI
                        RsaI             SacI
                        NlaIV            Hg1AI
                   Sau3AI   KpnI         EcoRI
                   NdeII    BanI         BanII
                   MboI     Asp718       AluI
         SfaNI NlaIII CpfI
         -     -      -  -   -   -        -       -        586
TCAAGGTCATGCACGATGCGTGGCGGATCGGGTACCGAGCTCGAATTCACTGG
```

Fig. 11D

```
Sequence Range: 1 to 2216
>EcoR1
|
|        10         20         30         40         50         60         70
GAATTCATTT TTGACATCCC TAATGATATT GTTCACGTAA TTAAGTTTTG TGGAAGTGAG AGAGTCCAAT 80         90        100        110        120        130        140
TTTGATAAGA AAAGAGTCAG AAAACGTAAT ATTTTAAAAG TCTAAATCTT TCTACAAATA AGAGCAAATT 150        160        170        180        190        200        210
TATTTATTTT TTAATCCAAT AAATATTAAT GGAGGACAAA TTCAATTCAC TTGGTTGTAA AATAAACTTA 220        230        240        250        260        270        280
AACCAATAAC CAAAGANCTA ATAAATCTGA AGTGGAATTA TTAAGGATAA TGTACATAGA CAATGAAGAA 290        300        310        320        330        340        350
ATAATAGGTT CGATGAATTA ATAATAATTA AGGATGTTAC AATCATCATG TGCCAAGTAT ATACACAATA 360        370        380        390        400        410        420
TTCTATGGGA TTTATAATTT CGTTACTTCA CTTAACTTTT GCGTAAATAA AACGAATTAT CTGATATTTT 430        440        450        460        470        480        490
ATAATAAAAC AGTTAATTAA GAACCATCAT TTTTAACAAC ATAGATATAT TATTTCTAAT AGTTTAATGA 500        510        520        530        540        550        560
TACTTTTAAA TCTTTTAAAT TTTATGTTTC TTTTAGAAAA TAAAAATTCA AAAAAATTAA ATATATTTAC 570        580        590        600        610        620        630
AAAAACTACA ATCAAACACA ACTTCATATA TTAAAAGCAA AATATATTTT GAAAATTTCA AGTGTCCTAA 640        650        660        670        680        690        700
CAAATAAGAC AAGAGGAAAA TGTACGATGA GAGACATAAA GAGAACTAAT AATTGAGGAG TCCTATAATA 710        720        730        740        750        760        770
TATAATAAAG TTTATTAGTA AACTTAATTA TTAAGGACTC CTAAAATATA TGATAGGAGA AAATGAATGG 780        790        800        810        820        830        840
TGAGAGATAT TGGAAAACTT AATAATTAAG GATNTTAAAA TATATGGTAA AAGATAGGCA AAGTATCCAT 850        860        870        880        890        900        910
TATCCCCTTT TAACTTGAAG TCTACCTAGG CGCATGTGAA AGGTTGATTT TTTGTCACGT CATATAGCTA 920        930        940        950        960        970        980
TAACGTAAAA AAAGAAAGTA AAATTTTTAA TTTTTTTTAA TATATGACAT ATTTTAAACG AAATATAGGA 990       1000       1010       1020       1030       1040       1050
CAAAATGTAA ATGAATAGTA AAGGAAACAA AGATTAATAC TTACTTTGTA AGAATTTAAG ATAAATTTAA >Xbal              >Xbal
                       |                  |
       1060       1070 |   1080       1090       1100       1110       1120
AATTTAATAG ATCAACTTTA CGTCTAGAAA GACCCATATC TAGAAGGAAT TCACGAAAT CGGCCCTTAT 1130       1140       1150       1160       1170       1180       1190
TCAAAAATAA CTTTTAAATA ATGAATTTTA AATTTAAGA AATAATATCC AATGAATAAA TGACATGTAG
```

Fig. 13A

```
         1200        1210       1220       1230       1240       1250       1260
CATTTTACCT AAATATTTCA ACTATTTTAA TCCAATATTA ATTTGTTTTA TTCCCAACAA TAGAAAGTCT 1270        1280       1290       1300       1310    |  1320       1330
TGTGCAGACA TTTAATCTGA CTTTTCCAGT ACTAAATATT AATTTTCTGA AGATTTTCGG GTTTAGTCCA 1340        1350       1360       1370       1380       1390       1400
CAAGTTTTAG TGAGAAGTTT TGCTCAAAAT TTTAGGTGAG AAGGTTTGAT ATTTATCTTT TGTTAAATTA 1410        1420       1430       1440       1450       1460       1470
ATTTATCTAG GTGACTATTA TTTATTTAAG TAGAAATTCA TATCATTACT TTTGCCAACT TGTAGTCATA 1480        1490       1500       1510       1520       1530       1540
ATAGGAGTAG GTGTATATGA TGAAGGAATA AACAAGTTCA GTGAAGTGAT TAAAATAAAA TATAATTTAG 1550        1560       1570       1580       1590       1600       1610
GTGTACATCA AATAAAAACC TTAAAGTTTA GAAAGGCACC GAATAATTTT GCATAGAAGA TATTAGTAAA 1620        1630       1640       1650       1660       1670       1680
TTTATAAAAA TAAAAGAAAT GTAGTTGTCA AGTTGTCTTC TTTTTTTTGG ATAAAAATAG CAGTTGGCTT 1690        1700       1710       1720       1730       1740       1750
ATGTCATTCT TTTACAACCT CCATGCCACT TGTCCAATTG TTGACACTTA ACTAATTAGT TTGATTCATG 1760        1770       1780       1790       1800       1810       1820
TATGAATACT AAATAATTTT TTAGGACTGA CTCAAATATT TTTATATTAT CATAGTAATA TTTATCTAAT 1830        1840       1850       1860       1870       1880       1890
TTTTAGGACC ACTTATTACT AAATAATAAA TTAACTACTA CTATATTATT GTTGTGAAAC AACAACGTTT 1900        1910       1920       1930       1940       1950       1960
TGGTTGTTAT GATGAAACGT ACACTATATC AGTATGAAAA ATTCAAAACG ATTAGTATAA ATTATATTGA 1970        1980       1990       2000       2010       2020       2030
AAATTTGATA TTTTTCTATT CTTAATCAGA CGTATTGGGT TTCATATTTT AAAAAGGGAC TAAACTTAGA 2040        2050       2060       2070       2080       2090       2100
AGAGAAGTTT GTTTGAAACT ACTTTTGTCT CTTTCTTGTT CCCATTCTC TCTTAGATTT CAAAAAGTGA
|
         2110        2120       2130       2140       2150       2160  |    2170
           *           *          *          *          *          *  |      *
ACTACTTTAT CTCTTTCTTT GTTCACATTT TATTTTATTC TATTATAAAT ATGGCATCCT CATATTGAGA

>Xmn1                                  >NcoI
           |                                      >E8_Start_codon
           |           |          |               |   |
         2180        | 2190       | 2200          2210 |
           *         |   *        |   *            |* |
TTTTAGAAA  TTATTCTAAT CATTCACAGT  GCAAAAGACC ATGGAA
```

Fig. 13B

Sequence Range: 1 to 2713

>Hind3

```
          10         20         30         40         50         60
           *          *          *          *          *          *
    AAGCTTAATT GAGATGATTA GCCCAGACCC AGCAGGATTA GGCTTAATGG TGGTCCATTT
```

>hard_to_read  >hard_to_read  >hard_to_read

```
          70         80         90        100        110        120
           *          *          *          *          *          *
    GAGAAAAAGA TTAAAAATGA TGTCATAAAA AAACNTGGTC GBCAGGATTC NAACCTGCGC 130        140        150        160        170        180
           *          *          *          *          *          *
    GGGCAAAGCC ACATGATTTC TAGTCATGCC CGATAACCAC TCCGGCACGA CCACAATGAT 190        200        210        220        230        240
           *          *          *          *          *          *
    GCTACAATTG CTTTGTTGTA ATCATTAACT TATGGTTGAG TTTGATGCTG ATTAATACTA 250        260        270        280        290        300
           *          *          *          *          *          *
    TTATGTTTCC ATTAACTACT TTTGAAGTAT ACAAAATTAC GAATTTATAA CCAAATTTGA 310        320        330        340        350        360
           *          *          *          *          *          *
    GGTATAATAT GCGAGAGCTA CCTAAATTTT TCTTACTTAA TTTTAAAGTA CATTCAAATT 370        380        390        400        410        420
           *          *          *          *          *          *
    CTGAATTTAT ATTGTGTATA GTCAGAAAAC AATCTACATA TTTAAACACA TAAATTTCTC 430        440        450        460        470        480
           *          *          *          *          *          *
    ACGTTTATAA TCAATTTTGT CGGTTCCTGT AATTTTTCTA AAATAAAAAG CAACCAAAAT
```

>Nco1
>Sty1

```
         490        500        510        520        530        540
           *          *          *          *          *          *
    TGTGCATCAA CTTATTACAT ACCATGGGAA ATGCAAACTT CAAAACTTAT GGACTCAAAG
```

>Ava1
>Xho1
>EcoO109I

```
         550        560        570        580        590        600
           *          *          *          *          *          *
    GGTACATATC TAAACTACAT ATTGTCAGAT TCTTCACTCT TATTTCTTGA GGGCCTCGAG
```

Fig. 15A

```
         610        620        630        640        650        660
    *     *    *     *    *     *    *     *    *     *    *     *
GCATTACCAA CCAAATCCAA AAATTGCTTT CGAATCTCAA TAAAAAGGAT AACCCCATGA

>BssH2
                                  |
         670        680        690        700        710        720
    *     *    *     *    *     *    *     *    *     *    *     *
AAAAGACGTG GACGGCAGGA TTCGAACCTG CGCGCAGAGC CCACATGATT TCTAGTCATG

>Hpa1
                                          |
         730        740        750        760        770        780
    *     *    *     *    *     *    *     *    *     *    *     *
CCCGATAACC ACTCCGGCAC GTCCACTTCA CTGTTAACGT TTACAGTAAC AAGTCACTAA 790        800        810        820        830        840
    *     *    *     *    *     *    *     *    *     *    *     *
CTACTAATCA ACATTAGCTC AGGAAATCAA AACTAGATTA TTTACATTTA CAACGACATG 850        860        870        880        890        900
    *     *    *     *    *     *    *     *    *     *    *     *
TCGTTCGAAG TAGTTGGTCT GTATCTGAGT AGCTTTGGCG GGTAGATTCA ATCGCATTTC

>TATA_site   >Predicted_transcriptional_start_site
    |              |
    |    910        920     |  930        940        950
    *     *    *     *    *|    *    *     *    *     *    *
TGCATATAAA ACTGATCCTC CCTCTATCGC CAAAGTCAAA CTGAAA ATG GCT TCC ACC
                                                 Met Ala Ser Thr>
                                                 ___RASP E4 ____>

>Xba1
                                |
      960        970        980|       990       1000
    *     *    *     *    *    |*    *     *    *     *    *     *
ACC ACC AAC AAC CCA GCT CTA GAC CCA GAT TCG GAC ACT CCG GAT AAT
Thr Thr Asn Asn Pro Ala Leu Asp Pro Asp Ser Asp Thr Pro Asp Asn>
___a___a___a___a___a____RASP E4 EXON1__a___a___a___a___a___a___>

>Xho2
                                            |
                                          >BamH1
                                            |
                                          >BstY1
                                            |
     1010       1020       1030 |      1040       1050
    *     *    *     *    *    |*    *     *    *     *
CCG GGT CAC GAG TTT GCT CAA TTC GGA TCC GGG TGC TTC TGG GGA GCC
Pro Gly His Glu Phe Ala Gln Phe Gly Ser Gly Cys Phe Trp Gly Ala>
___a___a___a___a___a____RASP E4 EXON1__a___a___a___a___a___a___>

1060       1070       1080       1090       1100
    *     *    *     *    *     *    *     *    *     *
GAG CTC AGG TTT CAG CGA GTG GCC GGT GTG GTC AAG ACC GAG GTT GGG
Glu Leu Arg Phe Gln Arg Val Ala Gly Val Val Lys Thr Glu Val Gly>
___a___a___a___a___a____RASP E4 EXON1__a___a___a___a___a___a___>
```

Fig. 15B

```
            1110        1120        1130        1140        1150
              *           *           *           *           *
    TAC TCC CAG GGC CAC GTC CAC GAT CCG AAT TAC AAA CTG GTC TGC TCC
    Tyr Ser Gln Gly His Val His Asp Pro Asn Tyr Lys Leu Val Cys Ser>
    ___a___a___a___a___a____RASP E4 EXON1__a___a___a___a___a___a___>

1160        1170        1180        1190
              *           *           *           *           *
    GGA ACT ACC AAC CAT TCG GAG GTC GTT CGG GTC CAG TTC GAC CCG CAA
    Gly Thr Thr Asn His Ser Glu Val Val Arg Val Gln Phe Asp Pro Gln>
    ___a___a___a___a___a____RASP E4 EXON1__a___a___a___a___a___a___>

1200        1210        1220        1230        1240
   *           *           *           *           *           *
 GTC TAC CCA TAC TCG GAC CTG CTT TCC GTC TTT TGG TCT CGT CAT GAT
 Val Tyr Pro Tyr Ser Asp Leu Leu Ser Val Phe Trp Ser Arg His Asp>
 ___a___a___a___a___a____RASP E4 EXON1__a___a___a___a___a___a___>

>5'_splice_site
                              |
     1250        1260        |1270        1280        1290        1300
       *           *         *|*           *           *           *
    CCA ACG ACT GTC AAT CGC CAG GTA TGGGGATTGG GGACTTCTGT TTTCATTTGA
    Pro Thr Thr Val Asn Arg Gln>
    ___a__RASP E4 EXON1_____a___>

>1_C_or_2_at_the_autorad_junction
                              |
     1310        1320        | 1330        1340        1350        1360
       *           *           *           *           *           *
    ATTTTGATGC TAAAAAATTT CTTGCTTTTT CATACTACAC AGTACACACA AAAAGTTGTG >8_or_9_T's
    |
    |1370        1380        1390        1400        1410        1420
    |*           *           *           *           *           *
    TTTTTTTTCA TTCTTTTAAA TAGTAGTTGG AAAAGTGCTC TTGGAGTTGA AGAGTACTTC >Small_sequencing_gap_of_unknown_size
                                                              |
     1430        1440        1450        1460        1470    |  1480
       *           *           *           *           *     |*   *
    AGTATTGCAT ATGGTCTCAG TGAAATGATA GTGATTATCA TAAGGAGT-- ---TTAAAGG 1490        1500        1510        1520        1530        1540
       *           *           *           *           *           *
    CAGGATGCAT TTTGTGTATG ANTGATTTTG GGTAGAATAT TTTTGGAACA GTTAAAATTT 1550        1560        1570        1580        1590        1600
       *           *           *           *           *           *
    ATGGGCTGCT GCACACTGGC TATGAACAAA TGTATAGCAT TAAAGTGCTT ATGACAAATT 1610        1620        1630        1640        1650        1660
       *           *           *           *           *           *
    CACAATTGTA TATTAGCAGC AGAGACATTA AAGTTTCTAA ATGCCTTTTA AGTAGATTGG 1670        1680        1690        1700        1710        1720
       *           *           *           *           *           *
```

Fig. 15C

```
AAAAAAGTGC TTTTTTTGGT TGAAGAAGCA CATTCACTAT TTGCCTGTTA ATGGAATTGG
        1730       1740       1750       1760       1770       1780
         *  *        *  *        *  *        *  *        *  *        *  *
TAATGATGAA TCACAAGGAT ATTTGTGAAT ACAAGCAGGA TGCTTTTAGT GTGCAAGTGA
        1790       1800       1810       1820       1830       1840
         *  *        *  *        *  *        *  *        *  *        *  *
TCTTTCGGAA CATTTAAAAT CGTCATAACA AAGGTGTAAC ATAAGAAGGC TTTGAAATAT
                                        >3'_splice_site
                                                |
        1850       1860       1870        |  1880       1890
         *  *        *  *        *  *        *  *        *  *
TCTCAATTTC TCATTGATTG AATGAATTAT GTGTTAG GGT GGA GAT GTG GGT ACT
                                         Gly Gly Asp Val Gly Thr>
                                            b___EXON 2_b___b___>

>ClaI
     |
    1900|      1910       1920       1930       1940
     *|         *  *        *  *        *  *        *  *
CAA TAT CGA TCT GGA ATA TAC TAC TAC AAC GAA ACG CAG GCC CGT CTA
Gln Tyr Arg Ser Gly Ile Tyr Tyr Tyr Asn Glu Thr Gln Ala Arg Leu>
___b___b___b___b___b___b____EXON 2_b___b___b___b___b___b___b___>

1950       1960       1970       1980       1990
     *  *        *  *        *  *        *  *        *
GCA CAG GAA TCA AAG GAA GCA AAG CAA CTG GAG TTT AAG GAT AAG AAG
Ala Gln Glu Ser Lys Glu Ala Lys Gln Leu Glu Phe Lys Asp Lys Lys>
___b___b___b___b___b___b____EXON 2_b___b___b___b___b___b___b___>

2000       2010       2020       2030
     *  *        *  *        *  *        *  *
GTG GTG ACA GAG ATT CTT CCA GCA AAG AGG TTT TAC AGG GCA GAG GAG
Val Val Thr Glu Ile Leu Pro Ala Lys Arg Phe Tyr Arg Ala Glu Glu>
___b___b___b___b___b___b____EXON 2_b___b___b___b___b___b___b___>

2040       2050       2060       2070       2080
     *  *        *  *        *  *        *  *        *  *
TAC CAT CAG CAA TAT CTC GCA AAG GGA GGA GGT AAT GGC AAC AAA CAA
Tyr His Gln Gln Tyr Leu Ala Lys Gly Gly Gly Asn Gly Asn Lys Gln>
___b___b___b___b___b___b____EXON 2_b___b___b___b___b___b___b___>

2090       2100       2110       2120       2130
     *  *        *  *        *  *        *  *        *  *
TCT GCT GAA AAA GGT TGC AAT GAT CCT ATT CGA TGC TAT GGT TGA
Ser Ala Glu Lys Gly Cys Asn Asp Pro Ile Arg Cys Tyr Gly ***>
___b___b___b___b___b___b_EXON 2___b___b___b___b___b___b___>

2140       2150       2160       2170       2180       2190
     *  *        *  *        *  *        *  *        *  *        *  *
GAAACTAA TGCATTATGC CATTATTAAA ACTCTACTGG TTTACTATGC AGAAACACCT
                              >BanI
                                |
    2200       2210        |  2220       2230       2240       2250
     *  *        *  *        *  *        *  *        *  *        *  *
```

Fig. 15D

```
ATGTCAGTTC AATTATACTG AAGGCACCAA AGTGTCATCT TAAATTATAT GGCAATGTTT

>SalI
                           |
   >Predicted_poly_A_site  |
              |            |
       2260   |    2270    2280       2290       2300       2310
         *    *  | *    *    *  | *     *    *     *    *     *    *
TACTCGTTAT GAATAAAGGA GGTCCAAGTC GACCAGATAT GAACAAATGA AATATTGCCA >EcoRV
                                                            |
       2320       2330       2340       2350       2360     | 2370
         *    *     *    *     *    *     *    *     *    * | *    *
TGTTAATTGG AATCCAGTAG TAATTAGGAT TTGTTTTGGT GTATGTACTC CGATATCAAG 2380       2390       2400       2410       2420       2430
         *    *     *    *     *    *     *    *     *    *     *    *
ATATGCAAAT GATGCATTGT GTTTTATAT ATTGACAAGT TCCAAATTAT AGTACTTCGT 2440       2450       2460       2470       2480       2490
         *    *     *    *     *    *     *    *     *    *     *    *
ATGTGTTATG CGGTTTAATT AGTGTTGCTT ACTTGAATGG TATATTACTA TTATGCTTAG 2500       2510       2520       2530       2540       2550
         *    *     *    *     *    *     *    *     *    *     *    *
TAGGAACTAG GAACTAGGGA ATATGTTGTG ATAGAGTTGT CCAACGAAAT TTTTGACCAA >Predicted_poly_A_site
              |
       2560   |    2570       2580       2590       2600       2610
         *    *  | *    *     *    *     *    *     *    *     *    *
AGTTATTTCA TTGAATAAAA ACTACAGTCT TAGAGATACA TCCAATTCTA TAAAGTGAAA 2620       2630       2640       2650       2660       2670
         *    *     *    *     *    *     *    *     *    *     *    *
GAAGCAAATA TTATTTGTTC ATGAGGCTAT GAGTCATGAA CTTTATGCTA TAACCGAAGC 2680       2690       2700       2710
         *    *     *    *     *    *     *    *
AACCTCAGAA AAGTCGAAGT AAATTGTGTA TTGTTTAGAG CTC
```

Fig. 15E

```
   1 gaattctcaa ttgagcccaa ttcaatctcc aatttcaacc cgttttaaaa cttttttatta
  61 agatatgttt ctatattgaa agtatgaatt attatctatt taacatcttt taggatttat
 121 ctatccattt gctactttt taacaaaaaa ttcttgagtg aaaattcaaa ttgtgattat
 181 aaaagttaaa tatcaatatg ttaaattatt aagattaatc gggtcaaatt ggcgggtcaa
 241 ggcccaattc ttttttagcc catttaagct caaagtaaac ttgggtgggt caagacccaa
 301 ctcgatttct gttcaaccca ttttaatatt tctattttca acctaacccg ctcatttgat
 361 accccctacaa atatcatatt tgtgtgtgaa atatttttg ggctggagag agaggccccg
 421 aggggagtgg aggggtgggg tggggagaga gagcgagaaa gagtggagag agaaatttga
 481 tatgaaatcc tacatatatt acagattgta atgttctaaa ctataacgat ttgtcataaa
 541 cacatatcat ggatttgtct ttttgtgtaa ttttcccaat tgtaaatagg acttcgttat
 601 ttgaaacttg aaagtgaagt cacatagatt aagtacaaac attaattaaa gaccgtggtg
 661 gaatgataaa tatttattta tctttaatta gttatttttt tgggagctct ttattccaat
 721 gtgagacttt tgcgacatat attcaaattt aatcgaatca caatatgtat tagattgata
 781 aaaaaataat ttttttacaa tgttagttga gactcataac ttactgccta ttggtaatct
 841 atgactccta attccttaat tatttaaata tatcatcttg atcgttaaca aagtaatttc
 901 gaaagaccac gagtaagaag acaaacgaga ataccaaaaa attcaaaaat ttaatgtgat
 961 ttggtcaatc gatctacgtc cataaaggag atgagtaatc tactataaat atgagagtac
1021 aaaatacaga gagaaacaac ctcaactaat tcactcggaa tacatgagaa gttcacacaa
1081 gtgataacgt atcaaacttg tgacccacac ttttccctct aaccaaagct cttaaaacta
1141 tattgtgaat gctgattaag ttaaacgaaa cagtcctaaa tcttttccgt cctatgagaa
1201 acaagattaa tcaattcaca attttttaa aaagaaaaac ctgtaagaaa tttaggcaaa
1261 caaaacctaa cacaagtttg ttttgtttt tactaccaac aagaaattca aatggcaaat
1321 gtaacgca tcttagctaa ttatatgacc agattcagat taatatacat cttcacccat
1381 gcaatccatt tctatataaa gaaacataca cgaacttgat attattagag attgagcaat
1441 ggagggtaac aacagcagta gcaagtcaac caccaatcca gcattggatc cggatctgga
1501 cagcccggat cagccgggtc tggagtttgc ccaatttgct gccggctgct tttggggagt
1561 cgaattggct ttccagaggg ttggaggagt agtgaagacg gaggttgggt actctcaggg
1621 gaatgtccat gacccgaact acaagcttat tgctccgga caaccgaac atgccgaggc
1681 cattcggatc cagtttgacc cgaatgtctg cccgtattcc aatctccttt ctctattttg
1741 gagtcgccat gacccgacca ctctaaatcg ccaggtatca aattcctttg gtgtttcatt
1801 ttatgtgatt aatattaaaa attttttata taaatgtcat gatgatggtt gttgctaggg
1861 taatgatgtg ggaaagcaat accgctcagg aatatattac tataatgatg ctcaggctca
1921 actggcaagg gagtcgttag aagctaagca gaaggaattt atggataaga aaattgtcac
1981 tgaaattctt cctgctaaga gattttatag agctgaagag tatcaccagc aatatctaga
2041 gaagggtggg ggcagaggtt gtaagcagtc ggctgcaaag ggctgcaatg acccaataag
2101 gtgctacggt tgacagcaga tctttgaatg tcatagcaac tacaaaagaa cttgttagac
2161 atttgctgtc ttgcttcttt aaatttgaat aaacatgaca atgattctta taactacttg
2221 ctctcttgga tggaataact agttgtcgta agtattctc ctcttgctaa ttattatctc
2281 tctttatatg gtacctgcaa tttgttgctt tagttacaga ataatggacg tcaattctat
2341 atcttaattt gttttaagtc ttaaatgagg tggtttgtgt ttgaaagcaa tatcaagcat
2401 agtaatacca atgatttagt agatgaactt aatcaaatca aattccaaaa tgcagtctac
2461 aaattgacaa catgaagtta agtgtatctt atgtaaattg acatctttcc tagtagatgc
2521 ctaatacttt tgtaaagact aaaataagca cagatgaggc ttgtgcattt aacttagagt
2581 tcatccttag gtgtggctgc aggagaccct gtagggttgc ttgaagtctt gatggggtag
2641 gagggttgca ttgctatacc acacaacccc tcttcagcgt caaccttgcg ctgcattcta
2701 atgtatcctt tttctcccca ttcagctccc catgagttct tcacaatcca gtatttggtt
2761 ccatcgacgg ttgtgccata ccccacaata gccaca
```

Fig. 24

```
>Hind3
|
|          10         20         30         40         50         60         70
|        *  *       *  *       *  *       *  *       *  *       *  *       *  *
    AAGCTTAAAG TAAACTTGGG TGGGTCAAGA CCCAACTCGA TTTCTGTTCA ACCCATTTTA ATATTTCTAT
    _____>
           b           b     _____TOMATO E4 PROMOTER_____b_____b_____>

80         90        100        110        120        130        140
        *  *       *  *       *  *       *  *       *  *       *  *       *  *
    TTTCAACCTA ACCCGCTCAT TTGATACCCC TACAAATATC ATATTTGTGT GTGAAATATT TTTTGGGCTG
           b_          b_____TOMATO E4 PROMOTER_____b_____b_____>

150        160        170        180        190        200        210
        *  *       *  *       *  *       *  *       *  *       *  *       *  *
    GAGAGAGAGG CCCCGAGGGG AGTGGAGGGG TGGGGTGGGG AGAGAGAGCG AGAAAGAGTG GAGAGAGAAA
           b           b_____TOMATO E4 PROMOTER_____b_____b_____>

220        230        240        250        260        270        280
        *  *       *  *       *  *       *  *       *  *       *  *       *  *
    TTTGATATGA AATCCTACAT ATATTACAGA TTGTAATGTT CTAAACTATA ACGATTTGTC ATAAACACAT
           b           b_____TOMATO E4 PROMOTER_____b_____b_____>

290        300        310        320        330        340        350
        *  *       *  *       *  *       *  *       *  *       *  *       *  *
    ATCATGGATT TGTCTTTTTG TGTAATTTTC CCAATTGTAA ATAGGACTTC GTTATTTGAA ACTTGAAAGT
           b           b_____TOMATO E4 PROMOTER_____b_____b_____>

360        370        380        390        400        410        420
        *  *       *  *       *  *       *  *       *  *       *  *       *  *
    GAAGTCACAT AGATTAAGTA CAAACATTAA TTAAAGACCG TGGTGGAATG ATAAATATTT ATTTATCTTT
           b           b_____TOMATO E4 PROMOTER_____b_____b_____>

430        440        450        460        470        480        490
        *  *       *  *       *  *       *  *       *  *       *  *       *  *
    AATTAGTTAT TTTTTTGGGA GCTCTTTATT CCAATGTGAG ACTTTTGCGA CATATATTCA AATTTAATCG
           b           b_____TOMATO E4 PROMOTER_____b_____b_____>

500        510        520        530        540        550        560
        *  *       *  *       *  *       *  *       *  *       *  *       *  *
    AATCACAATA TGTATTAGAT TGATAAAAAA ATAATTTTTT TACAATGTTA GTTGAGACTC ATAACTTACT
           b           b_____TOMATO E4 PROMOTER_____b_____b_____>

570        580        590        600        610        620        630
        *  *       *  *       *  *       *  *       *  *       *  *       *  *
    GCCTATTGGT AATCTATGAC TCCTAATTCC TTAATTATTT AAATATATCA TCTTGATCGT TAACAAAGTA
           b           b_____TOMATO E4 PROMOTER_____b_____b_____>

640        650        660        670        680        690        700
        *  *       *  *       *  *       *  *       *  *       *  *       *  *
    ATTTCGAAAG ACCACGAGTA AGAAGACAAA CGAGAATACC AAAAAATTCA AAAATTTAAT GTGATTTGGT
           b           b_____TOMATO E4 PROMOTER_____b_____b_____>
```

Fig. 25A

```
          710        720        730        740        750        760        770
           *    *     *    *     *    *     *    *     *    *     *    *     *    *
CAATCGATCT ACGTCCATAA AGGAGATGAG TAATCTACTA TAAATATGAG AGTACAAAAT ACAGAGAGAA
_____b_____b_____TOMATO  E4  PROMOTER_____b_____b_____>

780        790        800        810        820        830        840
           *    *     *    *     *    *     *    *     *    *     *    *     *    *
ACAACCTCAA CTAATTCACT CGGAATACAT GAGAAGTTCA CACAAGTGAT AACGTATCAA ACTTGTGACC
_____b_____b_____TOMATO  E4  PROMOTER_____b_____b_____>

850        860        870        880        890        900        910
           *    *     *    *     *    *     *    *     *    *     *    *     *    *
CACACTTTTC CCTCTAACCA AAGCTCTTAA AACTATATTG TGAATGCTGA TTAAGTTAAA CGAAACAGTC
_____b_____b_____TOMATO  E4  PROMOTER_____b_____b_____>

920        930        940        950        960        970        980
           *    *     *    *     *    *     *    *     *    *     *    *     *    *
CTAAATCTTT TCCGTCCTAT GAGAAACAAG ATTAATCAAT TCACAATTTT TTTAAAAAGA AAAACCTGTA
_____b_____b_____TOMATO  E4  PROMOTER_____b_____b_____>

990        1000       1010       1020       1030       1040       1050
           *    *     *    *     *    *     *    *     *    *     *    *     *    *
AGAAATTTAG GCAAACAAAA CCTAACACAA GTTTGTTTTT GTTTTACTA CCAACAAGAA ATTCAAATGG
_____b_____b_____TOMATO  E4  PROMOTER_____b_____b_____>

1060       1070       1080       1090       1100       1110       1120
           *    *     *    *     *    *     *    *     *    *     *    *     *    *
CAAATGTATA ACGCATCTTA GCTAATTATA TGACCAGATT CAGATTAATA TACATCTTCA CCCATGCAAT
_____b_____b_____TOMATO  E4  PROMOTER_____b_____b_____>

>NcoI
                                                                |
          1130       1140       1150       1160       1170      |  1180
           *    *     *    *     *    *     *    *     *    *   |  *    *    *
CCATTTCTAT ATAAAGAAAC ATACACGAAC TTGATATTAT TAGAGATTGA GCC ATG GTT TTC ACT
                                                            Met Val Phe Thr>
                                                            ___e_SAMK__e____>
_____b_____TOMATO  E4  PROMOTER_____b_____b_>
                                                            ___KOZAK LINKER____>

>XmnI
                   |
       1190      1200  |    1210       1220       1230       1240
        *    *    *    |*    *    *    *    *    *    *    *    *
AAA GAG CCT GCG AAC GTC TTC TAT GTA CTG GTT TCC GCT TTC CGT TCT AAC CTC TGC
Lys Glu Pro Ala Asn Val Phe Tyr Val Leu Val Ser Ala Phe Arg Ser Asn Leu Cys>
___e___e___e___e___e___e___e___e___SAMase__e___e___e___e___e___e___e___e___>
_KOZAK LINKER_____>
```

Fig 25B

```
         1250       1260       1270       1280       1290
   *       *    *    *    *    *    *    *    *    *    *
GAT GAG GTG AAT ATG AGC AGA CAC CGC CAC ATG GTA AGC ACT TTA CGT GCC GCA CCG
Asp Glu Val Asn Met Ser Arg His Arg His Met Val Ser Thr Leu Arg Ala Ala Pro>
___e___e___e___e___e___e___e___e___SAMase__e___e___e___e___e___e___e___e___>

1300       1310       1320       1330       1340       1350
   *    *    *    *    *    *    *    *    *    *    *    *
GGT CTT TAT GGC TCC GTT GAG TCA ACC GAT TTG ACC GGG TGC TAT CGT GAG GCA ATC
Gly Leu Tyr Gly Ser Val Glu Ser Thr Asp Leu Thr Gly Cys Tyr Arg Glu Ala Ile>
___e___e___e___e___e___e___e___e___SAMase__e___e___e___e___e___e___e___e___>

1360       1370       1380       1390       1400       1410
   *    *    *    *    *    *    *    *    *    *    *    *
TCA AGC GCA CCA ACT GAG GAA AAA ACT GTT CGT GTA CGC TAC AAG GAC AAA GCG CAG
Ser Ser Ala Pro Thr Glu Glu Lys Thr Val Arg Val Arg Tyr Lys Asp Lys Ala Gln>
___e___e___e___e___e___e___e___e___SAMase__e___e___e___e___e___e___e___e___>

1420       1430       1440       1450       1460       1470
   *    *    *    *    *    *    *    *    *    *    *    *
CCA CTC AAT GTT GCA CGC CTA GCT TCT AAT GAG TGG GAG CAA GAT TGC GTA CTG GTA
Pro Leu Asn Val Ala Arg Leu Ala Ser Asn Glu Trp Glu Gln Asp Cys Val Leu Val>
___e___e___e___e___e___e___e___e___SAMase__e___e___e___e___e___e___e___e___>

1480       1490       1500       1510       1520
   *    *    *    *    *    *    *    *    *    *    *
TAC AAA TCA CAG ACT CAC ACG GCT GGT CTG GTG TAC GCT AAA GGT ATC GAC GGG TAT
Tyr Lys Ser Gln Thr His Thr Ala Gly Leu Val Tyr Ala Lys Gly Ile Asp Gly Tyr>
___e___e___e___e___e___e___e___e___SAMase__e___e___e___e___e___e___e___e___>

1530       1540       1550       1560       1570       1580
   *    *    *    *    *    *    *    *    *    *    *
AAG GCT GAA CGT CTG CCG GGT AGT TTC CAA GAG GTT CCT AAA GGC GCA CCG CTG CAA
Lys Ala Glu Arg Leu Pro Gly Ser Phe Gln Glu Val Pro Lys Gly Ala Pro Leu Gln>
___e___e___e___e___e___e___e___e___SAMase__e___e___e___e___e___e___e___e___>

>Stop Codon
                                                          |
     1590       1600       1610       1620       1630|      1640
   *    *    *    *    *    *    *    *    *    *   *|   *    *
GGC TGC TTC ACT ATT GAT GAG TTC GGT CGC CGC TGG CAA GTA CAA TAA CGTGTTAA
Gly Cys Phe Thr Ile Asp Glu Phe Gly Arg Arg Trp Gln Val Gln ***
___e___e___e___e___e___e___SAMase__e___e___e___e___e___e___>

>Kpn I
                                   |
       1650       1660       1670  1678
   *    *    *    *    *    *    *
ACTCAAGGTC ATGCACGATG CGTGGCGGAT CGGGTACC
```

Fig 25C

REGULATED EXPRESSION OF HETEROLOGOUS GENES IN PLANTS AND TRANSGENIC FRUIT WITH A MODIFIED RIPENING PHENOTYPE

This application is a continuation-in-part of co-owned, co-pending, U.S. patent application Ser. No. 08/261,677, filed 17 Jun. 1994, herein incorporated by reference, and a continuation-in-part of co-owned, co-pending, U.S. patent application Ser. No. 08/046,583, filed 9 Apr. 1993, herein incorporated by reference, and a continuation-in-part of co-owned, U.S. patent application Ser. No. 08/255,833, filed 8 Jun. 1994, herein incorporated by reference, now U.S. Pat. No. 5,416,250, which is a file-wrapper continuation of co-owned, U.S. patent application Ser. No. 07/613,858, filed 12 Dec. 1990, now abandoned which is a continuation-in-part of U.S. patent application Ser. No. 448,095 filed Dec. 12, 1989, now abandoned.

FIELD OF THE INVENTION

The present invention relates to the regulated expression of heterologous genes in transgenic fruit-bearing plants, where fruit produced by the these plants has a modified ripening phenotype. The invention also relates to the fruit produced by such transgenic plants, to methods of producing the transgenic plants and to the transgenic plants themselves.

REFERENCES

Adams, D. O., and Yang, S. F., *Plant Physiology* 70:117–123 (1977).
An, G., et al., *EMBO J.* 4:277–284 (1985).
An, G. et al., "Binary Vectors", in *PLANT MOLECULAR BIOLOGY MANUAL A*3:1–19 (1988).
Ausubel, F. M., et al., *CURRENT PROTOCOLS IN MOLECULAR BIOLOGY*, John Wiley and Sons, Inc., Media Pa.
Becker, D., et al., *Plant Mol. Biol.* 20:1195–1197 (1992).
Bellini, C., et al., *Bio/Technol* 7(5):503–508 (1989).
Bird, C. R., et al., *Plant Mol. Bio.* 11:651–662 (1988).
Cass, L. G., et al., *Mol. Gen. Genet.* 223:76–86 (1990).
Comai, L. and Coning, A. J., U.S. Pat. No. 5,187,267, issued 16 Feb. 1993.
Cordes, S., et al., *The Plant Cell* 1:1025–1034 (1989).
Dayhoff, M. O., in *ATLAS OF PROTEIN SEQUENCE AND STRUCTURE* (1972) Vol. 5, National Biomedical Research Foundation, pp. 101–110, and Supplement 2 to this volume, pp. 1–10.
Deikman, J., et al., *EMBO J.* 7:3315 (1988).
Deikman, J., et al., *Plant Physiol.* 100:2013 (1992).
Fillatti, J. J., et al., *Biotechnology* 5:726–730 (1987).
Fritsch, E. F., et al., in *MOLECULAR CLONING: A LABORATORY MANUAL* (Cold Spring Harbor Lab., Cold Spring Harbor, N.Y.), 2nd Ed. (1989).
Gallie, D. R., *Ann. Rev. Plant Physiol. and Plant Mol. Biol.* 44:77–105 (1993).
Giovannoni, J. J., et al., *Plant Cell* 1:53–63 (1989).
Goding, J. W., *J. Immun. Methods* 39:285–308 (1980).
Hamilton, A. J., et al., *Nature* 346:284–287 (1990).
Holdsworth, M. J., et al., *Nuc. Acids Res.* 15:731–739 (1987).
Hood, E., et al., *J. Bacteriol.* 168:1291–1301 (1986).
Horsten, K. H., et al., *J. Gen. Virol.* 43:57–73 (1979).
Houck, C. M. and Pear, J. R., U.S. Pat. No. 4,943,674, issued 24 Jul. 1990.
Hughes, J. A., et al., *J. Bact.* 169:3625–3632 (1987a).
Hughes, J. A., et al., *Nuc. Acid. Res.* 15:717–729 (1987b).
Imaseki, H., "The biochemistry of ethylene biosynthesis" in *THE PLANT HORMONE ETHYLENE* (Matoo, A. K., and Suttle, J. C., Eds.), CRC Press, pp. 1–20 (1991).
Jorgensen, R. A., et al., U.S. Pat. No. 5,034,323, issued 23 Jul. 1991.
Jorgensen, R. A., et al., U.S. Pat. No. 5,231,020, issued 27 Jul. 1993.
Joshi, C. P., *Nuc. Acid Res.* 16:6643–6653 (1987).
Kende, H., *Plant Physiol.* 91:1–4 (1989).
Kende, H., *Ann. Rev. Plant Physiol. and Plant Mol. Biol.* 44:282–307 (1993).
Klee, H. J., et al., *Plant Cell* 3:1187–1193 (1991).
Klein, T. M., et al., *PNAS (USA)* 85(22):8502–8505 (1988).
Kozak, M., *J. Mol. Bio.* 196:947 (1987).
Kozak, M., *Mol. Cell Biol.* 9:5073–5080 (1989).
Kushad, M. M., et al., *Plant Physiol.* 73:257–251 (1983).
Lee, J. J., et al., *Methods in Enzymology* 152:633–648 (1987).
Lincoln, J. E., et al., *Proc. Natl. Acad. Sci. USA* 84:2793 (1987).
Lincoln, J. E., and Fischer, R. L., *Plant Physiol.* 88:370–374 (1988).
Lutcke, H. A., et al., *EBMO J.* 6:43–48 (1987).
Maniatis, T., et al. *MOLECULAR CLONING: A LABORATORY MANUAL*, Cold Spring Harbor Laboratory (1982).
Mertens, H., et al., *J. Gen. Virol.* 62:331–341 (1982).
Miki, B. L. A., et al., *PLANT DNA INFECTIOUS AGENTS* (Hohn, T., et al., eds.) Springer-Verlag, Wien, Austria, pp.249–265 (1987).
Mullis, K. B., U.S. Pat. No. 4,683,202, issued 28 Jul. 1987.
Mullis, K. B., et al., U.S. Pat. No. 4,683,195, issued 28 Jul. 1987.
Nagel, R., et al., *FEMS Microbiol. Lett.* 67:325 (1990).
Oeller, P. W., et al., *Science* 254:437–439 (1991).
Sambrook, J., et al., In *MOLECULAR CLONING: A LABORATORY MANUAL*, Cold Spring Harbor Laboratory Press, Vol. 2 (1989).
Sheehy, R. E., et al., *J. Bact.* 173:5260–5265 (1991).
Studier, F. W., et al., *J. Virol* 19:136 (1976).
Studier, F. W., and Movva, N. R., *J. Virol.* 19:136–145 (1993).
Theologis, A., *Cell* 70:181–184 (1992).
Van der Straeten, D., et al., *Proc. Natl. Acad. Sci. USA* 87:4859–4863 (1990).
Ward, T. M., et al., *ANALYTICAL PROCEDURES FOR THE ASSAY AND IDENTIFICATION OF ETHYLENE* (Hillman, J., Ed.) Cambridge University Press, Cambridge, Mass., pp. 135–151 (1978).

BACKGROUND OF THE INVENTION

Ethylene is a plant hormone which is a powerful regulator of plant metabolism, acting, and interacting with other plant hormones in trace amounts. Ethylene is a gas under normal physiological conditions. Even at low concentrations, ethylene has profound hormonal effects on plants.

The effects of ethylene, whether produced by the plant itself or applied exogenously, are numerous, dramatic, and of considerable commercial importance. Among the diverse physiological effects are the following: leaf abscission; fading in flowers; flower wilting; leaf yellowing; leaf epinasty; and stimulation of ripening in fruits and vegetables. Ethylene promotes senescence in plants, both in selected groups of cells and in whole organs, such as, fruits, leaves, or flowers. Senescence is the natural, genetically controlled degenerative process which usually leads to death in plants.

Normally, ethylene production from plant tissue is low. Large quantities of ethylene, however, are produced during ripening and senescence processes. A large amount of ethylene is also produced following trauma caused by chemicals, temperature extremes, water stress, ultraviolet light, insect damage, disease, or mechanical wounding. Ethylene produced by plants under such trauma conditions is referred to as "wound ethylene" or "stress ethylene". In fruits and vegetables, the stimulation of ethylene production by cuts or bruises may be very large and bear considerably on storage effectiveness. Ethylene-induced leaf browning is a common basis for loss in many plants, including lettuce and tobacco. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

Current technologies that specifically address postharvest storage life have been in existence for decades and are hampered by such problems as high cost, side effects, and an inability to completely shut off ethylene production. Included in this group are controlled atmosphere (CA) storage, chemical treatment, packaging, and irradiation.

CA facilities slow ethylene biosynthesis through: (i) low temperature, (ii) reducing the oxygen level below 3%, and (iii) elevating the carbon dioxide level in the storage area to the 3%–5% range. Expensive scrubbers are sometimes added which reduce ethylene already respired to the atmosphere. Drawbacks are that CA facilities are expensive to construct, have a high utility cost, and are unable to completely eliminate ethylene production and side effects. Also, CA storage techniques can only control external ethylene and not that which resides inside the plant tissue. CA storage can also lead to undesirable side effects: injury can result from high $CO_2$ levels, low $O_2$ levels, or low temperature.

Another treatment is to limit the ethylene biosynthesis in the plant tissue through chemical treatment. Aminoethoxyinylglycine (AVG), an analog of the antibiotic rhizobitoxine, is one such inhibitor. However, AVG cannot be used as a chemical additive in foods due to its high toxicity. Silver thiosulfate (STS) is also effective in slowing fruit ripening and flower fading, but is also toxic and cannot be used on foods. Further, STS only works with certain flowers and often causes black spotting.

Recently, molecular genetic approaches leading to transgenic plants with impaired biosynthesis of ethylene have been reported. Hamilton, et al., identified a cDNA clone for tomato EFE (pTOM13) by inhibiting ethylene synthesis with an antisense gene expressed in transgenic plants. Oeller, et al., showed that expression of antisense RNA to the rate-limiting enzyme in the biosynthetic pathway of ethylene, 1-aminocyclopropane-1-carboxylate synthase, inhibits fruit ripening in tomato plants. Klee, et al., cloned the gene encoding ACC deaminase, from soil bacteria, and introduced it into tomato plants. Reduction in ethylene synthesis in transgenic plants did not cause any apparent vegetative phenotypic abnormalities. However, fruits from these plants exhibited significant delays in ripening, and the mature fruits remained firm for at least 6 weeks longer than the non-transgenic control fruit.

SUMMARY OF THE INVENTION

The present invention relates to plant transformation vectors, chimeric genes and related DNA constructs. In one embodiment the invention relates to a transgenic fruit-bearing plant having (i) a DNA sequence encoding a product that is effective to reduce ethylene biosynthesis in fruit from the plant, and (ii) a promoter whose expression is induced during fruit ripening, by a plant cell cytokine, or by ethylene synthesis by the fruit. The DNA sequence is heterologous to the promoter and is operably linked to the promoter to enable expression of said product. The DNA sequence may encode any of the following products: S-adenosylmethionine hydrolase, aminocyclopropane-1-carboxylic acid (ACC) deaminase, ACC oxidase antisense molecule, ACC synthase antisense molecule, ACC oxidase cosuppression molecule, and ACC synthase cosuppression molecule.

Promoters useful in the present invention may be selected from a variety of plant sources, including, but not limited to, genes homologous to a tomato E4 or E8 gene, including tomato and raspberry E4 and E8 genes. Other exemplary promoters may be obtained from the avocado cellulase gene, tomato ACC oxidase gene, tomato polygalacturonase gene, or homologs of any of these genes in other plants.

The present invention also includes a method for modifying ripening fruit of a fruit bearing plant. In the method, the transgenic plants described above are grown to produce a transgenic plant bearing fruit. Fruit produced by the plant has an initial burst of ethylene production, followed by a reduction in the level of ethylene synthesis by the fruit, resulting in a fruit having a modified ripening phenotype. Such phenotypes include the delay and/or suspension of fruit ripening, typically relative to wild-type (i.e., non-transgenic) fruit.

In another aspect, the present invention includes the above described transgenic fruit and fruit cells.

Further, the invention includes a method for producing a transgenic fruit-bearing plant, where fruit produced by the plant has a modified ripening phenotype. In this method, the following chimeric gene is introduced (e.g., by transformation) into progenitor cells of the plant: (i) a DNA sequence encoding a product effective to reduce ethylene biosynthesis in fruit from the plant, and (ii) a promoter whose expression is induced during fruit ripening, by a plant cytokine, or by ethylene synthesis by the fruit. As above, the DNA sequence is heterologous to the promoter and is operably linked to said promoter to enable expression of the product. The transformed progenitor are grown cells to produce a transgenic plant bearing fruit. The method further includes transforming progenitor cells of the plant with a selectable vector containing chimeric gene. The DNA sequences and promoters may be as described above.

In another aspect, this method includes isolating useful promoters, typically, employing the following steps:
  (i) selecting a probe DNA molecule containing a sequence homologous to a region of the promoter of interest, such as from the tomato E4 or E8 genes;
  (ii) contacting the probe with a plurality of target DNA molecules derived from the genome of a selected fruit-bearing plant under conditions favoring specific hybridization between the probe molecule and a target molecule homologous to the probe molecule;
  (iii) identifying a target molecule having a DNA sequence homologous to the probe; and
  (iv) isolating promoter sequences associated with the target molecule.

The invention also includes expression vectors containing the chimeric genes described above. These vectors are useful for transformation of plant cells and may be included in commercial kits.

Another embodiment of the present invention is a polypeptide in a plant having (i) a DNA sequence encoding a product that is effective to reduce ethylene biosynthesis in fruit from the plant, and (ii) a promoter whose expression is induced during fruit ripening or by ethylene synthesis by said fruit, where said DNA sequence is heterologous to said promoter and said DNA sequence is operably linked to said promoter to enable expression of said product. In another aspect, the invention includes plant and fruit cells containing such chimeric genes, as well as vectors containing such genes.

One embodiment of the invention is a method for delaying wound-induced ripening of fruit of a fruit-bearing plant. This method includes transforming progenitor cells of the plant with a selectable vector containing (i) a promoter that has the sequence of the tomato E4 gene promoter or the sequence of a promoter for a gene homologous to the tomato E4 gene, and (ii) a heterologous gene, whose product is effective to reduce ethylene biosynthesis in fruit from the plant, which is under the control of the promoter, growing the transformed progenitor cells to produce a transgenic plant bearing fruit, and subjecting the fruit to a wound. The method also includes subjecting the fruit to a wound by picking the fruit from a transgenic plant. In the method, an exemplary heterologous gene is S-adenosylmethionine hydrolase.

The transgenic plant may be selected from the group consisting of, but not limited, to tomato, raspberry, strawberry and melon. The promoter may be selected from the same group. Further plant species are described in the specification. In one embodiment the promotor is a tomato E4 promoter.

In another aspect of the invention, the promoter is isolated by the steps of (i) selecting a probe DNA molecule containing a sequence homologous to a region of tomato E4 gene DNA, (ii) contacting the probe with a plurality of target DNA molecules derived from the genome of a selected fruit-bearing plant under conditions favoring specific hybridization between the probe molecule and a target molecule homologous to the probe molecule, (iii) identifying a target molecule having a DNA sequence homologous to tomato E4 gene, and (iv) isolating promoter sequences associated with the target molecule.

The probe molecule may carry a reporter moiety; the identifying step then includes detecting the moiety.

The method also describes isolating the promotor by (i) selecting first and second oligonucleotide primers corresponding to an upstream and a downstream region, respectively, of an E4 gene, (ii) amplifying a region of the E4 gene DNA between the first and second primers to generate probe molecules, (iii) contacting the probe molecules with a plurality of target DNA molecules derived from the genome of a selected fruit-bearing plant under conditions favoring specific hybridization between the probe molecule and a target molecule homologous to the probe molecule, (iv) identifying a target molecule having a DNA sequence homologous to tomato E4 gene, and (v) isolating promoter sequences associated with the target molecule.

The invention also describes a delayed-ripening fruit, containing (i) a heterologous S-adenosylmethionine hydrolase gene, and (ii) a promoter effective to produce transient expression of the gene when the fruit is picked.

A method is described for inducing transient, wound-induced expression of a heterologous gene in fruit of a fruit-bearing plant, comprising transforming progenitor cells of the plant with a selectable vector containing (i) a promoter that has the sequence of the tomato E4 gene promoter or the sequence of a promoter for a gene homologous to the tomato E4 gene, and (ii) a heterologous gene which is under the control of the promoter, growing the transformed progenitor cells to produce a transgenic plant bearing fruit, and subjecting the fruit to a wound. In this method, expression of the heterologous gene typically reduces ethylene biosynthesis. In one embodiment, the heterologous gene encodes S-adenosylmethionine hydrolase.

In one embodiment, the present invention includes, a method for delaying ripening of the fruit of a fruit-bearing plant. The method includes transforming plant progenitor cells, or host cells, with a selectable vector containing a plant E4 gene promoter and a heterologous gene, such as S-adenosylmethionine hydrolase, whose product reduces ethylene biosynthesis in the plant. The transformed cells are grown to produce a transgenic plant bearing fruit. In a related embodiment, the method is used, essentially as above, to delay senescence in flowers and vegetables. The E4 promoter, and/or the transformed plant, may be selected from a variety of plants, including fruit-bearing plants, such as tomato, eggplant, legumes, raspberry, strawberry, melon, avocado, cherry, apricot, citrus fruits, etc.; flowers, such as roses and carnations; and vegetables, such as cauliflower, and lettuce.

In another aspect, the invention includes a method of isolating E4 promoters from plants. The method includes selecting an E4 probe, hybridizing it with genomic DNA from selected plant species, identifying DNA or clones from positively-hybridizing targets, and isolating promoter sequences associated with the positive target molecule. Positively-hybridizing targets can be identified by either primary or secondary detection of reporter moieties attached to the probe. The probe can be obtained by a number of methods, including primer-based DNA amplification or isolation of restriction digest fragments.

In another embodiment, the invention includes a delayed-ripening fruit, containing a heterologous gene, such as the S-adenosylmethionine hydrolase gene, and a promoter, such as the E4 promoter, effective to produce transient expression of the heterologous gene when the fruit is picked. The promoter may be obtained from a variety of plants, such as outlined above, using methods of the present invention.

Also included in the present invention is an E4 promoter molecule and a DNA construct containing the promoter molecule operably linked to a heterologous gene, where expression of the heterologous gene is under the control of the promoter DNA molecule.

These and other objects and features of the invention will be more fully appreciated when the following detailed description of the invention is read in conjunction with the accompanying drawings.

BRIEF DESCRIPTION OF THE FIGURES

FIG. 9B, LS 4-2; FIG. 9C, ES 35-1; and FIG. 9D, ES22 A-1) over a ten day period after entry of the fruit into breaker stage.

FIGS. 11A to 11D present the sequence of the SAM-K modification of the AdoMetase gene derived from bacteriophage T3.

FIGS. 13A and 13B present the sequence of the upstream minus 2216 base pair region of the tomato E8 gene (SEQ ID NO: 24).

FIGS. 15A to 15E represent a DNA sequence of an isolated E4 gene from a raspberry genomic DNA library.

FIG. 24 shows the DNA sequence of the tomato E4 gene.

FIGS. 25A to 25C correspond to the DNA sequence of a HindIII/KpnI fragment containing the tomato E4 promoter and the SAMase gene, and the translated amino acid sequence of the SAMase gene.

DETAILED DESCRIPTION OF THE INVENTION

I. Definitions

Figure 1A:
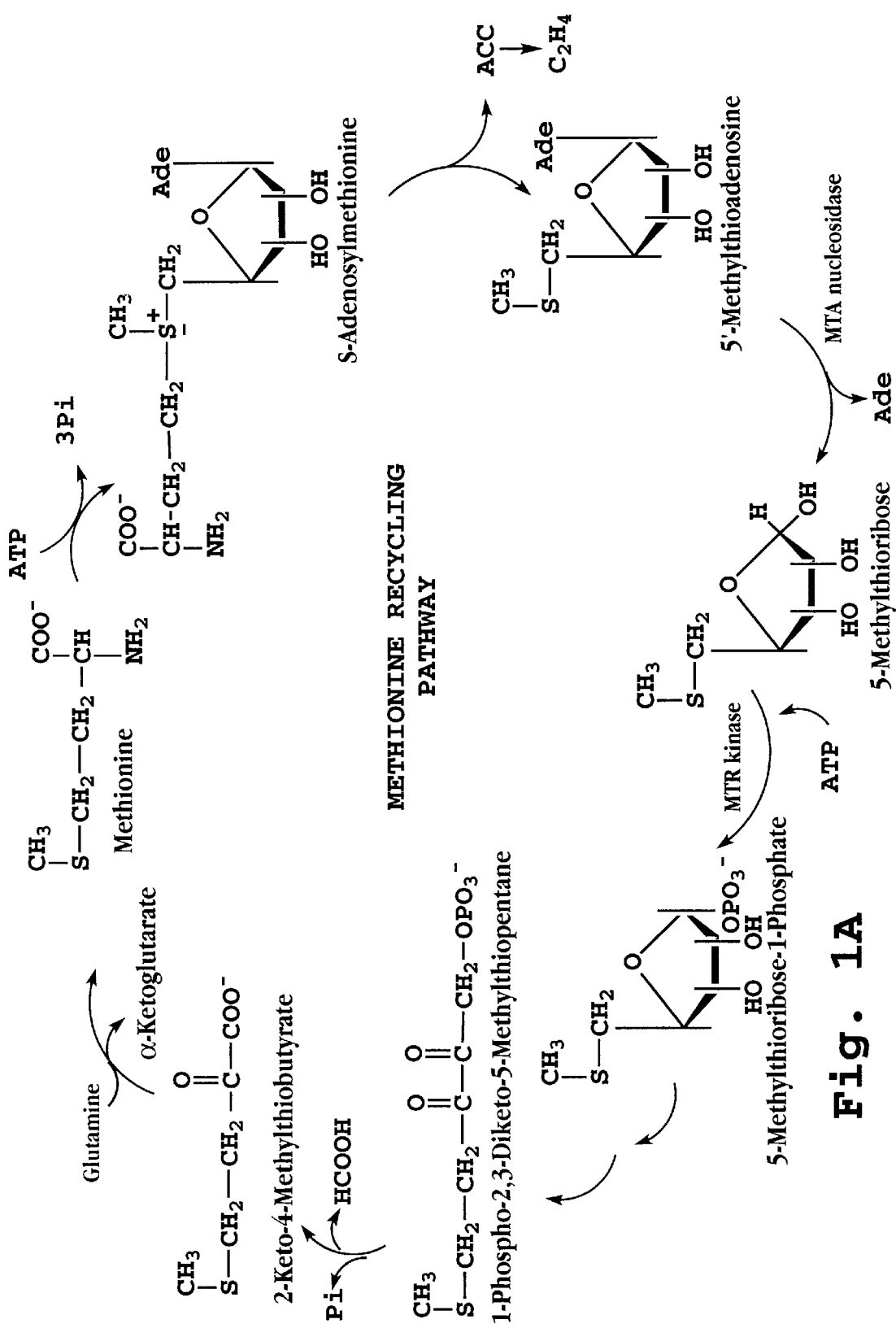
FIG. 1A schematically illustrates the metabolic reactions for the synthesis of ethylene from methionine under both normal and stress conditions.

"Heterologous" DNA refers to DNA which has been transfected into a host organism. Typically, heterologous DNA refers to DNA that is not originally derived from the transfected or transformed cells' genomic DNA (e.g., CAT and β-galactosidase gene sequences). However, any DNA introduced into an organism by recombinant means is referred to as heterologous DNA (e.g., introduction into a tomato of a vector carrying the tomato E4 promoter).

A "chimeric gene," in the context of the present invention, typically comprises a promoter sequence operably linked to non-homologous DNA sequences that encode a gene product (e.g., a tomato E8 promoter adjacent DNA sequences encoding S-adenosylmethionine cleaving enzyme).

Two nucleotide sequences are considered to be "functionally homologous" if they hybridize with one another under moderately stringent conditions, i.e. 0.1% SSC at room temperature. Examples of such hybridization conditions are given in Examples 6 and 7. Typically, two homologous nucleotide sequences are greater than or equal to about 60% identical when optimally aligned using the ALIGN program (Dayhoff).

Two amino acid sequences are considered "homologous" if their amino acids are greater than or equal to about 60% identical when optimally aligned using the ALIGN program mentioned above.

A "modified ripening" phenotype typically refers to an alteration of the rate of ripening of a transgenic fruit relative to corresponding wild-type fruit. For example, delayed ripening fruit (i.e., ripening takes longer than corresponding wild-type fruit) or suspension of the fruit's ability to complete the ripening process.

A "product" encoded by a DNA molecule includes, for example, RNA molecules and polypeptides.

II. Regulated Promoters for Expression of Genes in Plants.

The present invention provides a method to regulate plant cell expression of any gene in a tissue or development stage-specific manner, in particular, genes whose products reduce ethylene synthesis in plant cells. In one embodiment, the invention teaches the use of tissue/stage-specific promoters whose expression is induced during fruit ripening or by the presence of ethylene. To regulate cellular production of ethylene, a gene whose product results in a reduction of ethylene synthesis is operably linked to such promoter (creating a chimeric gene). In one aspect of the invention, an initial burst of ethylene synthesis occurs, expression of the chimeric gene is induced and production of ethylene by the cell is subsequently reduced. When the chimeric gene is present in fruit cells, the result is fruit having a modified ripening phenotype relative to wild-type (non-transgenic) fruit.

The initial burst of ethylene allows fruit to initiate ripening, but the subsequent down regulation of ethylene production delays the course of fruit ripening, i.e., the fruit are suspended in their ability to complete the ripening process. Climateric or non-climateric fruit may be produced by this method.

Several examples of regulated promoters are described below, including two embodiments of the tomato E8 promoter, the tomato E4 promoter and the raspberry E4 promoter. Further useful promoters include, but are not limited to, the avocado cellulase promoter (Cass, et al.), the tomato polygalacturonase promoter (Bird, et al.), and the tomato ACC oxidase (ACCO) promoter, as well as promoters from homologous genes obtained from other plants.

Exemplary gene products that result in reduction of ethylene synthesis include, but are not limited to the following: S-adenosylmethionine hydrolase; 1-aminocyclopropane-1-carboxylate deaminase (Klee, et al.; Sheehy, et al.); the ACC synthase gene in an antisense or cosuppression configuration (Oeller, et al.; Van der Straeten, et al.); and the ACC oxidase gene in either an antisense or cosuppression configuration (Hamilton, et al.; Holdsworth, et al.). Cosuppression has been described by Jorgensen, et al. (1991, 1993), both herein incorporated by reference.

Other gene products that may be useful in the reduction of ethylene biosynthesis include catalytic antibodies and ribozyme molecules.

The present invention provides, in one aspect, nucleic acid constructs suitable for transforming plants with heterologous genes under the control of an E4 promoter (originally isolated from tomato; Cordes, et al.) or an E8 promoter. In one embodiment, the plant is a fruit-bearing plant, and the heterologous gene is a gene effective to reduce ethylene biosynthesis in fruit from the plant. In another embodiment, the plant is a flowering plant, and the heterologous gene is a gene effective to reduce ethylene biosynthesis in flowers of the plant. In still another embodiment, the plant is a vegetable, and the heterologous gene is a gene effective to reduce ethylene biosynthesis in the vegetable.

Experiments performed in support of the present invention demonstrate that an exemplary heterologous gene effective to reduce ethylene biosynthesis in tissues of a plant is the AdoMetase gene, isolated from bacteriophage T3 (Hughes, et al., 1987a). These experiments show that ethylene production in ripe transgenic tomatoes containing the AdoMetase gene under the control of a tissue/stage specific promoter is significantly lower.

In addition, the tomatoes develop color to a light red stage and then cease further color development, and remain firm longer than control tomatoes. Further, the experiments show that the E4 promoter coupled to a heterologous gene can be activated by wounding plant tissue containing the construct, and that the activation of the promoter is typically transient in nature.

A. Tomato E4 Promoter

The tomato E4 promoter is both stage and tissue specific (Cordes, et al.). Typically, E4 mRNA is abundant in ripening fruit and is not detected in leaf, root, stem, or unripe fruit. E4 gene expression can, however, be activated by ethylene, and the ethylene-induced expression can be detected in a variety of plant tissues (Lincoln, et al., Lincoln and Fischer). Further, the rin (ripening inhibited) mutation, that blocks many aspects of ripening, including softening, ethylene production, and color development (Giovannoni, et al.), reduces the concentration of E4 mRNA by greater than 10-fold. The sequence of the E4 promoter has been published (Cordes, et al.) and the DNA sequence of the minus 1173 base pair region is presented FIGS. 25A and 25B.

The tomato E4 promoter may be employed in vector constructs used to produce transgenic plants, such as transgenic tomatoes. For example, a vector engineered according to methods of the present invention (detailed below), containing the tomato E4 promoter connected to the AdoMetase gene (e.g. vector pAG-5520), may be used to produce transgenic raspberries, strawberries, melons, carnations, cauliflower, and the like. The AdoMetase gene will be expressed in the fruit of these transgenic plants will delay ripening. An advantage of this method is a savings of time and resources involved in vector construction, since the same vector can be used to transform many different plant types. Experiments performed in support of the present invention have demonstrated the ability to the tomato E4 promoter to facilitate DNA coding sequence expression in raspberries.

Alternatively, E4 promoter sequences may be isolated from the same type of plant that is to be transformed, and incorporated into the vector constructs used to perform the transformations. For example, a raspberry E4 promoter may be connected to a heterologous gene, such as the AdoMetase gene, and used to transform raspberries. This method is typically preferable, because a promoter from the same type of plant as is transformed is more likely to contain all of the regulatory elements required for appropriate stage and tissue specificity of expression. For example, isolation of a genomic copy of a raspberry E4 gene with 5' regulatory sequences is described below. E4 promoters may be isolated from other plants using a number of methods, including those described below.

B. Identification of Plant E4 Promoters

The present invention provides for the use E4 promoters from species other than tomato in vector constructs containing heterologous genes. Southern blot experiments performed in support of the present invention demonstrate the presence of DNA molecules having high sequence homology with the tomato E4 gene in raspberry, strawberry, melon, carnation and cauliflower. Similar Southern blot analyses may be performed on other fruit-bearing plants to identify additional E4 genes.

A Southern blot analysis used herein is detailed in Example 6. E4 homologues are identified in a Southern blot of the genomic DNA of the plants listed above probed with a labelled DNA fragment containing the coding sequence of the tomato E4 gene.

The probe is selected to contain the coding sequence of tomato E4, rather than the promoter sequence, because coding sequences are typically more conserved from species to species than are promoter sequences. In the experiments detailed in Example 6, probe molecules are generated from tomato genomic DNA using primer-specific amplification (Mullis; Mullis, et al.). The oligonucleotide primers are selected such that the amplified region included the entire coding sequence of the tomato E4 gene. Primers may also be selected to amplify only a selected region of the E4 gene.

Alternatively, a probe can be made by isolating restriction-digest fragments containing the sequence of interest from plasmid DNA.

The probe is labeled with a detectable moiety to enable subsequent identification of homologous target molecules. Exemplary labeling moieties include radioactive nucleotides, such as $^{32}$P-labeled nucleotides, digoxygenin-labeled nucleotides, biotinylated nucleotides, and the like, available from commercial sources.

In the case of primer-amplified probe, labeled nucleotides may be directly incorporated into the probe during the amplification process. Probe molecules derived from DNA that has already been isolated, such as restriction-digest fragments from plasmid DNA, are typically end-labeled (Ausubel, et al.).

Target molecules, such as HindIII DNA fragments from the genomes of the above-listed plants, are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules.

Conditions favoring specific hybridization are referred to as moderately to highly stringent, and are affected primarily by the salt concentration and temperature of the wash buffer (Ausubel, et al., Sambrook, et al.). Conditions such as those used in the final wash in Example 6 are typically classified as moderately stringent, due to the low salt concentration, and are expected to preserve only specific hybridization interactions, allowing the identification and isolation of homologous genes in different plant species.

Following contacting, hybridization, and washing, target molecules with sequences homologous to the probe are identified by detecting the label on the probe. The label may be detected directly, for example, as in radioactive label detected on autoradiograms, or it may be detected with a secondary moiety, for example, fluorescently-labeled streptavidin binding to a biotinylated probe.

C. Isolation of Other E4 Promoters

Following the identification of plants containing E4 genes, the DNA encoding the genes, including the promoter regions, may be isolated from the respective species, by, for example, screening a genomic DNA library. Experiments performed in support of the present invention, detailed in Example 7, demonstrate the isolation of a genomic copy of a raspberry E4 gene from a raspberry genomic DNA library.

The library of interest is screened with a probe containing sequences corresponding to the coding sequence of a known E4 gene, such as the tomato E4 gene. The screening is done using known methods (Ausubel, et al., Sambrook, et al.), essentially as described above.

Positive plaques or colonies are isolated, and the insert DNA is sequenced and compared to known E4 sequences. Clones containing inserts with sequences corresponding to genes homologous to tomato E4 are identified and, if necessary, used to obtain additional clones until the promoter region of interest is isolated. The sequence of the raspberry E4 gene is presented in FIGS. 15A to 15E (SEQ ID NO: 26).

III. Heterologous Genes

According to methods of the present invention, heterologous genes are linked to the promoters of the present invention. Exemplary heterologous gene for the transformation of plants include genes whose products are effective to reduce ethylene biosynthesis in specific tissues of those plants, e.g. the fruits, flowers or leaves. One of these genes, AdoMetase, is discussed in detail below.

A. Ethylene Synthesis

The amino acid methionine has been shown to be a precursor of ethylene ($C_2H_4$) in plant tissues (reviewed by Imaseki). Methionine, however, is not the immediate precursor but first must be converted to the sulfonium compound S-adenosylmethionine (SAM) and, subsequently, aminocyclopropane-1-carboxylic acid (ACC) prior to conversion to ethylene. The metabolic reactions for the synthesis of ethylene from methionine under both normal and stress conditions are presented in FIG. 1A, and summarized as follows:

Methionine→SAM→ACC→Ethylene

ACC synthase catalyzes the degradation of SAM to ACC and 5'-methylthioadenosine (MTA). This enzymatic reaction appears to be the rate limiting step in ethylene formation. For example, the natural plant hormone indoleacetic acid (IAA or auxin) stimulates ethylene production by inducing the synthesis of ACC synthase. Conversely, the synthesis of SAM from methionine and the production of ethylene from ACC do not require auxin induction.

In addition, wounding and fruit ripening induces the formation of ACC synthase and, therefore, the conversion of SAM to ACC. The other product of the ACC synthase reaction, MTA, must be recycled back into methionine so as to provide an adequate supply of methionine for continual ethylene production. This recycling pathway from MTA to methionine, also presented in FIG. 1A, has been shown to exist in plant tissue (Adams, et al.; Kushad, et al.). The degradation of MTA has added significance in light of the finding that MTA is a potent inhibitor of ACC synthase. The importance of the degradation and recycling of MTA in normal plant tissues is, therefore, twofold: 1) to prevent the direct inhibition of ethylene synthesis by MTA, and 2) to provide adequate methionine for continual ethylene synthesis.

The first step in the degradation of MTA in plant tissue is the hydrolysis of this nucleoside to 5-methylthioribose (MTR) by a specific MTA nucleosidase. MTR not only provides its methylthio moiety for the formation of methionine, but also contributes four carbons from its ribose towards the synthesis of this amino acid. Therefore, the methylthio group is conserved by recycling. It should be noted that this pathway merely maintains a methionine supply for ethylene biosynthesis, but does not result in a net increase in methionine synthesis.

1. AdoMet hydrolase

One approach to reduce ethylene biosynthesis in plants reported here utilizes a gene that encodes the enzyme S-adenosylmethionine hydrolase. This approach has been described in allowed, co-owned, co-pending, U.S. patent application Ser. No. 08/255,833, filed 8 Jun. 1994. This enzyme, encoded by the *E. coli* bacteriophage T3, hydrolyses AdoMet to homoserine and MTA. The enzyme is known as its recommended name, AdoMet hydrolase (AdoMetase), or by its other name, S-adenosylmethionine cleaving enzyme (SAMase) (Studier, et al.). Both products of the reaction (i.e., homoserine and MTA) are recycled to methionine; MTA as previously shown (FIG. 1A) and homoserine via a metabolism pathway known to exist in plant tissues.

The AdoMetase gene has been identified, isolated, cloned, and sequenced (Hughes, et al., 1987a; Hughes, et al., 1987b). The gene contains two in-frame reading sequences that specify polypeptides of 17105 and 13978 daltons. Both polypeptides terminate at the same ochre codon. This results in the 14 kd polypeptide being identical to 82% of the 17 kd polypeptide starting at the carboxyl end of the longer polypeptide. Both polypeptides are present in partially purified cells and from *E. coli* expressing the cloned gene (Hughes, et al., 1987b; Studier, et al., 1976). Other bacteriophages that encode the AdoMetase or SAMase genes are coliphage BA14, Klebsiella phage K11, and Serratia phage IV (Mertens, et al.; Horsten, et al.).

Figure 1B:
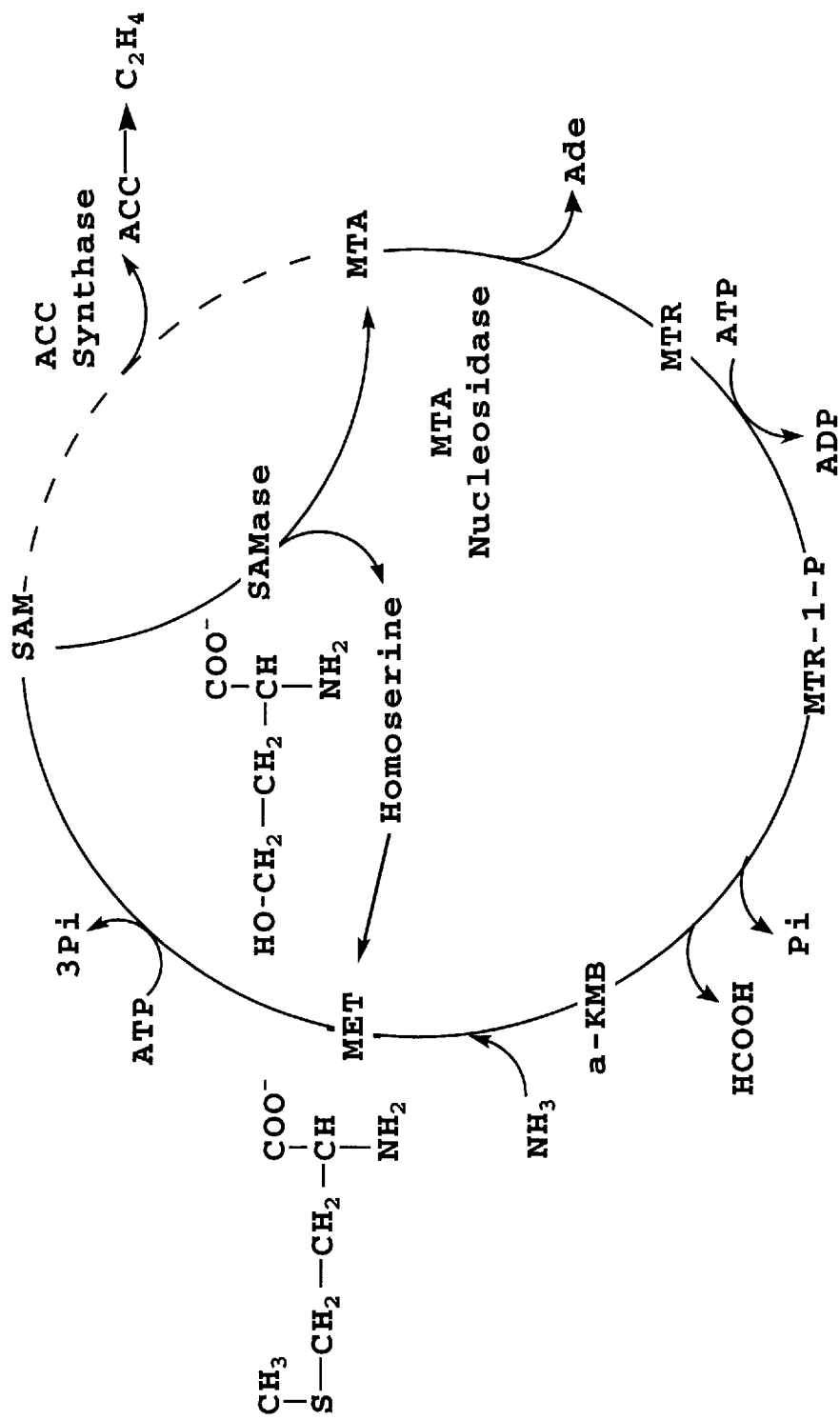
FIG. 1B schematically illustrates the effect of the enzyme SAMase (AdoMetase) on ethylene biosynthesis.

The effect AdoMetase expression in plant cells has on the plant methionine recycling pathway is shown schematically in FIG. 1B. Experiments performed in support of the present invention, using transgenic tomatoes expressing an AdoMetase gene and monitoring ethylene production, have demonstrated that the effect of AdoMetase on the pathway is to "short circuit" the branch that produces ethylene: ethylene production is reduced in such transgenic plants.

Different bacteriophages may be expected to contain AdoMetase genes with variations in their DNA sequences.

The isolation of AdoMetase coding sequences from bacteriophage coding sequences can be accomplished as previously described for AdoMetase from bacteriophage T3. Alternatively, degenerative hybridization probes for AdoMetase coding sequences can be generated and used to screen plasmids carrying fragments of a selected bacteriophage's genome for the presence of homologous sequences. AdoMetase enzymatic activity can be evaluated by standard biochemical tests (see for example, Example 13).

Furthermore, the amino acid sequence of AdoMetase may be modified by genetic techniques to produce enzymes with altered biological activities (see below). An increase in the biological activity could permit the use of lower amounts of the enzyme to control ethylene biosynthesis in plants.

IV. Vector Construction

Plant transformation vectors are constructed according to methods known in the art (see, for example, Houck, et al., and Becker, et al.)

Figure 2:
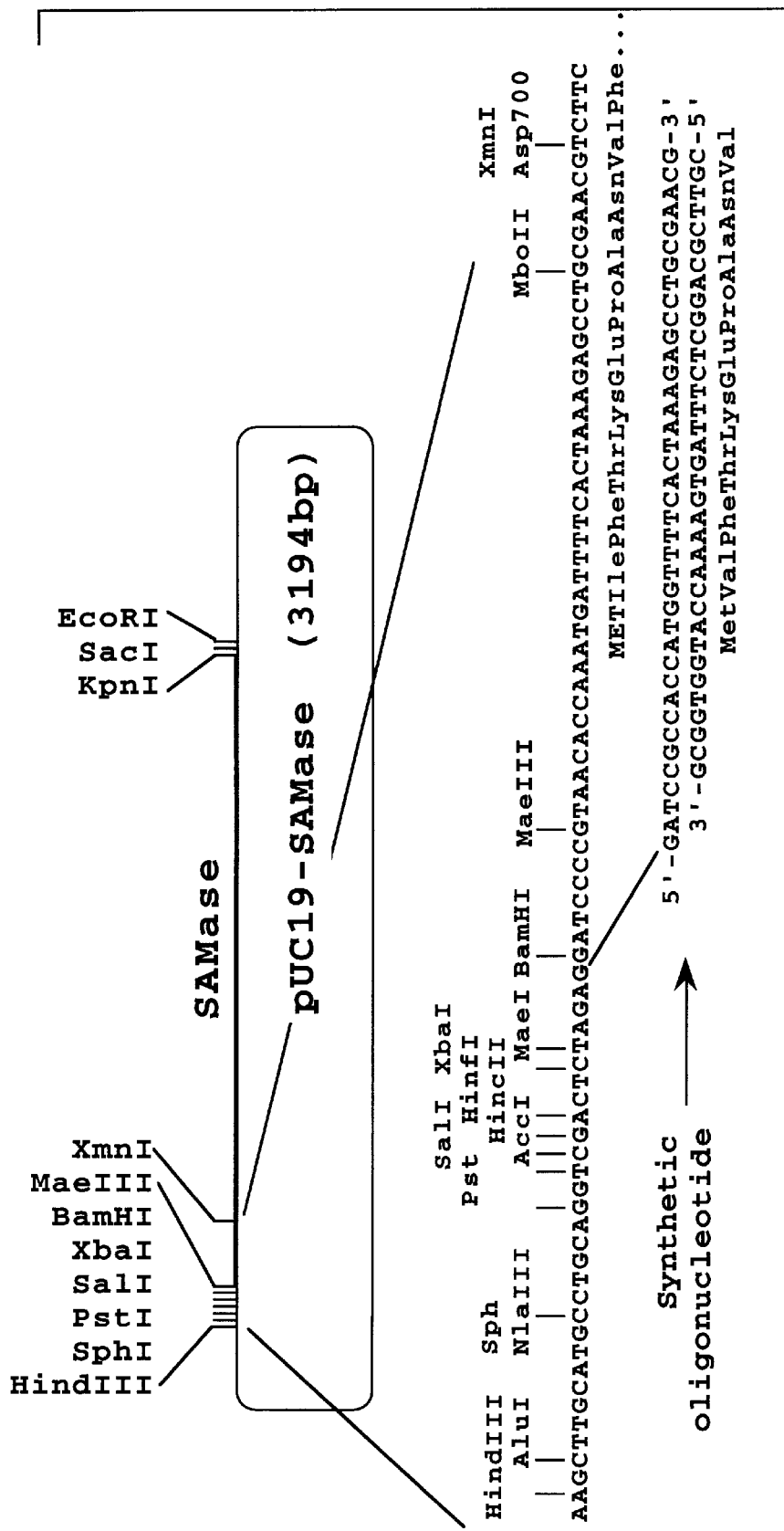
FIG. 2 schematically illustrates the steps described for the genetic engineering of the AdoMetase-encoding gene in vector pAG-111.

A series of recombinant DNA manipulations are performed in the AdoMetase gene prior to placement in an Agrobacterium expression vector. Initially, a MaeIII to BamHI fragment from M13HB1 (Hughes, et al., 1987a) is subcloned into the pUC19 plasmid vector to produce pAG-110 (Example 1, pUC19-SAMase FIG. 2). To increase the translational efficiency of the AdoMetase gene in plants, site directed mutagenesis of the nucleic acid sequences surrounding the ATG start codon is performed. A synthetic double stranded 39 base pair oligonucleotide is synthesized and substituted for the BamHI to XmnI fragment at the 5' end of the gene (FIG. 2). The net effect of this substitution is to change the CACCAAATGA (SEQ ID NO: 14) in the native T3 sequence to GCCACCATGG (SEQ ID NO: 15) which is an optimal eukaryotic translational initiation sequence (Kozak, et al.; Lutcke, et al.).

The change also introduces an NcoI site (CCATGG) at the AdoMetase start codon which facilitates fusions to different promoters. The only alteration to the AdoMetase coding sequence is the amino acid at amino acid position two which is changed from isoleucine to valine: this is a highly conservative amino acid change. The altered form of AdoMetase was named SAM-K (FIGS. 11A to 11D).

A recombinant vaccinia vector with SAM-K (vv:SAM-K) was constructed. Expression of this vector in African green monkey cells or T3-infected bacterial cells was compared with the gene to the native T3 gene when expressed in the same cells. The specific activity of AdoMetase was higher in the vv:SAM-K infected cells than in the T3 infected bacterial cells demonstrating that SAM-K encodes a fully functional version of AdoMetase.

Experiments performed in support of the present invention have demonstrated constitutive expression of AdoMetase in transgenic plants. In these plants there is a significant reduction in the ability of these plants to synthesize ethylene.

Figure 17A:
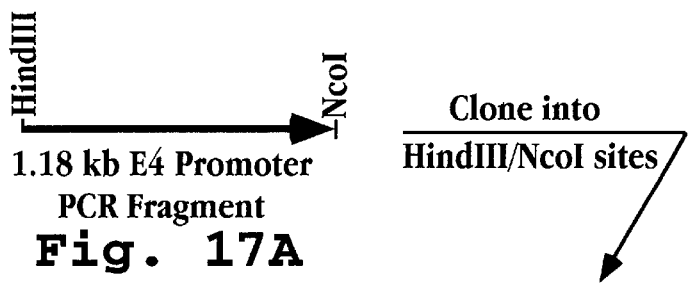
FIGS. 17A–D show a diagram of the steps followed in constructing vectors pAG-111 (FIGS. 17A–17B), pAG-117 (FIGS. 17B–17C) and pAG-5520 (FIGS. 17C–17D).
Figure 17B:
Figure 17C:
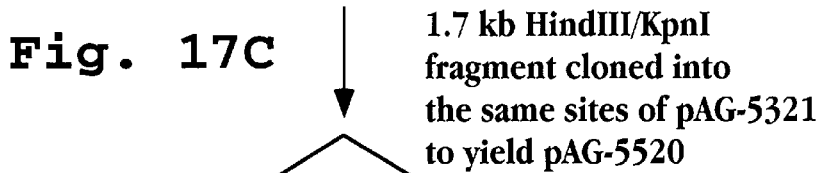

Using the sequence shown in FIG. 24 primers are prepared for use in the polymerase chain reaction (PCR) to amplify a 1177 base pair region of the E4 promoter from tomato genomic DNA (Example 8). The primers are designed with unique restriction sites at each end and were used to place the promoter in the proper orientation 5' of the SAMase gene in pAG-111 (FIGS. 17A, 17B). The 5' end of the promoter fragment has a HindIII site, while the 3' end has an NcoI site (CCATGG) placed such that the ATG start codon of the E8 gene product is used as the ATG in the NcoI site. This allows precise placement of the entire E4 promoter directly in front of the SAMase amino acid coding sequences with no intervening sequences (Example 8).

A selectable vector expressing AdoMetase under the control of the E4 promoter (pAG-5520) is constructed as detailed in Example 8 and schematized in FIGS. 17A–17D. For selection, the vector contains the neomycin phosphotransferase II gene, providing aminoglycoside antibiotic (e.g. kanamycin) resistance.

V. Plant Transformation

A. Methods of Transforming Plants pAG-5520 is transferred to tomato plants (Example 9) to generate transgenic plants expressing AdoMetase. Tomato progenitor cells (tomato cotyledon tissue explants) are transformed with EHA101 bacteria containing pAG-5520 and grown in tissue culture in the presence of kanamycin for 8 to 10 weeks to produce plants.

A number of methods, in addition to Agrobacterium-based methods, may be employed to elicit transformation of plant progenitor cells, such as electroporation, microinjection, and microprojectile bombardment. These methods are well known in the art (Comai, et al., Klein, et al.; Miki, et al.; Bellini, et al.) and provide the means to introduce selected DNA into plant genomes: such DNA may include a DNA cassette which consists of the E4 gene promoter functionally adjacent, for example, AdoMetase coding sequences.

B. Identifying and Evaluating Transformants

Several transgenic plants are assayed for their ability to synthesize AdoMetase mRNA, AdoMetase protein, and their ability to inhibit the biosynthesis of ethylene. The assays are performed after the plant tissue being assayed has been subjected to a wound, and are carried out both on leaves of the plant, as well as the fruit. Leaf wounds are typically cuts on the leaf, performed either with a dull knife or with a circular bore. Fruit "wounds" can be as mild as picking the fruit from the plant.

Leaf-based assays can be informative if the promoter driving the heterologous gene (transgene) is at least somewhat active in leaf tissue, as is the case for the E4 promoter. In such cases, leaf-based assays are useful for initial screens of the expression level of a transgene, since they can be performed much earlier than fruit-based assays. Fruit-based assays, on the other hand, provide more accurate data on transgene expression in the target tissue itself (fruit). The results of both types of assays are detailed in Example 13.

Figure 18A:
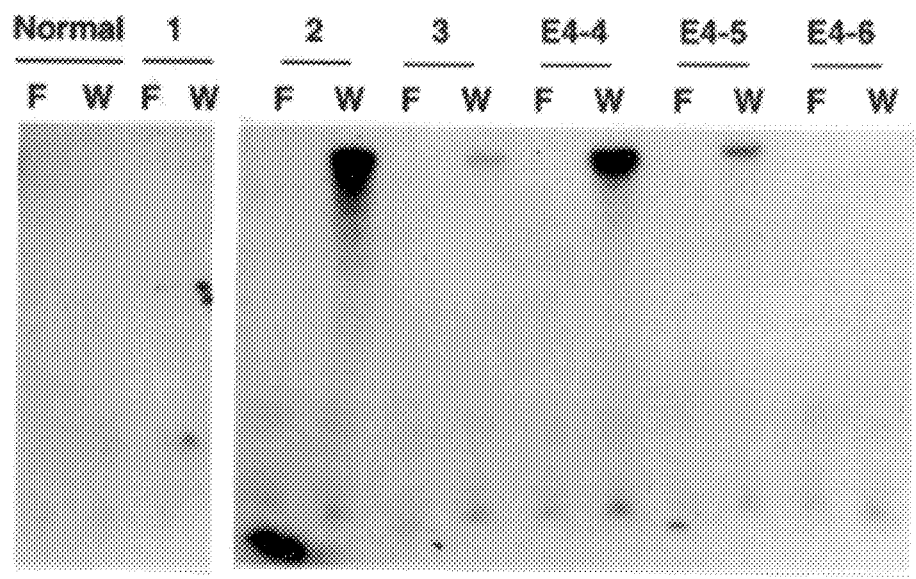
FIGS. 18A and 18B show the results of an RNAse protection assay to detect SAMase mRNA in fresh and wounded leaves of normal and E4/SAMase transgenic tomato plants.
Figure 18B:
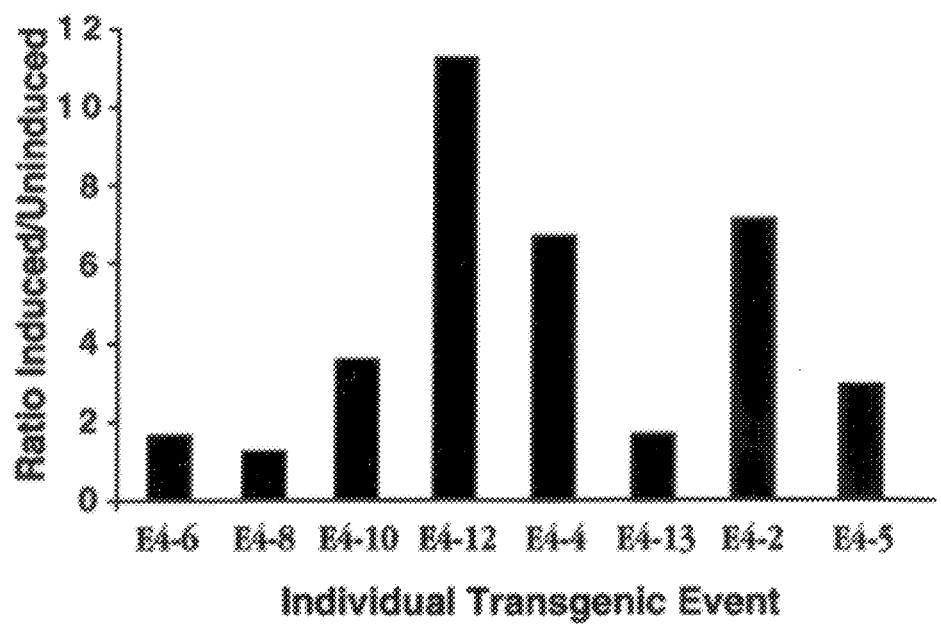
Figure 20:
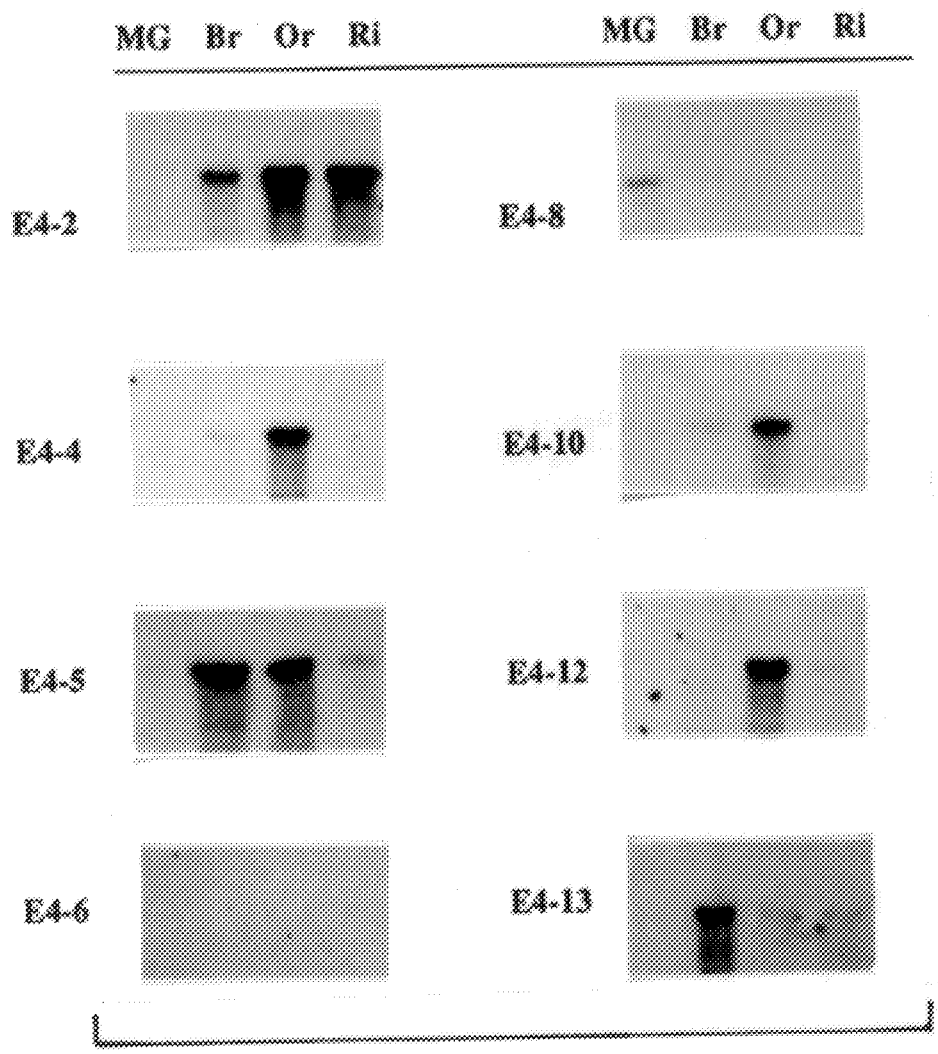
FIGS. 20 and 21 show the results of an RNAse protection assay to detect SAMase mRNA in E4/SAMase transgenic tomato ripening fruit at four stages of ripening.
Figure 21:
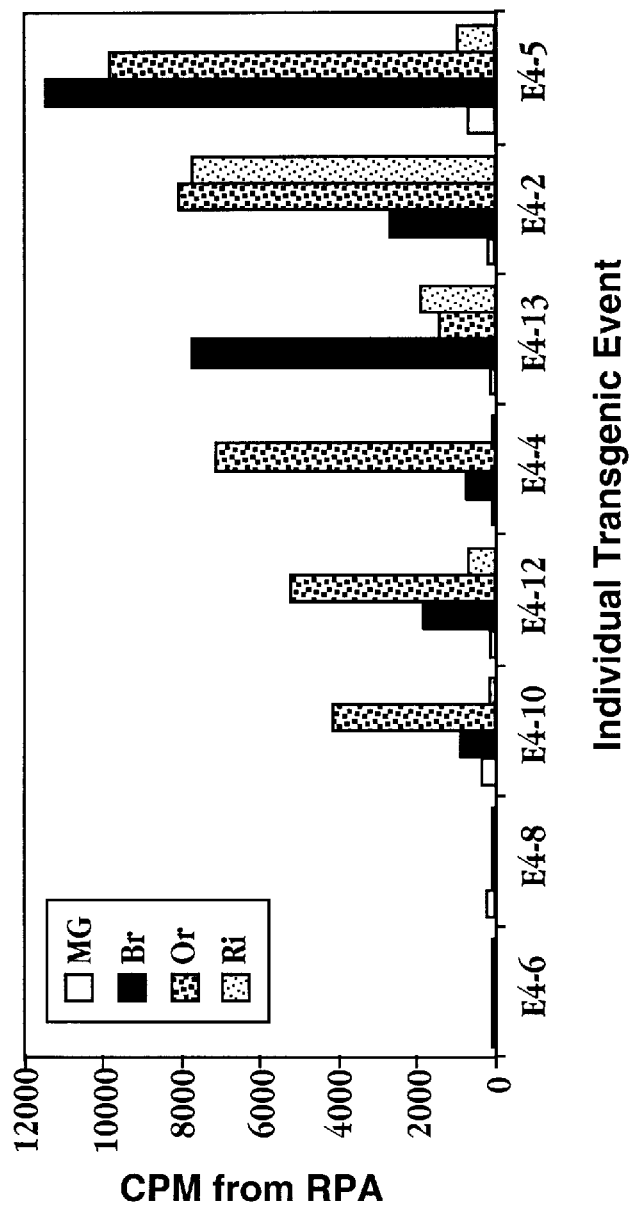

AdoMetase mRNA levels are determined using, for example, an RNAase protection assay (RPA) (Example 10). FIGS. 18A and 18B show the results of an RPA using fresh or wounded leaves from normal and transformed tomato plants. Plants showing detectable transgene mRNA expression in leaves are grown to produce fruit, and the fruit is then tested mRNA expression. FIGS. 20 and 21 shows the results of an RPA using the fruit from one transgenic plant at different stages of fruit ripening. While the absolute level of expression varies considerably among different transformed lines, the relative level of expression as a function of ripening stage is consistently transient, typically peaking at the orange stage, with expression at low levels in fully ripe fruit in all but one case.

Figure 19:
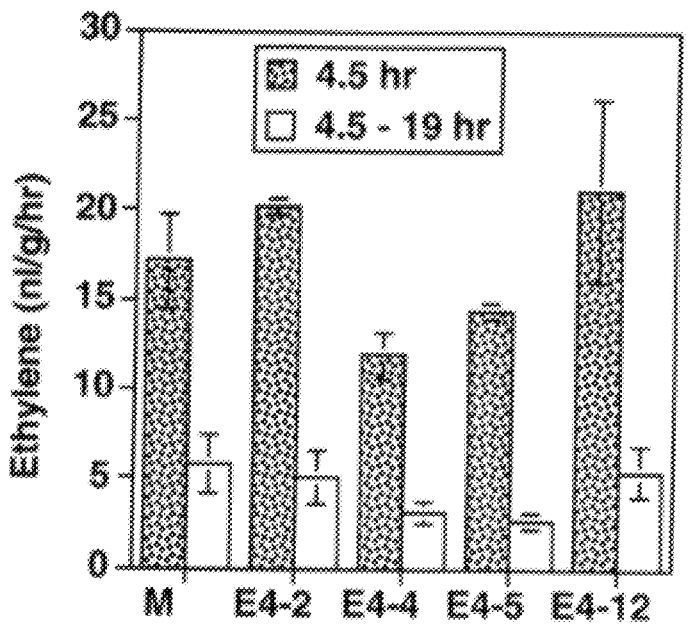
FIG. 19 shows a bar graph of ethylene production in wounded leaves of normal and E4/SAMase transgenic tomato plants.

Ethylene biosynthesis is measured in leaves and fruit of transgenic tomatoes. FIG. 19 shows the level of ethylene synthesis in wounded leaves from normal (M) and four transgenic tomato plants. The experiments are performed as detailed in Example 11. Some of lines show a reduction in ethylene biosynthesis, but the values are not well correlated with those obtained in the RNAse assay presented in FIGS. 18A and 18B. The assay is nevertheless useful for screening, as suggested above, since plants negative for AdoMetase expression in leaf wound assays are also negative for AdoMetase expression in fruit.

Figure 23:
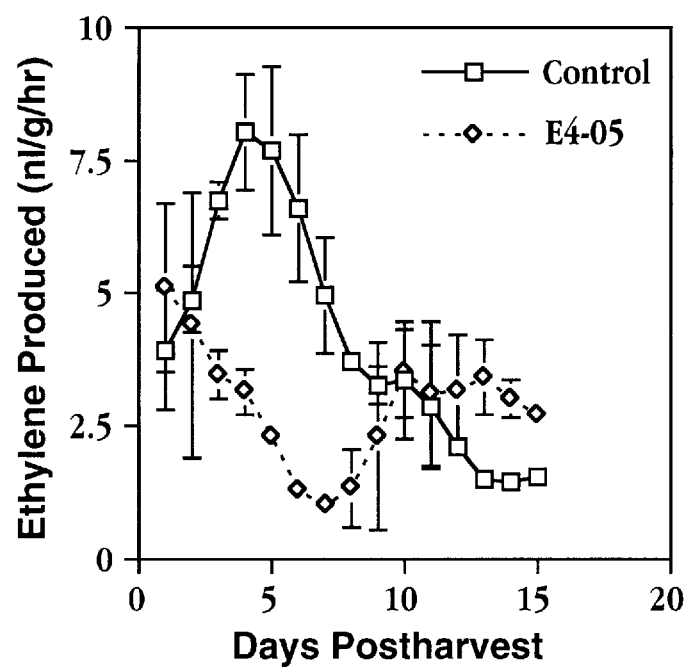
FIG. 23 shows a chart of ethylene production in normal and E4/SAMase transgenic tomatoes as a function of time after harvest.

Ethylene biosynthesis in transgenic fruit, is typically reduced relative to control fruit, as is shown in FIG. 23. Whereas control tomatoes show an increasing rate of ethylene synthesis during the 5 days following harvest, fruit from transgenic line E4-05 shows a decreasing rate of synthesis, which bottoms out approximately one week postharvest. This result demonstrates that constructs of the present invention are effective at reducing the level of ethylene biosynthesis in the fruit of fruit-bearing plants.

After these time-points, the rates of ethylene synthesis reverse directions for both normal and transgenic plants. This characteristic demonstrates the physiological effects of the transient nature of heterologous gene expression under control of an E4 promoter, and that activation of the E4 promoter, for example, by wounding, can transiently inhibit ethylene biosynthesis.

Figure 22:
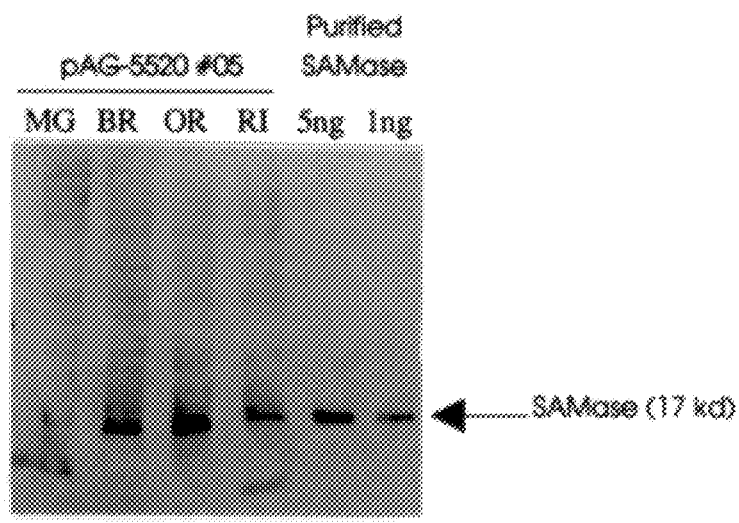
FIG. 22 shows the results of a Western blot, of E4/SAMase transgenic tomatoes at four stages of ripening, probed with an antibody to SAMase.

To correlate the effects of AdoMetase mRNA expression, Western Blots were performed, as detailed in Examples 12 and 13. The results are shown in FIG. 22. These results demonstrate that transformation of tomato progenitor cells with a construct containing the E4 promoter coupled to the AdoMetase gene is effective to reduce ethylene biosynthesis in the fruit of the transgenic plants, and further, that this reduction can have a transient time-course.

The biological effects of AdoMetase gene expression include a cessation of color development beyond the light red stage, and tomatoes that remain firm much longer than untransformed controls.

VI. E8 Promoter Regulated Gene Expression.

Regulatable promoters have been employed in the method of the present invention. One exemplary regulatable promoter is the tomato E8 gene promoter. Expression of the E8 gene SEQ ID NO: 27 has been shown to be induced (i) at the onset of ripening, and (ii) by treatment of tomatoes with ethylene (Deikman, et al., 1988; Lincoln, et al.; Giovannoni, et al.). The sequence of the E8 promoter has been published (Deikman, et al., 1988; Deikman, et al., 1992) and the DNA sequence of the minus 2216 base pair region is presented in FIGS. 13A and 13B.

Figure 3:
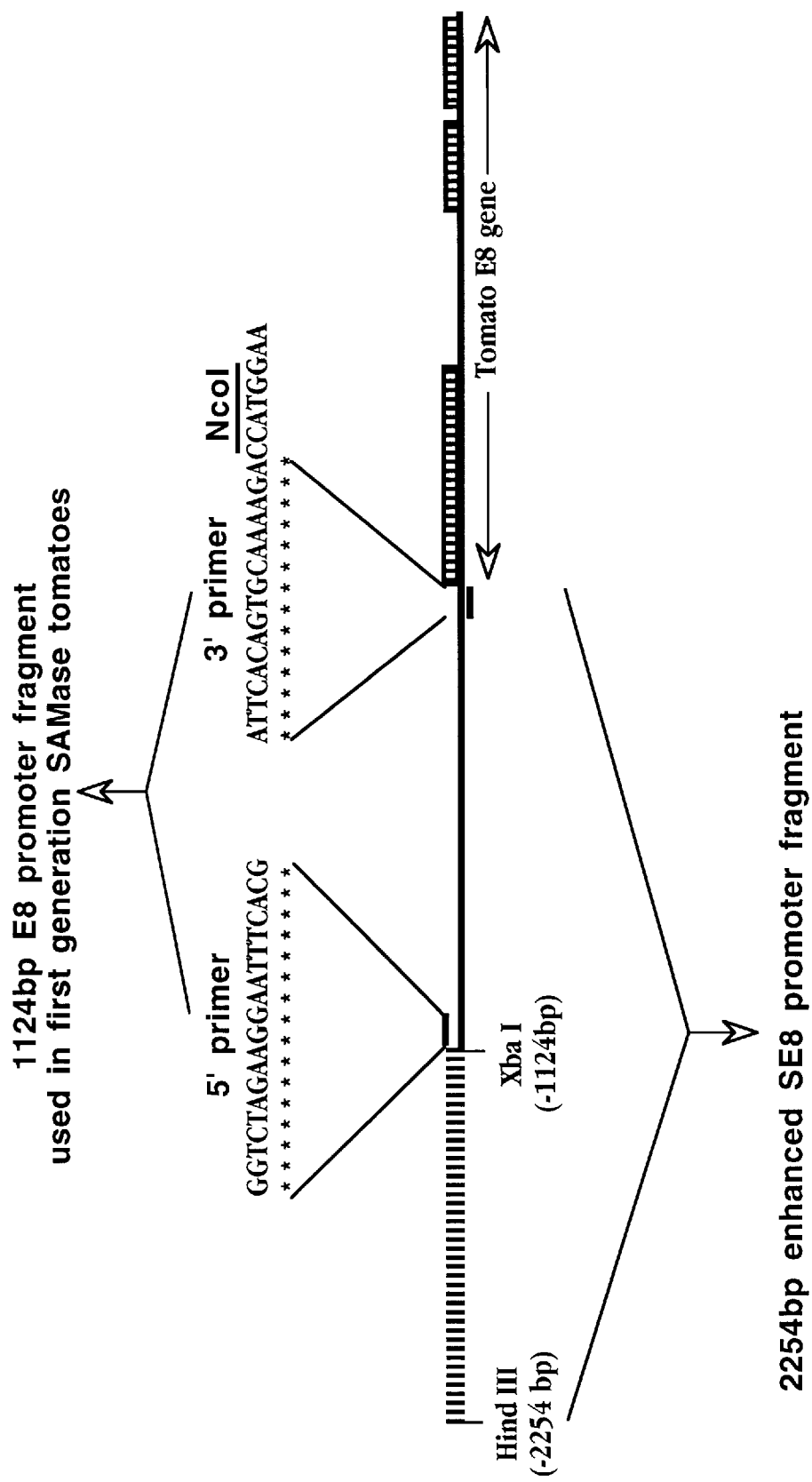
FIG. 3 illustrates the elements of the tomato E8 promoter and the primers used to amplify and isolate the promoter sequences.

Using the sequence shown in FIGS. 13A and 13B, primers were prepared for use in the polymerase chain reaction (PCR) to amplify the 1124 base pair promoter from tomato genomic DNA (Example 1). The primers were designed with unique restriction sites at each end and were used to place the promoter in the proper orientation 5' of the SAM-K gene in pUC19 (FIG. 3). The 3' end of the promoter fragment had an NcoI site (CCATGG) placed such that the ATG start codon of the E8 gene product was used as the ATG in the NcoI site. This allowed precise placement of the entire E8 promoter directly in front of the SAM-K amino acid coding sequences with no intervening sequences (Example 1, FIG. 12A).

Figure 4:
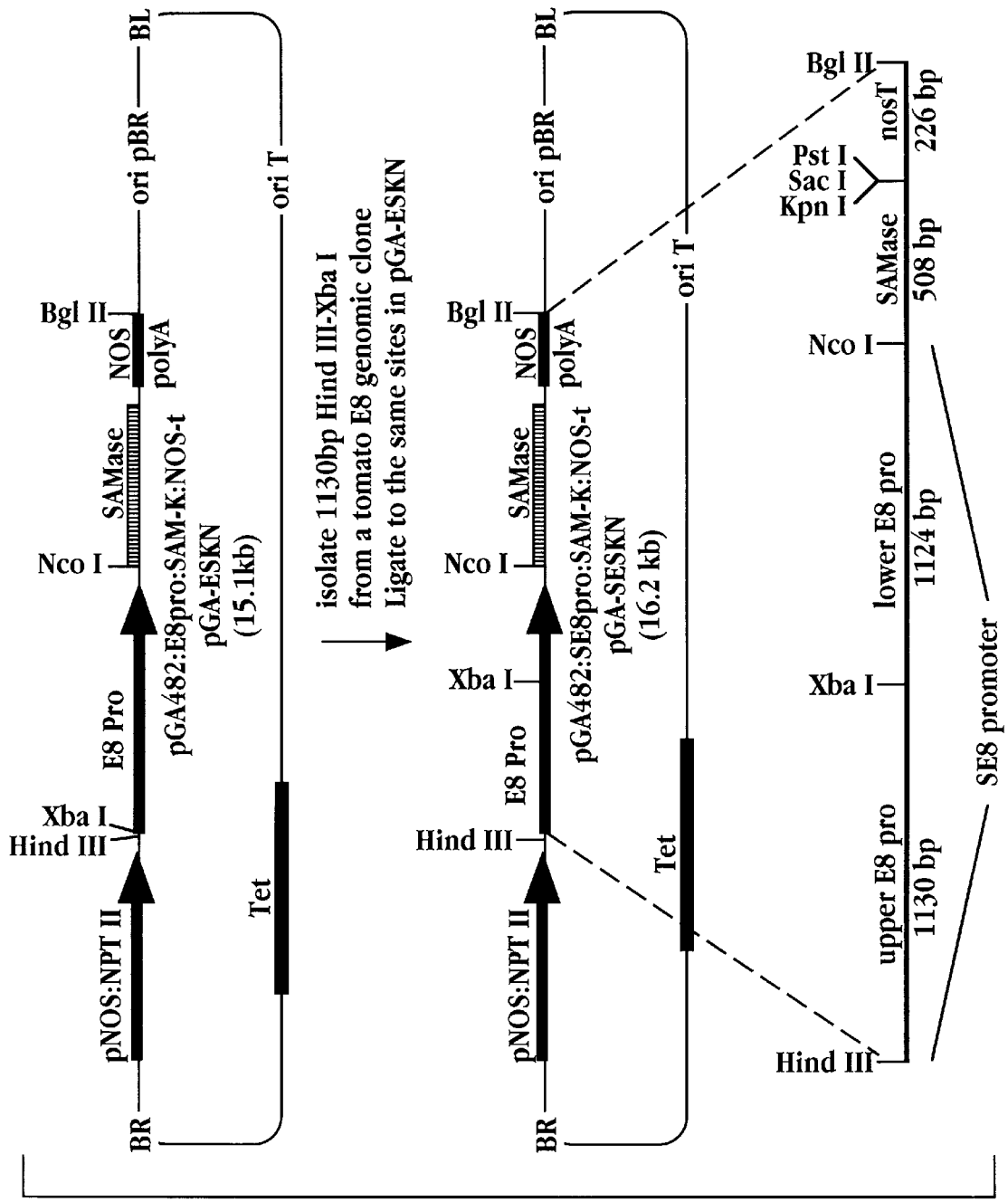
FIG. 4 outlines the steps involved in the construction of pGA-SESKN from pGA-ESKN and shows the elements of the E8 gene adjacent the AdoMetase (SAMase) coding sequences which are followed by nosT transcription termination sequences.
Figure 5A:
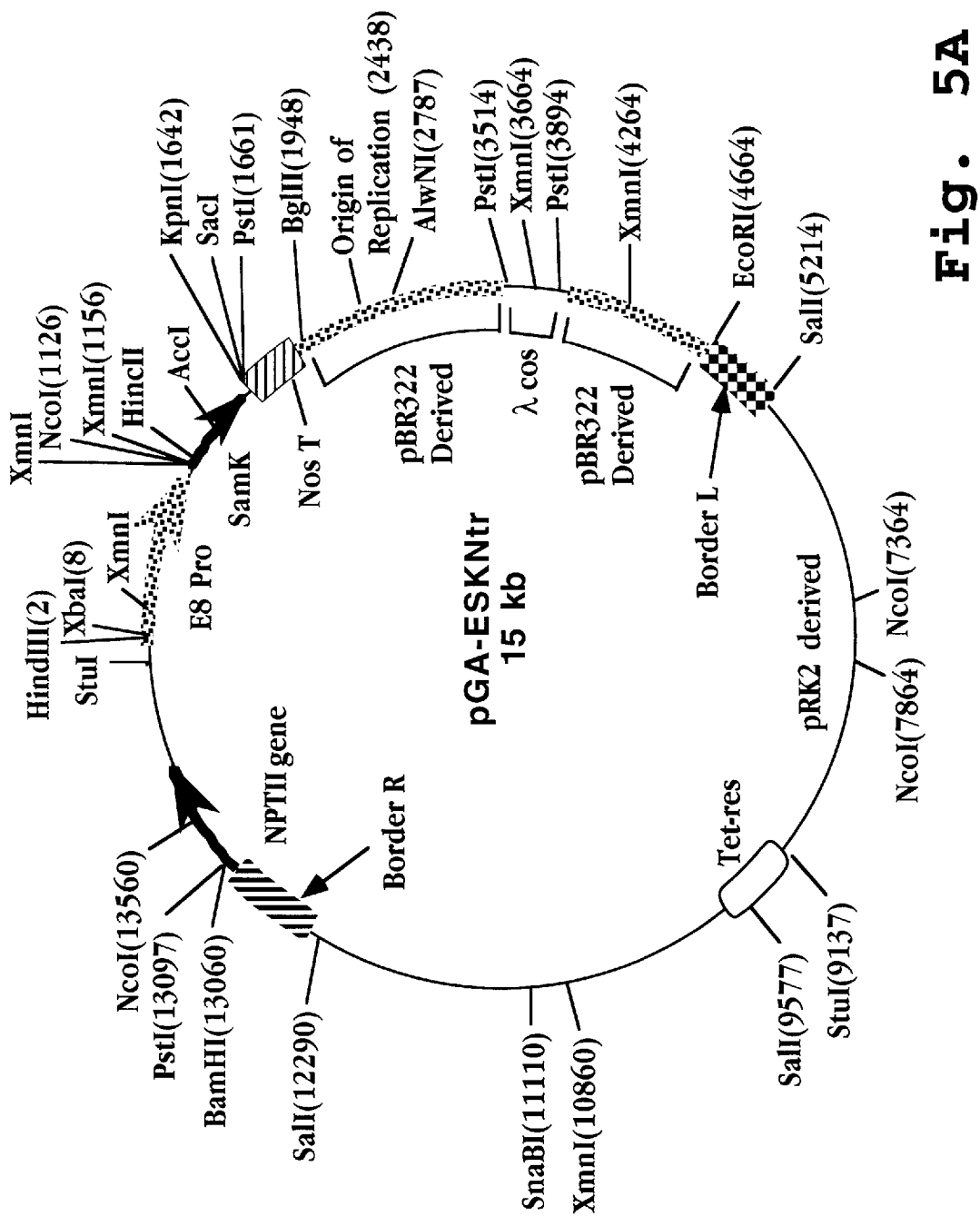
FIG. 5A schematically represents the structure of the pGA-ESKN vector.
Figure 5B:
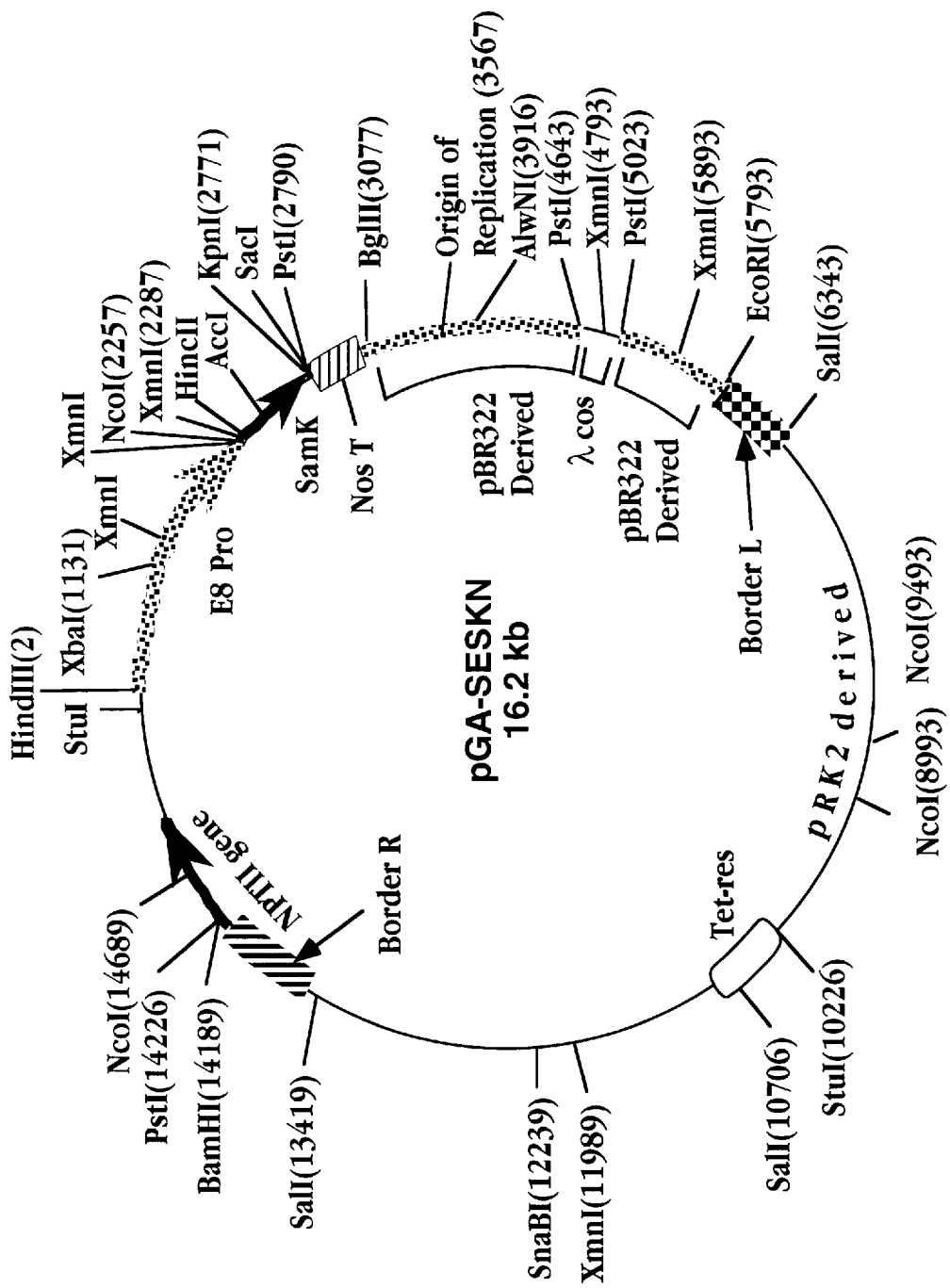
FIG. 5B schematically represents the structure of the pGA-SESKN vector.

Two AdoMetase expressing vectors were constructed (Example 1), the pAG-5321 (pGA-ESKN) vector (FIGS. 12A to 12C and FIG. 5A) and the pGA-SESKN vector (FIG. 4 and FIG. 5B). The pAG-5321 vector contains a portion of the E8 promoter (FIG. 4, lower E8 promoter) adjacent the AdoMetase coding sequences. A lambda EMBL-3 clone containing genomic tomato sequences that hybridize to the −1124 E8 region was isolated and used as the source for a region upstream of the −1124 E8 (lower E8) promoter. Restriction mapping analysis and subcloning allowed identification of an approximately 1200 bp HindIII to XbaI fragment as the region immediately upstream of the original −1124 bp E8 promoter (FIG. 4). This region was added to the pAG-5321 construct to yield pGA-SESKN, which contained the approximately −2254 bp E8 promoter fused to the AdoMetase gene (FIG. 4, SE8).

Both of these vectors were transferred to tomato plants (Example 2) to generate transgenic plants expressing AdoMetase. A number of methods, in addition to Agrobacterium-based methods, may be employed to elicit transformation of the plant host, such as electroporation, microinjection, and microprojectile bombardment. These methods are well known in the art (Klein, et al.; Miki, et al.; Bellini, et al.). Further, these methods provide the means to introduce selected DNA into plant genomes: such DNA may include a DNA cassette which consisting of the E8 gene promoter functionally adjacent AdoMetase coding sequences.

Figure 6:
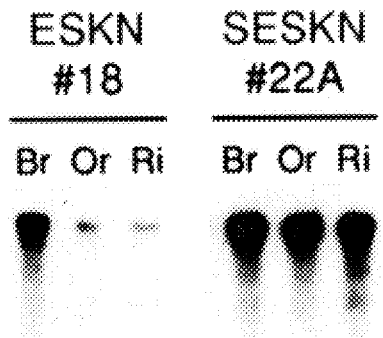
FIG. 6 is a photograph of an autoradiogram which demonstrates the AdoMetase mRNA levels in fruit derived from two different transgenic plants.
Figure 7:
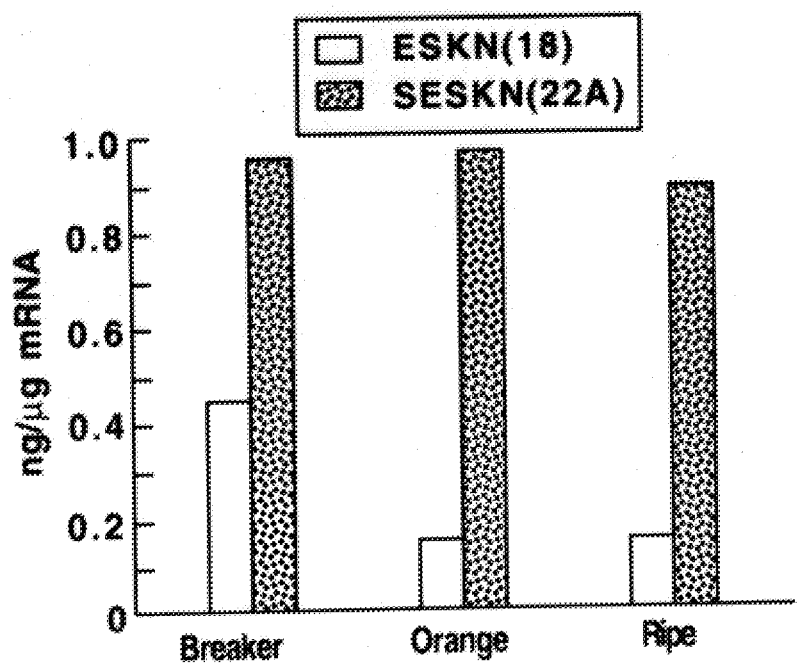
FIG. 7 shows a quantitation of the results presented in FIG. 6. These results illustrate the effect of variations of the E8 promoter on AdoMetase mRNA levels in ripening tomatoes.

Several transgenic plants were assayed for their ability to synthesize AdoMetase mRNA using a sensitive RNAase protection assay (RPA) (Example 3). FIGS. 6 and 7 show the results of an RPA using the fruit from two transgenic plants (ESKN, transformed with pAG-5321, and SESKN, transformed with pGA-SESKN) at different stages of fruit ripening. Other tissues from these plants including immature and mature leaves, flowers and stems were negative for the presence of AdoMetase RNA. Although the expression of AdoMetase in ESKN transgenic plants was regulated to the post mature green fruit, it was repeatedly observed (as shown in FIGS. 6 and 7) that the expression of AdoMetase turned off in the fully ripe fruit. On the other hand, the SESKN transgenic fruit maintained AdoMetase mRNA expression in ripe fruit.

Figure 8:
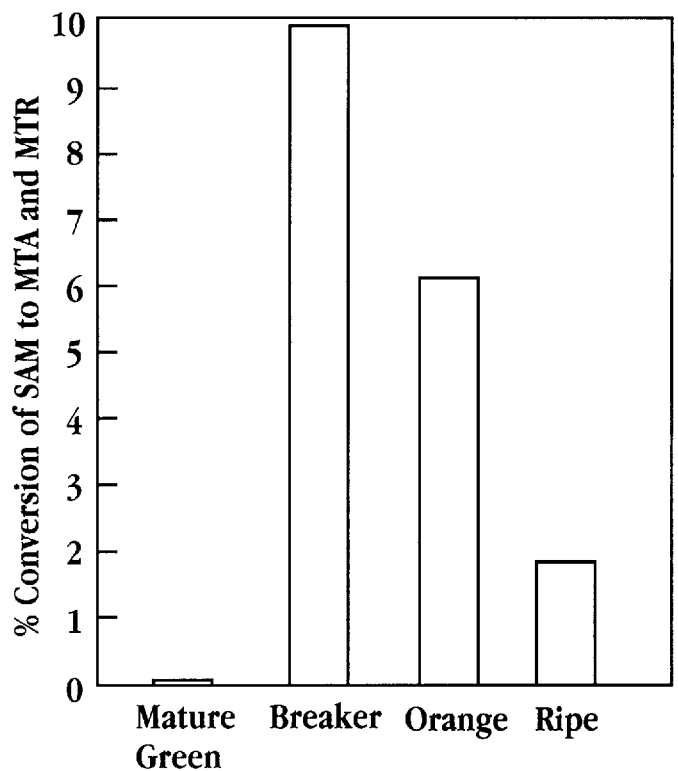
FIG. 8 is a graph representing the relative levels of AdoMetase activity in ripening tomatoes at different stages.

To determine whether the presence of AdoMetase enzyme activity correlated with the level of AdoMetase mRNA, an AdoMetase assay was performed using extracts from four fruit obtained at different stages from an ESKN transgenic plant (Example 5). FIG. 8 shows the level of AdoMetase activity in mature green, breaker, orange, and ripe fruit from a single pAG-5321 transgenic plant. These data demonstrate that AdoMetase activity follows roughly the same expression pattern in ripening fruit as the AdoMetase mRNA levels.

The data presented above suggest that inclusion of the upstream region of the native E8 promoter in a chimeric gene construct enhances long-lived expression of the chimeric gene in ripening transgenic tomatoes. FIG. 6 shows the RPA results from pGA-SESKN line 22A-1 and from pAG-5321 line 18. ESKN line 18 had one of the highest levels of AdoMetase expression of all the ESKN transgenic lines. Quantitative measurement of AdoMetase mRNA is shown in FIG. 7. The results show that the −2254 bp E8 promoter expression is maintained through the fully ripe stage of fruit development. This expression pattern is in sharp contrast to the −1124 bp E8 promoter (ESKN) mRNA levels also shown in FIG. 6.

Ethylene evolution measurements from fruit picked at breaker and analyzed daily are shown in FIG. 9. The rate at which fruit from SESKN lines 22A and 35-1 produced lycopene was reduced as evidenced by the time required for orange fruit development. Furthermore, the total amount of ethylene produced from these tomatoes was reduced by approximately 80%. The expression of AdoMetase and a reduction in ethylene biosynthesis was strictly correlated in the 25 SESKN transgenic plants analyzed.

Figure 10:
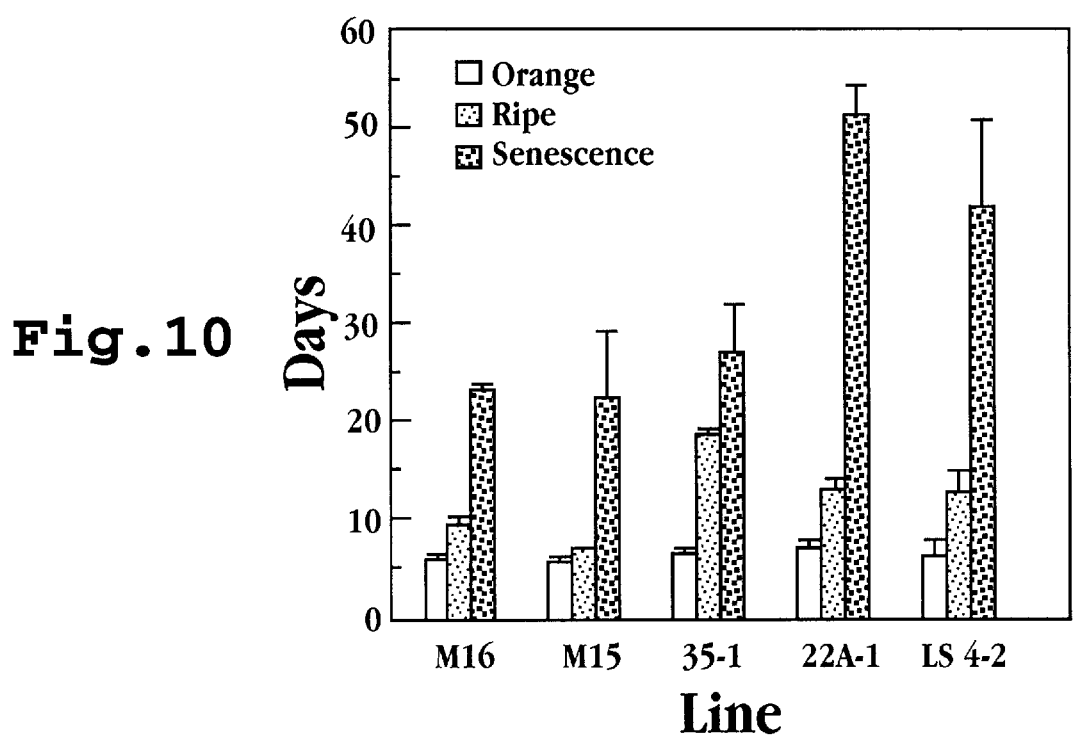
FIG. 10 illustrates the post-harvest shelf life of tomatoes obtained from SESKN transgenic plants.
Figure 9A:
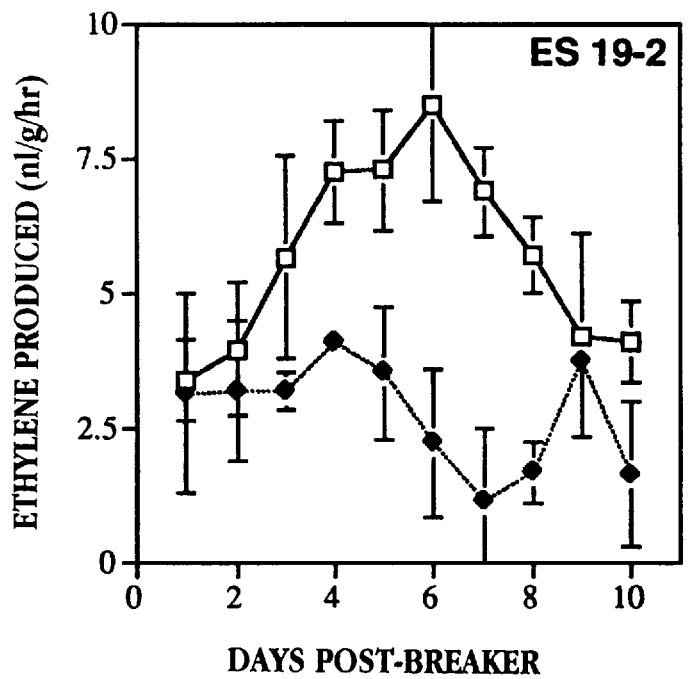
FIGS. 9A to 9D present the data for ethylene production in the fruit of 4 different transgenic plants (FIG. 9A, ES 19-2.
Figure 9B:
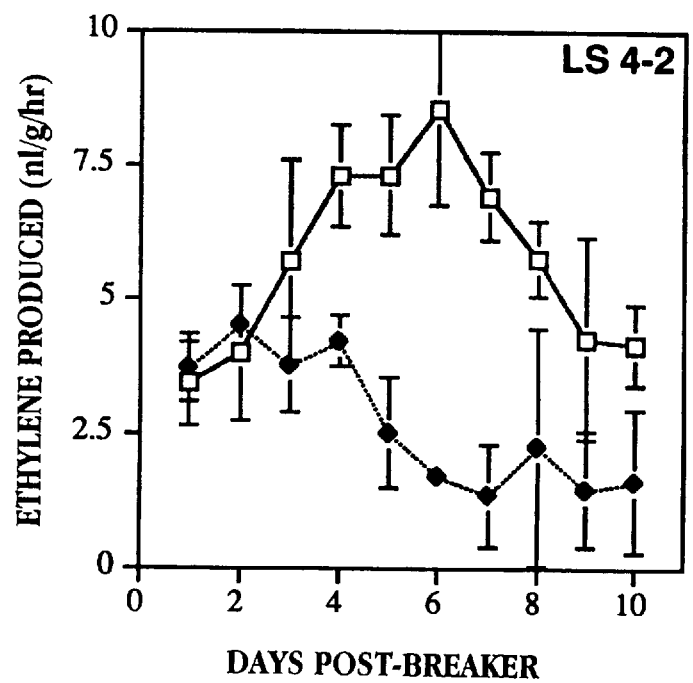
Figure 9C:
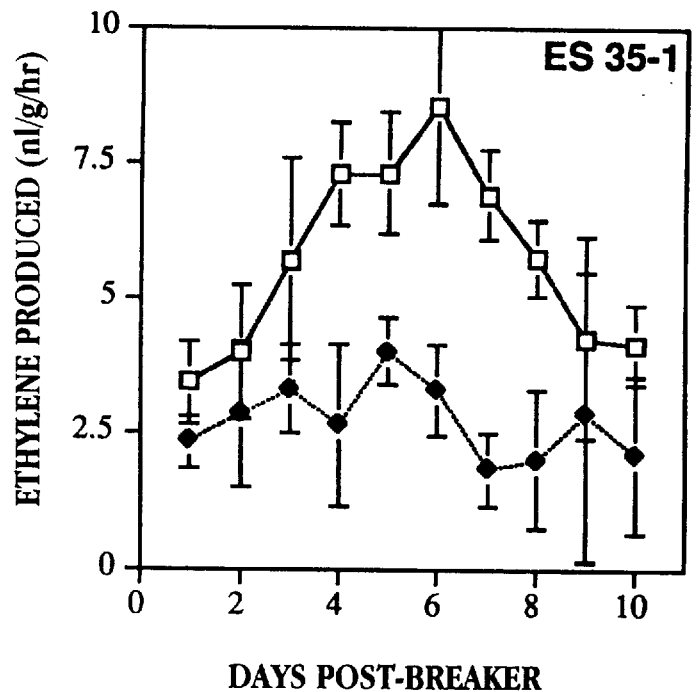
Figure 9D:
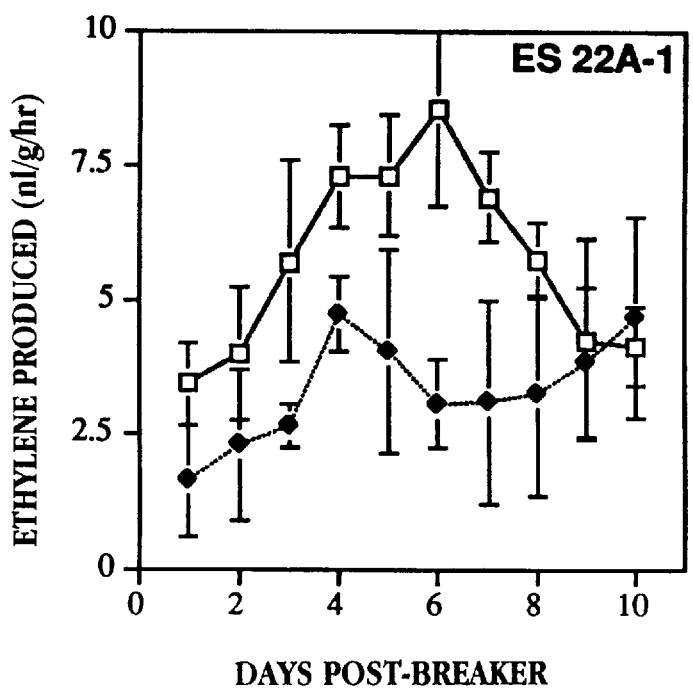

The SESKN tomatoes that synthesized less ethylene were assessed for their shelf life properties when stored at room temperature (22° C.) (Example 5). Three fruit each from SESKN lines 22A-1 and 35-1 were compared with untransformed normal tomatoes. Senescence was determined by visually observing contraction and wrinkles on the tomato skin. Firmness was not measured but was noted to be much greater in the transgenic lines. The results of these senescence assessments are shown in FIG. 10. Even at 55 days post-breaker, the 22A-1 tomatoes remained firm and appeared to be suffering more from dehydration than from the softening-induced senescence of the normal tomatoes.

These results demonstrate the ability to provide tissue specific regulation to DNA sequences encoding a gene product, e.g., AdoMetase enzyme, in transgenic plants. In addition, the results obtained with the two different E8 promoters (lower E8 and SE8) suggest the use of these promoters for similar tissue specific expression of any desired gene product. Further, the two regions of the E8 promoter (lower E8 and upper E8, FIG. 4) can be used as hybridization probes against libraries of DNA representative of the genomes of other plant species. Homologous sequences to the E8 promoter are then tested for tissue specific expression in the plant species from which they were isolated. Such promoters, as well as the E8 promoter itself, can be tested for regulatable expression in heterologous plant systems using the methods described herein. A reporter gene, such as GUS (β-glucuronidase), can be used to test tissue specific regulatable expression from these promoters. Expression of GUS protein can be easily measured by fluorometric, spectrophotometric or histochemical assays (Jefferson, 1987).

Variants of the E8 promoter may be isolated from different tomato cultivars or other plant species by standard recombinant manipulations such as primer specific amplification (Mullis; Mullis, et al.) or oligonucleotide hybridization (Ausubel, et al.; Sambrook, et al.).

VII. Advantages of the Invention

These results demonstrate the ability to provide tissue and stage specific regulation of gene expression in transgenic plants. A tissue or stage specific promoter is a region of DNA that regulates transcription of the immediately adjacent (downstream) gene to a specific plant tissue or developmental stage of the plant or plant tissue. Other gene products which may be useful to express using these promoters include genes encoding (i) flavor (e.g., thaumatin) or color modification (e.g., products that modify lycopene synthesis), (ii) enzymes or other catalytic products (such as, ribozymes or catalytic antibodies) that modify plant cell processes, and (iii) gene products that affect ethylene production, such as antisense molecules, enzymes that degrade precursors of ethylene biosynthesis, catalytic products or cosuppression molecules. Further, it is useful to restrict expression of some genes to specific tissues, such as the fruit—for example, any gene that would be deleterious to the plant if it were expressed constitutively. Such genes would include genes which encoded degradative enzymes that deplete necessary metabolites.

As can be seen from the results described above, derivatives of the E8 and E4 promoter regions can be used as on/off switches for the tissue and stage specific expression of genes whose expression is under their control.

The constructs and methods of the present invention are applicable to all higher plants including, but not limited to, the following:

Solanaceae. Lycopersicon (tomato) and Capsicum (peppers);

Cucurbitaceae. Cucurbita (squashes), Cucumis (melons, cantaloupe) or Citrullus (watermelon);

Rosaceae. Malus (apple), Prunus (peaches, plums, nectarines), Rubus (raspberry), Fragaria (strawberry), and Pyrus (pears);

Annonaceae. Annona (sweetsop, cherimoya);

Musaceae. Musa (banana);

Lauraceae. Persea (avocado);

Saxifragaceae. Ribes (currents);

Ebenaceae. Diospyros (persimmon);

Caricaceae. Carica (papaya);

Anacardiaceae. Mangifera (mango);

Myrtaceae. Psidium (guava);

Actinidiaceae. Actinidia (kiwifruit).

Variants of the E8 and E4 promoter may be isolated from different tomato cultivars and from other plants by the methods described above. A reporter gene, such as GUS (β-glucuronidase), can be used to test tissue specific regulatable expression from such promoters. Expression of GUS protein can be easily measured by fluorometric, spectrophotometric or histochemical assays (Jefferson, 1987).

A further advantage of the present invention is the ability to produce fruit that initiate ripening, but the subsequent down regulation of ethylene production delays the overall time course of fruit ripening, i.e., the fruit are suspended or delayed in their ability to complete the ripening process.

VIII. Utility

A. The Vectors of the Present Invention.

The present invention provides vectors suitable for the transformation of plants. The vectors, chimeric genes and DNA constructs of the present invention are also useful for the expression of heterologous genes. Transgenic plants, and their fruit products, carrying the chimeric genes of the present invention, may be a useful source of recombinantly-expressed material.

In one embodiment, the chimeric genes of the present invention have two components: (i) a DNA sequence encoding a product that is effective to reduce ethylene biosynthesis in fruit from the plant, and (ii) a promoter whose expression is induced during fruit ripening or in response to ethylene.

The vectors of the present invention may be constructed to carry an expression cassette containing and insertion site for DNA coding sequences of interest. The transcription of such inserted DNA is then under the control of a suitable promoter (i.e., a promoter whose expression is induced during fruit ripening, in response to ethylene, or in response to a plant cytokine). Exemplary of such promoters are promoters obtained from tomato E4 or E8 genes, or homologs thereof (e.g., raspberry E4), and avocado cellulase gene or tomato polygalacturonase gene.

Such expression cassettes may have single or multiple transcription termination signals at the coding-3'-end of the DNA sequence being expressed. The expression cassette may also include, for example, DNA sequences encoding (i) a leader sequence (e.g., to allow secretion or vacuolar targeting), and (ii) translation termination signals.

Further, the vectors of the present invention may include selectable markers for use in plant cells (such as, the nptII kanamycin resistance gene). The vectors may also include sequences that allow their selection and propagation in a secondary host, such as, sequences containing an origin of replication and a selectable marker. Typical secondary hosts include bacteria and yeast. In one embodiment, the secondary host is *Escherichia coli,* the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens,* and chimeric genes or expression cassettes (described above). Further, the vectors of the invention may comprise a disarmed plant tumor inducing plasmid of *Agrobacterium tumefaciens*.

The vectors of the present invention are useful for stage and/or tissue specific expression of nucleic acid coding sequences in plant cells. For example, a selected peptide or polypeptide coding sequence can be inserted in an expression cassette of a vector of the present invention. The vector transformed into host cells, the host cells cultured under conditions to allow the expression of the protein coding sequences, and the expressed peptide or polypeptide isolated from the cells. Transformed progenitor cells can also be used to produce transgenic plants bearing fruit.

In one aspect of the invention, fruit produced by such transgenic plants has an initial burst of ethylene production, followed by a reduction in the level of ethylene synthesis by the fruit. The fruit then demonstrates a modified ripening phenotype.

The vectors, chimeric genes and DNA constructs of the present invention can be sold individually or in kits for use in plant cell transformation and the subsequent generation of transgenic plants.

B. Transgenic Plants and Fruit.

Experiments performed in support of the present invention demonstrate that plants carrying chimeric genes of the present invention (comprising, a DNA sequence encoding a product that is effective to reduce ethylene biosynthesis in fruit from the plant and a promoter whose expression is induced during fruit ripening or in response to ethylene) exhibit significantly lower levels of ethylene production following harvest. Examples of this result have been described herein, for example, using expression of the AdoMetase gene under the control of a E4 and E8 promoters. Due to the deleterious effects of ethylene biosynthesis on the handling and storage of commercially-important plants and plant products (such as fruits, vegetables and flowers) plants in which ethylene synthesis is reduced are of substantial value.

Similarly, flowering plants containing heterologous genes effective to reduce ethylene biosynthesis will retain a fresh appearance longer than untransformed counterparts. Reduced ethylene biosynthesis in leafy vegetables, such as lettuce, would reduce leaf browning and lead to a longer shelf-life. The transgenic tomatoes described herein are illustrative of present invention. These transgenic tomatoes remain firm much longer after harvest than normal tomatoes, such transgenic tomatoes may be harvested at a later, vine-ripened, stage and still retain the transportability previously associated with, for example, green tomatoes.

Further, the expression constructs of the present invention allows an initial burst of ethylene synthesis to begin the ripening process. The promoters of the present invention can be manipulated to suspend further ripening or to increase the time-course of the ripening process (relative to wild-type fruit). The constructs of the present invention demonstrate the first example of tissue-type or developmental stage-specific control over ethylene production.

C. Expression in Heterologous Plant Systems

Experiments performed in support of the present invention demonstrate the versatility of the chimeric gene constructs of the invention. The vector constructs of the present invention can be used for transformation and expression of heterologous sequences in transgenic plants independent of the original plant source for the promoter sequence. For example, the tomato E4-Adometase chimeric gene was introduced into raspberries. The transgenic raspberries were propagated under green house conditions. Proteins were prepared from the transgenic raspberry fruit, the proteins size-fractionated and transferred to nylon membranes. The bound proteins were then probed with a monoclonal antibody specifically immunoreactive with the Adometase protein. Results from these experiments demonstrate the expression of Adometase in the raspberry fruit.

These data suggest that the tomato E4 promoter is useful for the promotion of gene expression in tomato and heterologous systems, i.e., plant cells other than tomato. Further, the expression mediated by the promoter appears to be tissue/developmental-stage specific even in heterologous plants. These findings support the usefulness of the vectors, chimeric genes and DNA constructs of the present invention for transformation of species of fruit-bearing plants, where such plants are different species than the plant source of the promoter sequences.

The following examples illustrate, but in no way are intended to limit the present invention.

Materials and Methods

Tomato seed (*Lycopersicon esculentum* Mill. var. *cerasiforme* (Dunal) Alef. cv. Large Red Cherry) were obtained from Peto Seed, Inc. (Saticoy, Calif.) and were grown under standard greenhouse conditions. Harvested fruit were stored at room temperature (22° C.).

Standard recombinant DNA techniques were employed in all constructions (Adams, et al.; Ausubel, et al., Sambrook, et al.).

EXAMPLE 1

Cloning of the AdoMetase Gene

A. Isolation of the AdoMetase Gene.

The AdoMetase gene was identified on an AluI-HaeIII restriction fragment from purified T3 DNA (Hughes, et al., 1987a). Bacteriophage T3 is available under ATCC No. 11303-B3 (American Type Culture Collection, 12301 Parklawn Dr., Rockville Md. 20852). The DNA fragment was first cloned into the bacteriophage M13 MP8 vector (Pharmacia LKB Biotechnology, Inc., Pistcataway, N.J.). A MaeIII to BamHI fragment was subcloned into the pUC19 plasmid vector (Pharmacia) to produce pUC19-AdoMetase (pAG110 or pUC19-SAMase; FIG. 2). This vector was transformed into *E. coli* and used as a source of DNA for further construction experiments and for DNA sequence determination.

B. Modification of the Amino-Terminal Sequence of the Cloned AdoMetase Gene.

The cloned AdoMetase gene was further engineered to contain a consensus eukaryotic translation initiation site (Kozak; Lutcke, et al.) by altering the nucleotide sequence surrounding the SAMase ATG start-codon using a synthetic double-stranded oligonucleotide.

The plasmid pUC19-AdoMetase (pAG110) was digested with XmaI and BamHI and the 1.9 kb and 1.3 kb fragments were purified by electro-elution after agarose gel electrophoresis. A double stranded synthetic oligonucleotide linker having the sequence indicated in FIG. 3 was ligated to the 1.9 kb fragment and this ligated DNA subjected to XmaI digestion to remove excess linkers.

The linkered 1.9 kg fragment was then re-purified by electrophoresis on low melting temperature agarose and ligated to the 1.3 kb fragment to form the plasmid pUC19-SAM-K (pAG-111). The altered gene region was subjected to DNA sequence analysis. The gene sequence is given in FIGS. 11A to 11D. This gene was designated SAM-K and used to construct the following plant expression vectors. This plasmid DNA can also be used to directly transform the plant host via electroporation, microinjection, or microprojectile bombardment.

C. Vector Constructions using the Tomato E8 Promoter.

Two different forms of the E8 promoter were used to construct SAM-K-containing vectors. The first (−1124 bp) was isolated from tomato (*Lycopersicon esculentum* var. *cerasiform*) DNA using polymerase chain reaction (PCR) (Mullis; Mullis, et al.; Perkin-Elmer Cetus, Norwalk, Conn.). The primers used in the PCR reaction were based on the sequence described by Deikman, et al. (1988). The sequences of the oligonucleotide primers are given in FIG. 3. The oligonucleotides were designed to incorporate restriction endonuclease sites (XbaI and NcoI) at the 5' and 3' ends, respectively, of the amplified E8-promoter fragment. These restriction endonuclease cleavage sites facilitated subcloning into the pUC19-SAM-K vector (see FIG. 2): an NcoI site is present near the ATG start codon region in the synthetic oligonucleotide.

Figure 12A:
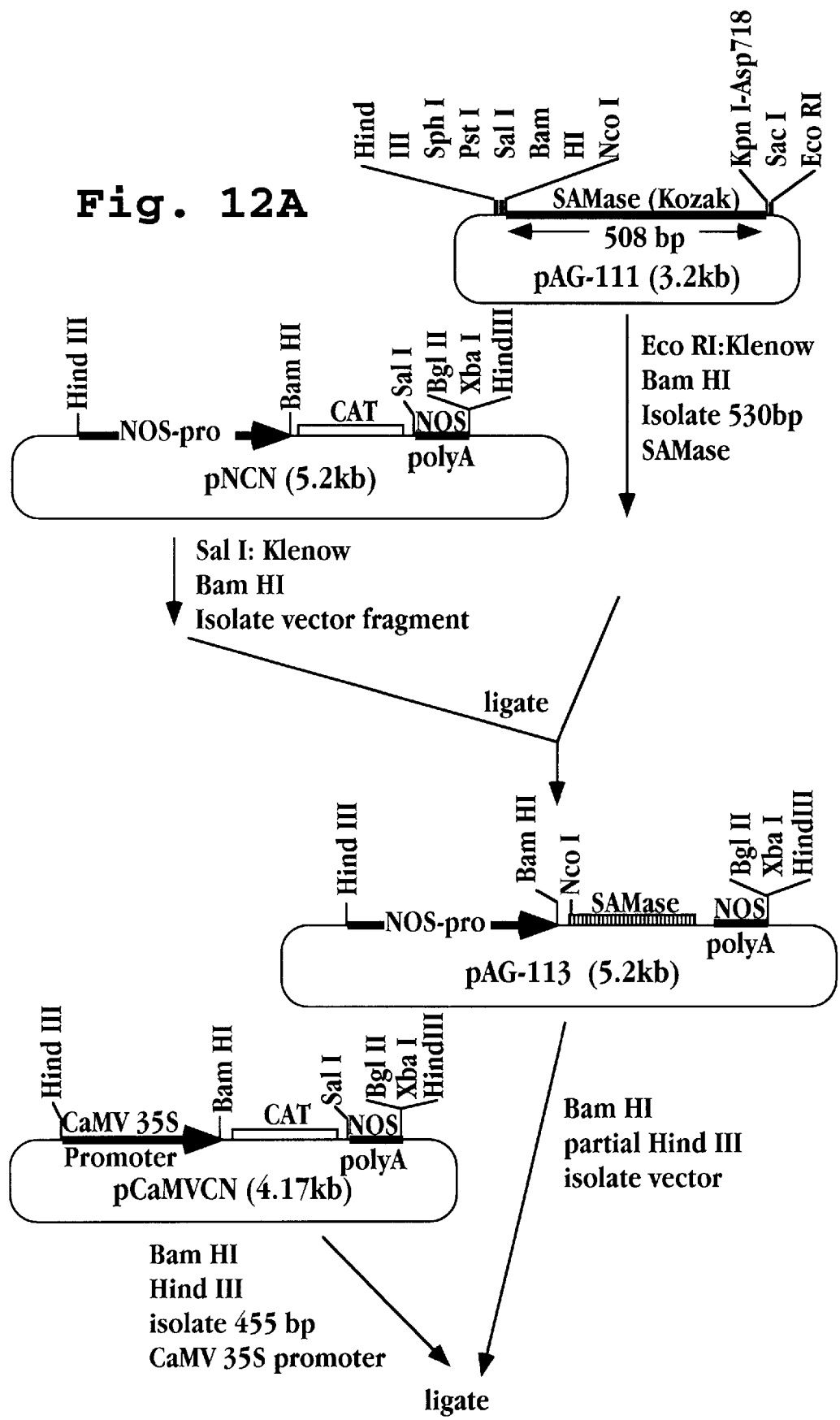
FIGS. 12A and 12B diagram the steps followed in constructing vector pAG-114 (pESKN).

FIG. 12A outlines the generation of the vector pAG-5321 (pGA-ESKN) starting from vector pNCN (Pharmacia, Inc., Piscataway, N.J.) and pUC-SAM-K (described above). The sequence of the E8 promoter (the lower E8 promoter) is similar to the sequence presented as bases 1189 to 2214 in FIGS. 13A and 13B.

Figure 12B:
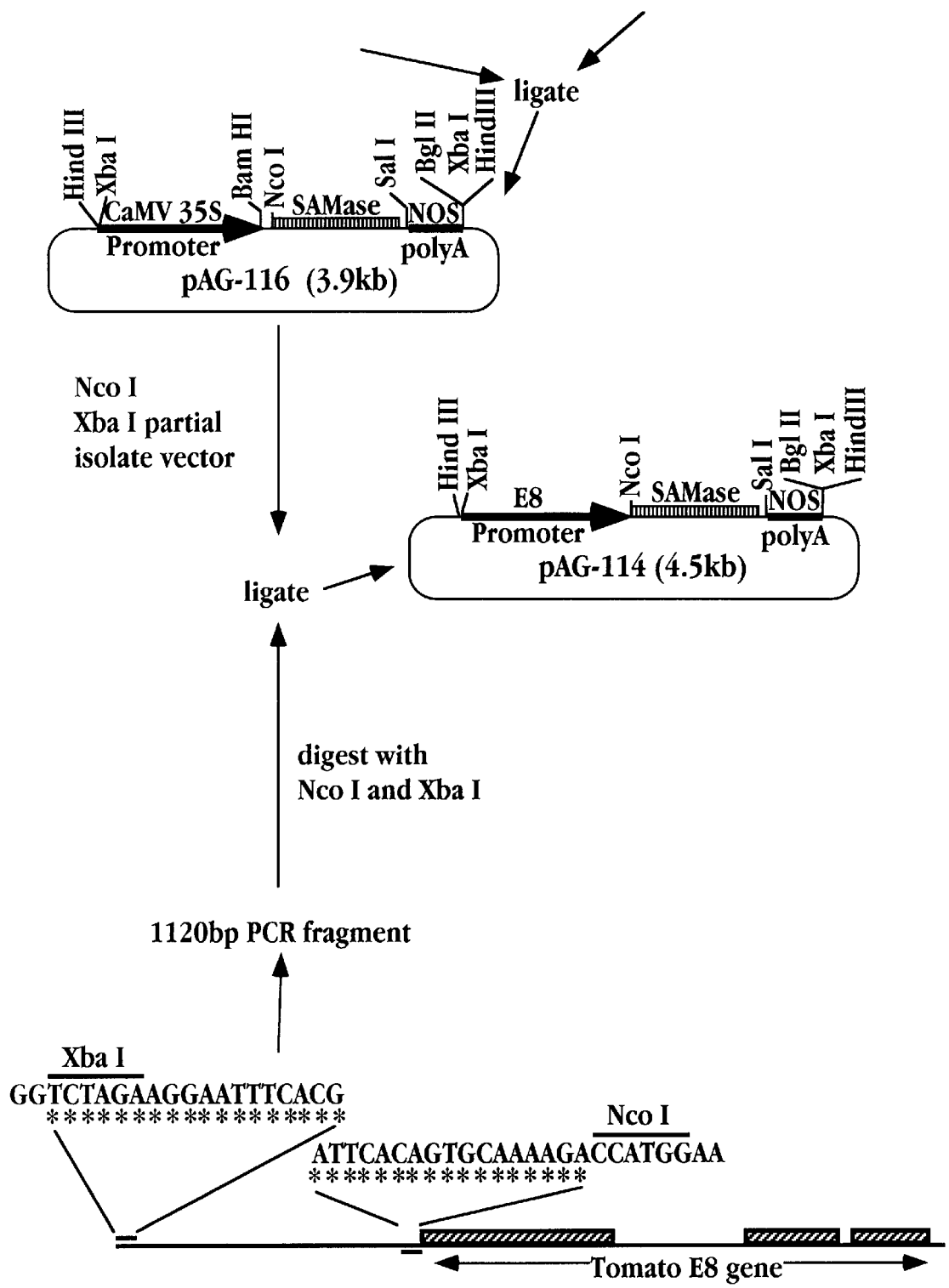
Figure 12C:
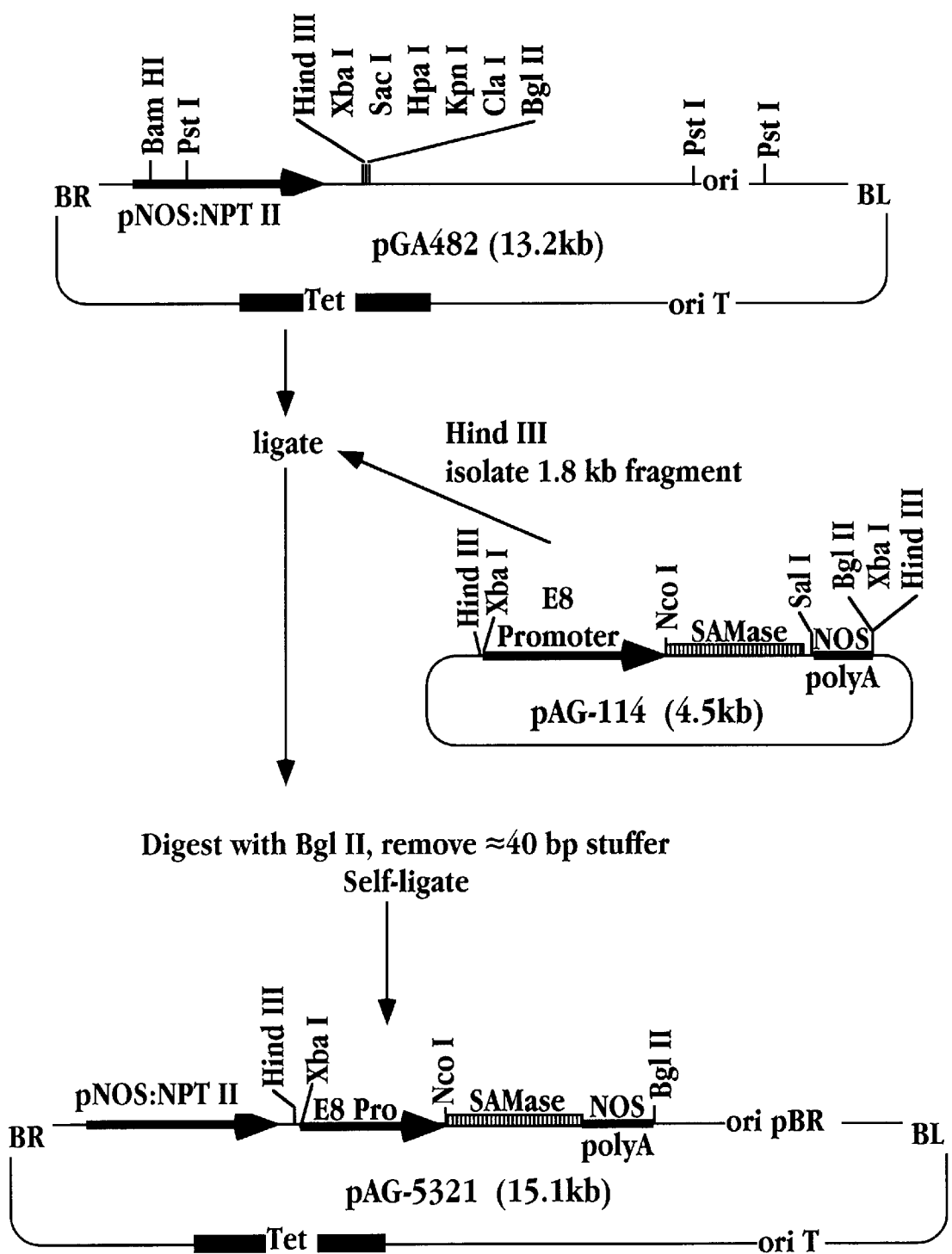
FIG. 12C shows a diagram of the steps followed in constructing vector pAG-5321 (pGA-ESKN).

FIG. 12C outlines one approach to the generation of Agrobacterium vectors for use in the present invention. However, the E8/AdoMetase cassette, present in, for example, pAG-5321, can be incorporated in a number of vectors useful for plant transformation.

Agrobacterium binary vectors were developed from pGA482 (An, et al., 1985), a pBIN19 derivative (Clontech Laboratories) containing the neomycin phosphotransferase II gene fused to the nopaline synthesis gene promoter (An, et al., 1988). The resulting vector, designated pAG-5321 is shown in FIG. 5A.

The second E8 promoter (−2254 bp) was isolated from a lambda EMBL-3 clone that contained the entire E8 gene. The E8 gene clone was selected from a tomato (*Lycopersicon esculentum* var. VFN8) genomic library obtained from Clontech Laboratories (Palo Alto, Calif.) using the PCR-derived E8 promoter fragment (described above) as a hybridization probe in plaque-lift filter hybridizations. The lambda clone carrying the E8 gene was identified by a positive hybridization signal. The E8-bearing phage was plaque purified and the lambda phage DNA isolated.

The lambda E8 genomic clone was used as a source of the HindIII to XbaI fragment that is the approximately −2254 to −1124 bp upstream region of the E8 promoter. This fragment was inserted 5' of the approximately −1124 bp E8 promoter in pAG-5321 at the HindIII and XbaI sites (FIG. 4). The resulting plasmid was named pGA-SESKN. FIGS. 13A and 13B show the nucleotide sequence of the −2216 bp region from one cultivar (Deikman, et al., 1988, 1992). The HindIII to XbaI fragment (used for construction of the approximately −2254 promoter) contains additional sequences 5' to the end of this −2216 bp sequence.

FIG. 4 shows the relationship of the two portions of the E8 promoter that are present in pGA-SESKN.

Standard recombinant DNA techniques were employed in all constructions (Adams, et al.; Ausubel, et al.). Another lambda vector, pGEM7Zf(+)SAM-K, was constructed by cloning the BamHI to KpnI AdoMetase fragment from pUC19-SAM-K into the same sites of pGEM7Xf(+) (Promega, Inc., Madison, Wis.).

Other plant cloning vectors, such as pBI121 (Clontech Laboratories, Inc., Palo Alto, Calif.), can also be used to practice the present invention. The plant promoter upstream of the AdoMetase gene sequence can be varied to obtain tissue specific expression, temperature dependent expression, or light dependent expression in the transgenic plants. Another useful plant promoter, in addition to the E8 promoter described above, is the constitutive Cauliflower Mosaic Virus (CaMV) promoter (Pharmacia).

EXAMPLE 2

Plant Transformation

The pAG-5321 and pGA-SESKN AdoMetase plasmids were separately introduced into Agrobacterium using a direct transformation method.

*Agrobacterium tumefaciens* strain EHA101 (Hood, et al.), a disarmed derivative of *Agrobacterium tumefaciens* strain C58, was used to introduce coding sequences into plants. This strain contains a T-DNA-less Ti plasmid. The pAG-5321 and pGA-SESKN AdoMetase plasmids were transferred into EHA101 using electroporation essentially as described by Nagel, et al. Briefly, an *Agrobacterium tumefaciens* culture was grown to mid-log phase (OD 600 0.5 to 1.0) in YEP media (10 g yeast extract, 10 g peptone, and 5 g NaCl per liter). After chilling on ice, 50 mls of these cells were pelleted, resuspended in 1 ml of ice cold 20 mM $CaCl_2$ and split into 1 ml aliquots.

Typically, one µg of plasmid DNA was added to an aliquots and incubated on ice for 30 minutes. The aliquot was then frozen in liquid nitrogen and thawed at 37° C. for 5 minutes. One ml of YEP media was added and incubated at 28° C. for 2 hours. The cells were pelleted, resuspended in 50 µl of YEP, and plated on YEP agar plates containing 20 µg/ml kanamycin. Kanamycin-resistant transformed colonies appear within 2 days.

Tomato cotyledon tissue explants were excised from both the tip and base of the cotyledon. Cotyledon explants were pre-conditioned for 2 days on tobacco feeder plates (Fillatti, et al.). The pre-conditioned explants were inoculated with EHA101 containing the pAG-5321 or pGA-SESKN AdoMetase plasmid of interest and finally placed in a 10 ml overnight culture of EHA101/[pAG-5321 or pGA-SESKN] for 5 minutes. The explants were then co-cultivated with the EHA101 strains for 2 days on tobacco feeder plates as described by Fillatti, et al.

The explants were grown in tissue culture media (Fillatti, et al.) containing 2 Z media, MS salts, Nitsch and Nitsch vitamins, 3% sucrose, 2 mg/l seatin, 500 mg/l carbenicillin, 100 mg/l kanamycin and 0.7% agar. The explants were grown in tissue culture for 8 to 10 weeks. The carbenicillin treatments were kept in place for 2 to 3 months in all media. The explants and plants were kept on carbenicillin until they were potted in soil as a counter-selection to rid the plants of viable *Agrobacterium tumefaciens* cells.

EXAMPLE 3

RNAase Protection Assays for the Detection of SAMase mRNA

Tomato fruits at various stages of development from transgenic plants and wild-type plants were used as mRNA sources. mRNA was extracted from tomato cells and purified using the "QUICK PREP RNA" kit from Pharmacia, Inc. RNAse Protection Assays (RPA) were performed following the manufacturer's instructions using an "RPAII" kit from Ambion, Inc. (Hialeah, Fla.). This method has been previously described by Lee, et al.

pGEM7Zf(+)SAM-K was used to generate $^{32}$P-UTP-labeled RNA probe using bacteriophage T7 RNA polymerase as contained in the "RIBOPROBE IT T7 RNA POLYMERASE SYSTEM" from Promega, Inc. The radiolabeled probe was purified on a preparative polyacrylamide gel and used for up to one week.

One microgram of isolated mRNA was hybridized to approximately 10,000 CPM of the RNA probe and further processed as per the instructions in the "RPA II" kit. Briefly, one microgram of the purified mRNA was mixed with 10,000 CPM of the RNA probe in a total volume of 15 μl. 20 μl of a hybridization buffer that allows hybridization of complementary sequences (Ausubel, et al.; Maniatis, et al.; Sambrook, et al.) is then added. The hybridization solution is provided in the "RPAII" kit from Ambion. The solution was heated to 90° C. for 3–4 minutes to denature all the RNA and incubated at 45° C. overnight to allow hybridization of complementary sequences. The solution was cooled to 37° C. and RNase (provided in the Ambion kit) was added which degrades all un-hybridized probe.

Protected probe was resolved on a denaturing polyacrylamide gel, dried, and exposed to film for up to 16 hours. Quantitative analysis of the RPA signals was accomplished by excising each band from the gel, dissolving the band in a liquid fluor, and determining the radioactivity present in the sample using liquid scintillation counting. A standard curve was generated using various amounts of unlabeled RNA synthesized from a AdoMetase fragment cloned into pGEM5Z(+) in the sense orientation. The linear range of the assay was dependent on the amount of input $^{32}$P-labeled RNA probe in the RNAase protection assay but typically ranged from 10 pg to 1 ng of mRNA.

EXAMPLE 4

Ethylene Measurements

The assay for tomato ethylene evolution is performed over a 0.5 to 1.0 hour period by sealing glass jars containing individual fruit and sampling 2 ml aliquots for gas chromatographic analysis. A Hewlett Packard 5890 (Palo Alto, Calif.) gas chromatograph with a flame ionization detector and a 6 ft Porapak N column was used for ethylene measurements (Adams, et al.). This system combined with an HP Vectra computer and the current version of "CHEMSTATION" (Hewlett Packard) allows measurement of ethylene concentrations as low as 0.2 nl of ethylene in a 2 ml sample (0.1 ppm). After measurement of the ethylene in the headspace, the values are converted to nl of ethylene per gram of tissue per hour.

EXAMPLE 5

Characterization of Transgenic Tomatoes

A. Promoter Effect on SAMase mRNA Levels in Ripening Transgenic Fruit.

Transgenic fruit were selected from two transgenic plants, ESKN #18 and SESKN #22A, at three stages of ripening, breaker (Br), Orange (Or) and Ripe (Ri). Transgenic plant ESKN #18 contained the lower E8 promoter (FIG. 4) adjacent the Sam-K AdoMetase gene. Transgenic plant SESKN #22A contained the entire SE8 promoter (FIG. 4) adjacent the Sam-K AdoMetase gene. The AdoMetase mRNA level in ripening transgenic fruit was determined as described in Example 3.

The products of the RNA protection assay were resolved on polyacrylamide gels and exposed to X-ray film. A representative autoradiogram of the RNA protection assay is presented in FIG. 6. As can be seen in the figure, AdoMetase mRNA was present in both transgenic plants at the breaker stage of fruit ripening. However, the levels of AdoMetase mRNA drop in the ESKN transgenic plant, relative to the SESKN transgenic plant, at the orange and ripe stages of fruit ripening.

The level of AdoMetase mRNA was quantitated as described in Example 3 by liquid scintillation counting and determination of mRNA concentrations relative to a standard curve. FIG. 7 presents the results of this analysis. The results are consistent with those shown in FIG. 6. AdoMetase mRNA was present in both transgenic plants at the breaker stage of fruit ripening with the concentrations lower in ESKN #18. At the orange and ripe stages of fruit ripening the levels of AdoMetase mRNA drop in the ESKN transgenic plant, relative to the level at breaker stage and the levels in the fruit from the SESKN transgenic plant. The AdoMetase mRNA levels stay relatively constant in the SESKN transgenic plant.

B. Relative Levels of SAMase Activity in Ripening Transgenic Tomatoes.

To determine whether the presence of AdoMetase enzyme activity correlated with the level of AdoMetase mRNA, a 14C-SAM-based AdoMetase assay was performed using extracts from four different fruit stages from a single pAG-5321 transgenic plant (ESKN).

Plant tissues to be assayed for AdoMetase enzyme activity were frozen and ground to a powder in liquid nitrogen. The ground tissue was then suspended in 1.5 volumes of 200 mM Tris-HCl (pH 7.5), 10 mM DTT, and 10 mM EDTA. The suspension was vortexed vigorously then subjected to centrifugation at 40,000×g at 4° C. for 20 minutes. The following was added to 50 μl of extract: 5 μl of $^{14}$C-SAM (DuPont-New England Nuclear, NEC-363) at 20 μCi/ml and a specific activity of 58.0 mCi/mmol. The reaction was incubated at 37° C. for 1 hour then 40 μl of the reaction was spotted on a cellulose think layer chromatography (TLC) plate (J. T. Baker, Inc., Phillipsburg, N.J., Baker-Flex Cellulose F) and resolved for 3 hours in 70:70:20:40, butanol:acetone:acetic acid:water. The MTA and MTR spots were identified using autoradiography, excised, and counted using liquid scintillation.

FIG. 8 shows the level of AdoMetase activity in mature green, breaker, orange, and ripe fruit. The level of AdoMetase activity is defined as the percent conversion of SAM (S-adenosylmethionine) to MTA (5'-Methylthioadenosine) and MTR (5'-Methylthioribose). The decreasing level of AdoMetase activity from breaker to ripe fruit in the ESKN transgenic plant is consistent with the AdoMetase mRNA levels shown in FIG. 7.

Untransformed tomato fruit extracts do not degrade SAM to MTA or MTR at any stage of ripening when used in this assay.

C. Ethylene Production in Ripening Transgenic Fruit.

Ethylene produced from transgenic tomatoes carrying the AdoMetase gene under the regulation of the SE8 promoter (FIG. 4) was determined as described in Example 4. Greenhouse grown tomatoes from 4 transgenic lines were tested. The results of the analysis are presented in FIGS. 9A to 9D. Each of the four graphs shown in FIG. 9 represent the comparison of fruit from one pGA-SESKN transgenic line (Es 19-2, LS 4-2, ES 35-1 and ES 22A-1) with the fruit from untransformed controls. The control values (open squares) are the same in each of the four graphs and represent the average of six fruit from two different plants. The values from each transgenic line (closed symbols) are the average of ethylene determinations for three fruit. Error bars represent one standard deviation of the data.

The data represent a time period of ten days after the breaker stage of fruit ripening (post-breaker). These data demonstrate a reduction in the amount of ethylene production in transgenic tomatoes versus normal fruit over the ten day period.

D. Post-Harvest Shelf-life of SESKN Tomatoes.

Tomatoes from the SESKN transgenic plants that synthesized less ethylene were assessed for their shelf life properties when stored at 22° C. Three fruit from each from SESKN lines 35-1, 22A-1 and LS4-2 were compared with tomatoes from two untransformed, normal plants (M16 and M15). Senescence was determined each day by visual examination of the fruit for the occurrence of contraction and wrinkles on the tomato skin. The results of these senescence assessments are shown in FIG. 10.

As can be seen from the results in the figure, the bar graph shows the time for the fruit to achieve each stage: all fruit were picked at the breaker stage. For instance, line 35-1 took 18 days to ripen (Ripe stage) but then senescence developed at day 27. Line 22A-1 took 7 days to turn orange, 13 days to turn red, then 52 days to senescence. Even at 55 days post-breaker, the 22A-1 tomatoes remained firm and appeared to be suffering more from dehydration than from the softening-induced senescence of the normal tomatoes.

Firmness was not measured for the tomatoes from the five plants described above, however, the firmness was noted to be much greater in the fruit from the transgenic lines.

EXAMPLE 6

Southern Blot Analysis of E4 Homologues in Several Species of Plants

A Southern blot analysis was conducted to determine if sequences homologous to the tomato E4 gene were present in other plant species. The blot consisted of HindIII digests of six genomic plant DNAs: tomato, raspberry, strawberry, melon, carnation and cauliflower, along with size standards. This blot was hybridized with a probe following standard methods (Maniatis, et al.). The probe was a ~740 bp polymerase chain reaction (PCR; Mullis, Mullis, et al.) product amplified from genomic tomato DNA using PCR primers flanking the coding sequence of the E4 gene. The probe was labeled by incorporating $^{32}$P-labeled nucleotides into the PCR reaction.

The primers were designed according to Cordes, et al. (1989). The 5' primer sequence, corresponding to the region between nucleotides 1439 and 1452 of the E4 gene (SEQ ID NO: 8), is represented as SEQ ID NO: 6 (ACG CAT GGA GGG TAA CAA). Positions 5–7 of this primer correspond to the ATG start codon of the E4 gene. The 3' primer sequence, corresponding to the region between nucleotides 2160 and 2177 of the E4 gene (SEQ ID NO: 8), is represented as SEQ ID NO: 7 (GAA GCA AGA CAG CAA ATG).

Figure 14:
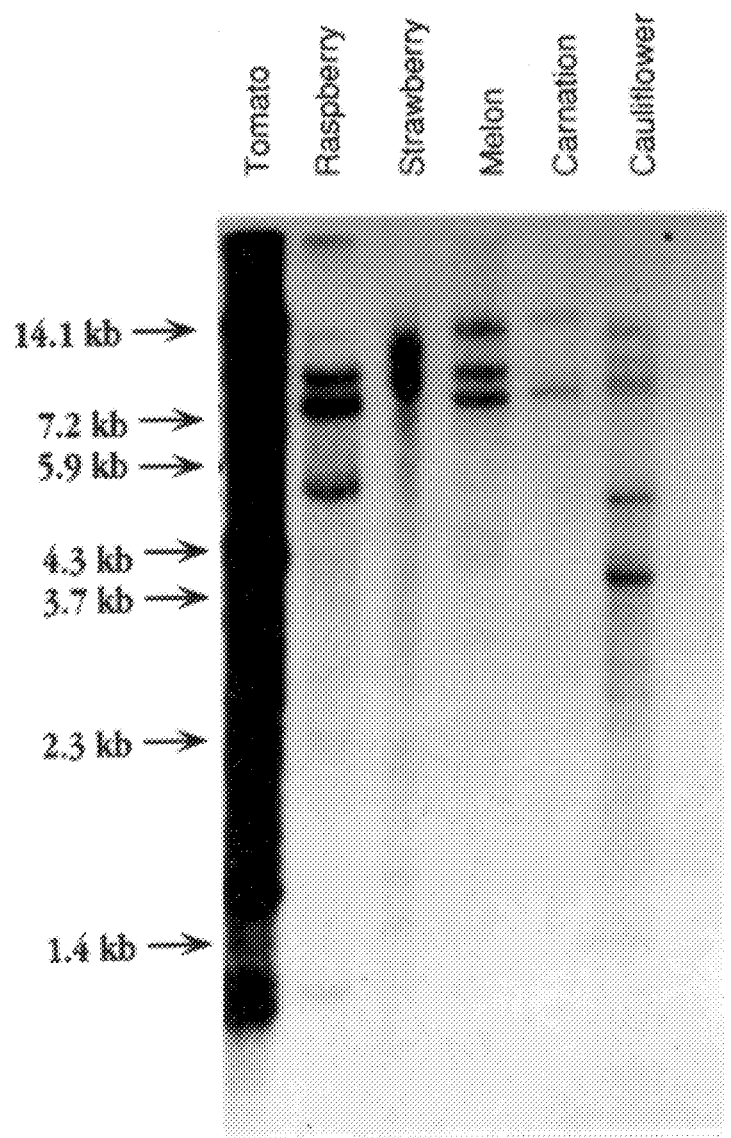
FIG. 14 is a photograph of an autoradiogram of a Southern blot of tomato, raspberry, strawberry, melon, carnation and cauliflower DNA probed with a fragment containing the coding sequence from the tomato E4 gene.

An autoradiograph of the blot is shown in FIG. 14. Several bands are apparent in each lane, with the lane corresponding to tomato DNA showing the strongest signal.

EXAMPLE 7

Isolation of DNA Fragments Homologous to Tomato E4 from a Raspberry Genomic Library A. Screening of the Library.

A raspberry genomic library in lambda GEM-11 was obtained from Novagen (Madison, Wis.) and screened by standard methods with the tomato E4 gene probe described above. Three lambda clones which hybridized to the probe were identified. The clones were purified by 3 rounds of plaque purification. One of the clones was selected for further analysis.

B. Analysis of a Positive Clone.

The clone was digested with several enzymes (Apa I, Bam HI, Eco RI, Hind III, Nco I, Sac I, and Sal I), run on a gel, and transferred to a "SUREBLOT" nylon membrane (Oncor, Gaithersburg, Md.). The blot was hybridized overnight at 42° C. with the tomato E4 probe in "HYBRISOL I" hybridization cocktail (Oncor, Gaithersburg, Md.). The final (most stringent) wash was 0.1% SSC, 0.1% SDS for 30 minutes at room temperature (22° C.).

A 1.6kb Sac I fragment which hybridized to the probe was subcloned into pGEM5Zf(+) (Promega, Madison, Wis.) and further characterized. A 225 bp region in that fragment was found to be highly homologous to the tomato E4 gene at both the DNA level (74%) and the amino acid level (80%). The sequence of this region (SEQ ID NO: 12) was compared to the sequence of a portion of the tomato E4 gene (SEQ ID NO: 8).

Additional raspberry E4 gene sequences were obtained by further hybridization screening of raspberry genomic library clones. The sequence of a genomic copy of a raspberry E4 gene is presented in FIGS. 15A to 15E (nucleotide sequence: SEQ ID NO: 25; polypeptide sequence: SEQ ID NO: 26).

EXAMPLE 8

Cloning of the AdoMetase Gene

A. Isolation of the AdoMetase Gene.

The AdoMetase (SAMase) gene was identified on an AluI-HaeIII restriction fragment from purified T3 DNA (Hughes, et al., 1987a). Bacteriophage T3 is available under ATCC No. 11303-B3 (American Type Culture Collection, 12301 Parklawn Dr., Rockville Md. 20852). The DNA fragment was first cloned into the bacteriophage M13 MP8 vector (Pharmacia LKB Biotechnology, Inc., Pistcataway, N.J.). A MaeIII to BamHI fragment was subcloned into the pUC19 plasmid vector (Pharmacia) to produce pAG-110 (pUC19-SAMase, FIG. 2). This vector was transformed into E. coli and used as a source of DNA for further construction experiments, detailed below.

B. Modification of the Amino-Terminal Sequence of the Cloned AdoMetase Gene.

The cloned AdoMetase gene was further engineered to contain a consensus eukaryotic translation initiation site (Kozak; Lutcke, et al.) by altering the nucleotide sequence surrounding the AdoMetase ATG start-codon using a synthetic double-stranded oligonucleotide.

Plasmid pAG-110 was digested with XmnI and BamHI and the 1.9 kb and 1.3 kb fragments were purified by electro-elution after agarose gel electrophoresis. A double stranded synthetic oligonucleotide linker formed by annealing oligonucleotides represented by SEQ ID NO: 1 and SEQ ID NO: 3 (FIG. 2) was ligated to the 1.9 kb fragment. This ligated DNA was subjected to XmnI digestion to remove excess linkers.

The linkered 1.9 kb fragment was then re-purified by electrophoresis on low melting temperature agarose and ligated to the 1.3 kb fragment to form the plasmid pAG-111. The altered gene region was sequenced to confirm its identity. pAG-111 was used in subsequent recombinant DNA manipulations, including the construction of plant expression vectors, detailed below. This plasmid DNA can also be used to directly transform the plant host via electroporation, microinjection, or microprojectile bombardment.

C. Vector Constructions using the Tomato E4 Promoter.

1. pAG-110, pAG-111, pAG-117

Figure 16:
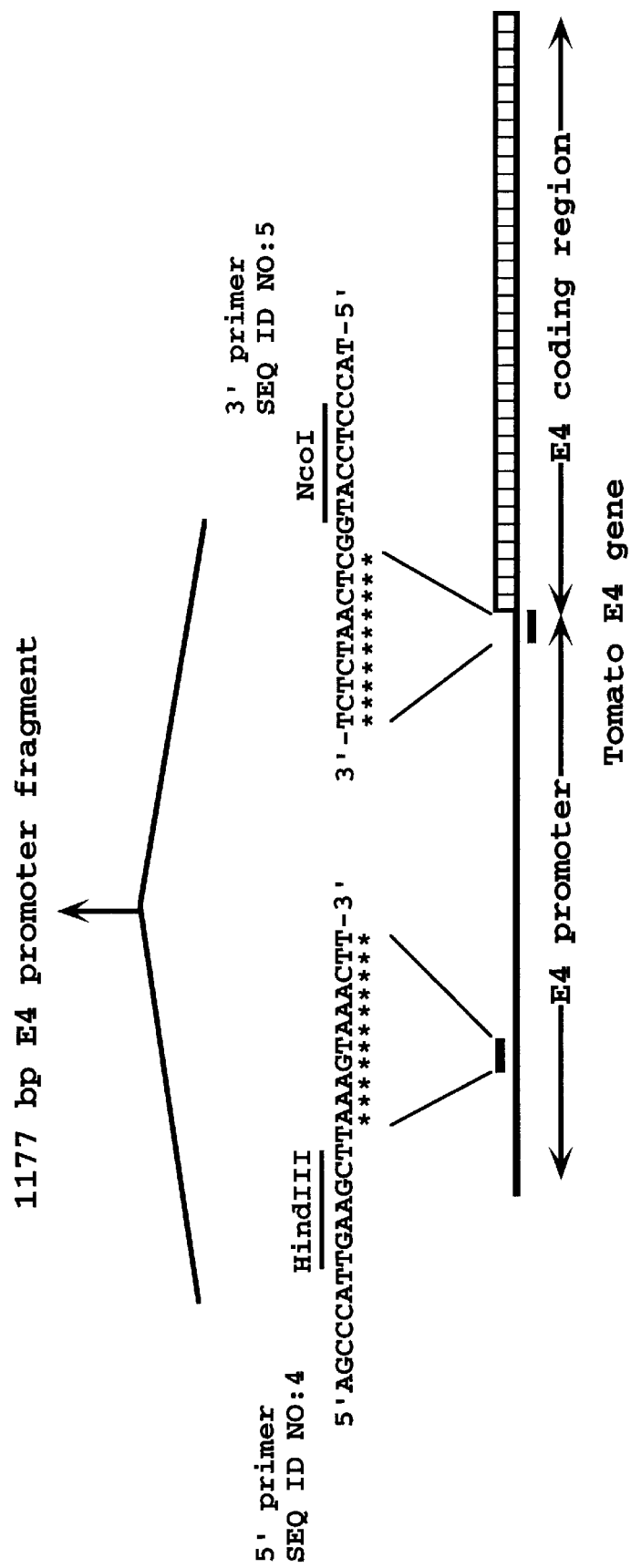
FIG. 16 shows a schematic of the tomato E4 gene, and the primers used to isolate a 1.18 kb tomato E4 promoter fragment.

A 1.18kb E4 promoter was isolated from tomato (*Lycopersicon esculentum* var. *cerasiform*) DNA using the polymerase chain reaction (PCR; Mullis; Mullis, et al.; Perkin-Elmer Cetus, Norwalk Conn.). The primers used in the PCR reaction were based on the sequence described by Cordes, et al. The sequences of the 5' and 3' oligonucleotide primers, shown in FIG. 16, are represented as SEQ ID NO: 4 and SEQ ID NO: 5, respectively. The oligonucleotides were designed to incorporate restriction endonuclease sites (HindIII and NcoI) at the 5' and 3' ends, respectively, of the amplified E4-promoter fragment. These restriction endonuclease cleavage sites were used to subclone the E4-promoter fragment (FIG. 17A) into the pAG-111 vector (FIG. 17B), which contains an NcoI site at the ATG start codon in the region modified by the synthetic oligonucleotide (see FIG. 2). The resulting vector, containing an E4:SAMase chimeric construct in the region between the HindIII/KpnI sites, was termed pAG-117.

2. pAG-5321

Agrobacterium binary vectors were developed from pGA482 (An, et al., 1985), a pBIN19 derivative (Clontech Laboratories) containing the neomycin phosphotransferase II gene (providing kanamycin resistance) fused to the nopaline synthesis (NOS) gene promoter (An, et al., 1988).

FIG. 12B outlines the generation of vector pAG-5321 starting from vectors pGA482 and pAG-114. FIG. 12A outlines the generation of the vector pAG-114 from vectors pAG-111 (described above) and pNCN (Pharmacia, Inc., Piscataway, N.J.).

3. pAG-5520

Figure 17D:
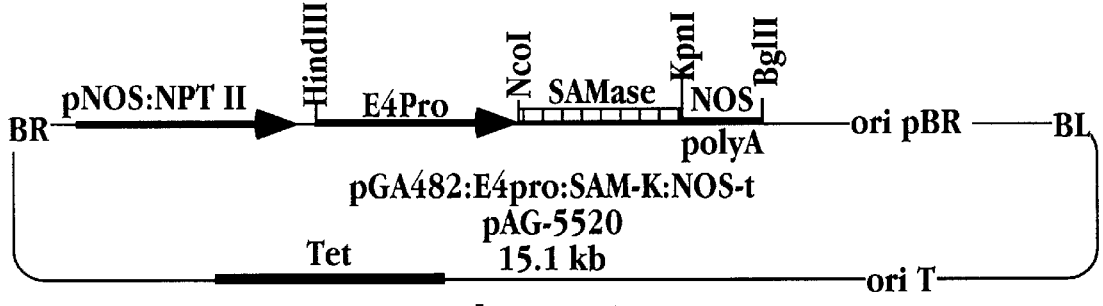

The E4:SAMase chimera was excised from pAG-117 with a HindIII/KpnI digest. The resulting 1.7 kb fragment was purified as above, and cloned upstream of the nopaline synthase polyA addition site in pAG-5321, resulting in pAG-5520 (FIG. 17D). The identity of the HindIII/KpnI insert was confirmed by DNA sequence analysis. This vector was used to generate the transgenic plants described herein.

FIGS. 17A–D and 12A to 12C outline one approach to the generation of Agrobacterium vectors for use in the present invention. However, the E4/SAMase cassette, present in, for example, pAG-117, can be incorporated in a number of vectors useful for plant transformation, such as pBI121 (Clontech Laboratories, Inc., Palo Alto, Calif.).

4. pAG-924

Vector pAG-924 was constructed by cloning the BamHI/KpnI SAMase fragment from pAG-111 into the same sites of pGEM7Zf(+) (Promega, Inc., Madison, Wis.). This plasmid was used to make the RNA probe for RNase protection assays, described in Example 8.

5. Other Constructs

DNA constructs may be made using genes other than the AdoMetase gene under the control of an E4 promoter, for example, other genes effective to reduce ethylene biosynthesis. Preferably, the E4 promoter is isolated from the same species of plant into which the construct is being introduced. For example, a tomato E4 promoter may be used to direct the expression of a heterologous gene, such as AdoMetase, in tomatoes, while a raspberry E4 promoter may be used to direct the expression of a heterologous gene in raspberries.

EXAMPLE 9

Plant Transformation

*Agrobacterium tumefaciens* strain EHA101 (Hood, et al.), a disarmed derivative of *Agrobacterium tumefaciens* strain C58, was used to introduce coding sequences into plants. This strain contains a T-DNA-less Ti plasmid. The pAG-5520 construct was transferred into EHA101 using electroporation essentially as described by Nagel, et al. Briefly, an *Agrobacterium tumefaciens* culture was grown to mid-log phase (OD 600 0.5 to 1.0) in MG/L media (5 gm tryptone, 2.5 g yeast extract, 5 gm NaCl, 5 gm mannitol, 1.17 gm sodium glutamate, 0.25 gm $K_2HPO_4$, 0.1 g $MgSO_4$, 2 µg biotin per liter, pH adjusted to 7.2 with NaOH). After chilling on ice 250 ml of the culture were pelleted, resuspended in sterile, chilled 1 mM Hepes/KOH pH 7.0, pelleted and resuspended as before, pelleted again, resuspended in sterile, chilled 10% glycerol, pelleted again, resuspended in 500 µl sterile, chilled 10% glycerol and split into 80 µl aliquots which were frozen on dry ice/ethanol and stored at –80° C.

Typically, 0.1–1 µg of plasmid DNA was added to a 40 µl aliquot of cells and incubated on ice 30–60 seconds. The mix was then transferred to a 0.1 cm gap electroporation cuvette (Invitrogen) and pulsed at 1.25 kV (BioRad Gene Pulser at 25 µF, BioRad Pulse controller at 200 Ω). One ml of MG/L media was added quickly after the pulse. The mixture was transferred to a microfuge tube and allowed to incubate at 28° C. for 1 hour. The cells were diluted 1:100, and 10 and 100 µl were plated on two MG/L plates containing 20 µg/ml kanamycin, respectively. Kanamycin-resistant transformed colonies appeared within 2 days.

Seven to eight day-old tomato cotyledon tissue explants were excised from both the tip and base of the cotyledon. Cotyledon explants were pre-conditioned for 2 days on tobacco feeder plates (Fillatti, et al.). The pre-conditioned explants were inoculated with EHA101 containing the pAG-5520 plasmid and placed in a 10 ml overnight culture of EHA101/pAG-5520 for 5 minutes. The explants were then co-cultivated with the EHA101 strain for 2 days on tobacco feeder plates as described by Fillatti, et al.

The explants were grown in tissue culture media (Fillatti, et al.) containing 2Z media, MS salts, Nitsch and Nitsch vitamins, 3% sucrose, 2 mg/l seatin, 500 mg/l carbenicillin, 100 mg/l kanamycin and 0.7% agar for 8 to 10 weeks. Carbenicillin was used for 2 to 3 months (until the plants were potted in soil) in all media as a counter-selection to rid the plants of viable *Agrobacterium tumefaciens* cells.

EXAMPLE 10

RNAase Protection Assays for the Detection of AdoMetase mRNA

Tomato fruits at various stages of development from transgenic plants and wild-type plants were used as mRNA sources. mRNA was extracted from tomato cells and purified using the "QUICK PREP RNA" kit from Pharmacia, Inc (Piscataway, N.J.). Alternatively, total RNA was isolated using a LiCl precipitation procedure. Tissues were frozen in liquid nitrogen and ground to a fine powder. 550 μl phenol/buffer (1:1, Tris-saturated phenol, pH 6.9 : Extraction buffer (100 mM LiCl, 100 mM Tris-HCl pH 8.0, 10 mM EDTA, 1% SDS)) at 80° C. was added for every 100 mg of the powder. The mixture was vortexed for 60 seconds, 250 μl chloroform was added, the mixture vortexed for another 30 seconds, and spun to separate the phases. The aqueous phase was removed to a new tube, an equal volume of 4M LiCl was added and mixed, and the sample was placed at −20° C. for 2 to 24 hours. The RNA was pelleted, washed and resuspended in water.

RNAse Protection Assays (RPA) were performed following the manufacturer's instructions using an "RPAII" kit from Ambion, Inc. (Hialeah, Fla.), as previously described by Lee, et al.

Plasmid pAG-924 was used to generate $^{32}$P-UTP-labeled RNA probe using bacteriophage T7 RNA polymerase as contained in the "RIBOPROBE II T7 RNA POLYMERASE SYSTEM" from Promega, Inc. The radiolabeled probe was purified on a preparative polyacrylamide gel and used for up to one week.

One microgram of isolated mRNA was hybridized to approximately 10,000 CPM of the RNA probe and further processed as per the instructions in the "RPA II" kit. Briefly, between 0.7 and 1.0 nanogram of the purified mRNA was mixed with 10,000 CPM of the $^{32}$P-RNA probe in a total volume of 15 μl. 20 μl of a hybridization buffer that allows hybridization of complementary sequences (Ausubel, et al.; Maniatis, et al.; Sambrook, et al.) is then added. The hybridization solution is provided in the "RPAII" kit from Ambion (Hialeah, Fla.). The solution was heated to 90° C. for 3–4 minutes to denature all the RNA and incubated at 45° C. overnight to allow hybridization of complementary sequences. The solution was cooled to 37° C. and RNase (provided in the Ambion kit), which degrades all un-hybridized probe, was added.

Protected probe was resolved on a denaturing polyacrylamide gel, dried, and exposed to film for up to 3 hours. Quantitative analysis of the RPA signals was accomplished by excising each band from the gel, dissolving the band in a liquid fluor, and determining the radioactivity present in the sample using liquid scintillation counting. A standard curve was generated using various amounts of unlabeled RNA synthesized from a AdoMetase fragment cloned into pGEM5Z(+) in the sense orientation. The linear range of the assay was dependent on the amount of input $^{32}$P-labeled RNA probe in the RNAase protection assay but typically ranged from 10 pg to 1 ng of mRNA.

EXAMPLE 11

Ethylene Measurements

A. Leaf disks

Measurement of ethylene from leaf discs was performed by excising five one-centimeter leaf discs from mature tomato leaves and placing them in a 25 ml Erlenmeyer flask on top of filter paper saturated with Murishige and Skoog (MS) medium or MS medium supplemented with 10 μM of the auxin naphthalene acetic acid (NAA).

B. Fruit

The assay for tomato ethylene evolution was performed by sealing glass jars containing individual fruit for a 0.5 to 1.0 hour period and sampling 2 ml aliquots for gas chromatographic analysis.

B. Ethylene measurements

Ethylene evolution was measured by gas chromatography/flame ionization after 20 hours and recorded as nanoliters of ethylene/gram fresh weight/hour. A Hewlett Packard 5890 (Palo Alto, Calif.) gas chromatograph with a flame ionization detector and a 6 ft Porapak N column was used for all ethylene measurements (Adams, et al., Ward, et al.). This system combined with an HP Vectra computer and the current version of "CHEMSTATION" (Hewlett Packard) allows measurement of ethylene concentrations as low as 0.2 nl of ethylene in a 2 ml sample (0.1 ppm).

Following measurement of the ethylene in the headspace, the values were converted to nanoliters of ethylene per gram of tissue per hour.

EXAMPLE 12

Western Blot Analysis

Frozen tomato tissues were ground in liquid nitrogen, extracted directly into Lammeli sample buffer (50 mM Tris,pH 6.8, 1% SDS, 5% betamecaptoethaon, 10% glycerol, and 0.005% bromophenol blue), heated to 95° C. for 5 minutes and centrifuged to remove debris. Total soluble protein in the supernatants was measured using the Coomassie Plus protein assay (Pierce, Rockford, Ill.). Eight micrograms of soluble protein from each sample, or known quantities of purified AdoMetase (positive control) were resolved on a polyacrylamide gel and electrophoretically transferred to Immobilon-P membrane using standard procedures. The blot was incubated with 2 μg/ml of the SAM10-9A3.1.3 monoclonal antibody to SAMase (Goding) in PBS-Tween (phosphate-buffered saline, 0.05% Tween 20), 1% bovine serum albumin (BSA) buffer for 60 minutes at 25° C. The blot was then washed 4 times in PBS-Tween buffer and incubated for 60 minutes with a goat antimouse HRP-conjugate suspended in PBS-Tween, 1% BSA buffer (Kirkegaard and Perry Laboratories, Inc., Gaithersburg, Md.). Bound antibody was detected using the Renaissance chemiluminescence reagent (DuPont NEN, Boston, Mass.) according to the manufacturer's instructions.

EXAMPLE 13

Characterization of Transgenic Tomato Plants

A. Promoter Effect on AdoMetase mRNA Levels in Wounded Leaves.

Fresh and wounded leaves from six independent transgenic plants, E4-1, E4-2, E4-3, E4-4, E4-5 and E4-6, were assayed for AdoMetase mRNA levels. All transgenic lines contained the E4 promoter adjacent the AdoMetase gene.

Single, freshly detached leaves were wounded by cutting 6–7 times with a dull knife. Two hours after wounding the total RNA was extracted, reacted and analyzed as described in Example 10. Fresh leaves were dropped directly into liquid nitrogen immediately after picking to halt RNAse activity, and processed as above.

The products of the RNA protection assay were resolved on polyacrylamide gels and exposed to X-ray film. A representative autoradiogram of the RNA protection assay is presented in FIG. 18A. As can be seen in the figure, expression of SAMase is silent in normal tomato plant leaves (fresh and wounded) and in fresh leaves isolated from transgenic plants. Expression of AdoMetase RNA is clearly evident, however, in wounded leaves from four of the six transgenic lines.

The level of AdoMetase mRNA was quantitated as described in Example 10 by liquid scintillation counting. FIG. 18B presents the results of this analysis, shown as a ratio of wound inducability, for four of the lines shown in FIG. 18A (E4-2, E4-4, E4-5 and E4-6), along with four other lines (E4-8, E4-10, E4-12 and E4-13). The results are consistent with those shown in FIG. 18A, and indicate that a transgene driven by an E4 promoter can be activated in plant tissues by the wounding of those tissues, in other words, that the E4 promoter is wound-inducible.

B. Promoter Effect on Ethylene Production in Wounded Leaves.

A leaf disc ethylene production assay was conducted, as detailed in Example 11, to measure the impact of wound-induced AdoMetase expression on wound-induced ethylene synthesis expected from these tissues. Leaves from a normal (M) and four transgenic (E4-2, E4-4, E4-5 and E4-12) tomato plants were cut with a cork bore into one cm discs that were measured for their ability to release ethylene.

Table 1 summarizes ethylene synthesis in leaves from control and four transgenic lines 4.5 and 19 hours after wounding. Leaves from two of the pAG-5520 transgenic lines were significantly reduced in their ability to produce ethylene. Lines E4-4 and E4-5 produced 69.6% and 84.8%, respectively, of the ethylene produced by the control plants during the first 4.5 hours. The ethylene reduction in those two lines were greater from 4.5 to 19 hours during which they produced 54.4% and 45.6%, respectively, of the controls. The data in this table are also presented in FIG. 19 in graphical form.

TABLE 1

| WOUND-INDUCED ETHYLENE SYNTHESIS IN pAG-5520 TRANSGENIC PLANTS | | |
|---|---|---|
| Plant ID | 4.5 hr. (nl/g/hr) | 4.5 to 19 hr. (nl/g/hr) |
| Control | 17.1 ± 2.7 | 5.7 ± 1.6 |
| E4-2 | 20.2 ± 0.42 | 5.1 ± 1.5 |
| E4-4 | 11.9 ± 1.3 | 3.1 ± 0.6 |
| E4-5 | 14.5 ± 0.5 | 2.6 ± 0.4 |
| E4-12 | 21.1 ± 5.1 | 5.4 ± 1.4 |

Error values are one standard deviation of the data (n=3).

C. Adometase mRNA Expression in Ripening Transgenic Fruit.

Expression of AdoMetase in ripening pAG-5520 tomato fruit was measured using an RNAse protection assay (RPA), as detailed in Example 10. Ripening fruit were harvested at four different stages, mature green (MG), breaker (Br), orange (Or) and ripe (Ri).

FIG. 20 displays the AdoMetase RNA expression level at each of these stages. FIG. 21 is a graphical representation of the same data, quantitated as described in Example 10 by liquid scintillation counting. Two of the transgenic lines assayed showed little or no expression of AdoMetase. Six other lines showed significant AdoMetase RNA expression, with the orange stage being predominant. In five of the six lines expressing AdoMetase, the expression level at the ripe stage was substantially diminished, demonstrating the transient nature of the E4-directed expression.

D. Western Blot Analysis of AdoMetase Expression.

Western blot analysis was carried out on protein extracts from E4-5 transgenic ripening tomatoes as detailed in Example 12. The results are shown in FIG. 22.

FIG. 22 shows the level of AdoMetase at four stages of fruit ripening. The pattern of expression matches that of AdoMetase transcription, including a decline in AdoMetase at the ripe stage. Known quantities of purified recombinant AdoMetase were run in the control lanes and used to establish a standard curve based on signal intensity. This allowed estimation of the relative amount of AdoMetase in these tomatoes and was calculated to be approximately 0.05% of the total soluble protein at the orange stage of ripening.

E. Ethylene Production in Ripening Transgenic Fruit.

Daily ethylene production by control and pAG-5520 transgenic fruit picked at the breaker stage was measured by sealing glass jars containing individual fruit and sampling 2 ml aliquots for gas chromatographic analysis, as detailed in Example 11. Measurements were made over a period of 15 days post-harvest.

The results of the analysis are presented in FIG. 23, which shows a comparison of fruit from one pAG-5520 transgenic line (E4-05) with the fruit from untransformed controls. The control values are represented as open squares, whereas the values from the transgenic line are represented as diamonds. The values are the average of ethylene determinations for three fruit. Error bars represent one standard deviation of the data.

In the transgenic line, the rate of ethylene production declines steeply immediately after harvest, reaching a minimum of approximately 1.0 nl/g/h at 7 days post-harvest. After this point, the rate increases to a level of approximately 2 to 3-fold the minimum and remains relatively constant. The kinetics of ethylene production from these transgenic tomatoes correlates with the observed AdoMetase RNA transcription and AdoMetase accumulation in the corresponding fruit. When AdoMetase expression is high the level of ethylene production is low, as expected.

The data represent a time period of fifteen days after the breaker stage of fruit ripening (post-breaker), and demonstrate a reduction in the amount of ethylene production in transgenic tomatoes versus normal fruit over the fifteen day period. Further, the data graphically illustrate the biological consequence of the transient nature of E4-driven Adometase expression described above.

The effect of AdoMetase gene expression on ripening has several dimensions, including (i) pAG-5520 tomatoes (transgenic line E4-12-D) develop color to a light red stage and then cease further color development, and (ii) the transgenic tomatoes remain firm for much longer than controls.

While the invention has been described with reference to specific methods and embodiments, it will be appreciated that various modifications and changes may be made without departing from the invention.

5,859,330

It is claimed:

1. A transgenic fruit-bearing plant, comprising:
(i) a DNA sequence encoding S-adenosylmethionine hydrolase, and operably linked to said DNA sequence (ii) a promoter selected from the group consisting of: a promoter of a tomato E4 gene, wherein said E4 gene is composed of a series of nucleotides that is at least 60% identical to that presented in SEQ ID NO: 8, a promoter of a tomato E8 gene, wherein said gene is composed of a series of nucleotides that is at least 60% identical to that presented in SEQ ID NO: 27, and an avocado cellulase gene promoter,
where expression regulated by the promoter is induced during fruit ripening or by ethylene synthesis by fruit produced by said plant.

2. A transgenic plant of claim 1, wherein the promoter comprises nucleotides 1–1173 of SEQ ID NO: 10.

3. A transgenic plant of claim 1, wherein the promoter is from a tomato E4 or E8 gene.

4. A transgenic plant of claim 1, wherein the promoter is an avocado cellulase gene promoter.

5. A method for modifying ripening fruit of a fruit bearing plant, comprising:
growing the plant of claim 1, to produce a transgenic plant bearing fruit, wherein fruit produced by said plant has an initial burst of ethylene production, followed by a reduction in the level of ethylene synthesis by said fruit, resulting in a fruit having a modified ripening phenotype in which the time course of ripening is delayed relative to wild-type fruit.

6. A fruit produced by the plant of claim 1.

7. A method for producing a transgenic fruit-bearing plant, where fruit produced by said plant has a modified ripening phenotype, comprising
introducing into progenitor cells of the plant a (i) DNA sequence encoding S-adenosylmethionine hydrolase, and operably linked to said DNA sequence (ii) a promoter selected from the group consisting of: a promoter of a tomato E4 gene, wherein said E4 gene is composed of a series of nucleotides that is at least 60% identical to that presented in SEQ ID NO: 8, a promoter of a tomato E8 gene, wherein said gene is composed of a series of nucleotides that is at least 60% identical to that presented in SEQ ID NO: 27, and an avocado cellulase gene promoter,
where expression regulated by said promoter is induced during fruit ripening or by ethylene synthesis by said fruit, and
growing the transformed progenitor cells to produce a transgenic plant bearing fruit, wherein fruit produced by said plant has an initial burst of ethylene production, followed by a reduction in the level of ethylene synthesis by said fruit, resulting in fruit having a modified ripening phenotype in which the time course of ripening is delayed over that of non-transformed fruit.

8. A method of claim 7, where said introducing includes transforming progenitor cells of the plant with a selectable vector containing said DNA sequence and said promoter.

9. A method of claim 7, wherein the promoter comprises nucleotides 1–1173 of SEQ ID NO: 10.

10. A method of claim 7, wherein the promoter is from a tomato E4 or E8 gene.

11. A method of claim 7, wherein the promoter is an avocado cellulase gene promoter.

12. An expression vector for use in transforming plant cells of a fruit-bearing plant, comprising
(i) a DNA sequence encoding S-adenosylmethionine hydrolase, and operably linked to said DNA sequence (ii) a promoter selected from the group consisting of: a promoter of a tomato E4 gene, wherein said E4 gene is composed of a series of nucleotides that is at least 60% identical to that presented in SEQ ID NO: 8, a promoter of a tomato E8 gene, wherein said gene is composed of a series of nucleotides that is at least 60% identical to that presented in SEQ ID NO: 27, and an avocado cellulase gene promoter,
where expression regulated by said promoter is induced during fruit ripening or by ethylene synthesis by said fruit.

13. A plant cell expression vector of claim 12, wherein the promoter comprises nucleotides 1–1173 of SEQ ID NO: 10.

14. A plant cell expression vector of claim 12, wherein the promoter is from a tomato E4 or E8 gene.

15. A plant cell expression vector of claim 12, wherein the promoter is an avocado cellulase gene promoter.

16. A kit for use in plant transformation, comprising the vector of claim 12.

17. A kit for use in transforming a fruit bearing plant, comprising the vector of claim 14.

18. A chimeric gene capable of expressing a polypeptide in a fruit-bearing plant, comprising
(i) a DNA sequence encoding S-adenosylmethionine hydrolase, and operably linked to said DNA sequence
(ii) a promoter selected from the group consisting of: a promoter of a tomato E4 gene, wherein said E4 gene is composed of a series of nucleotides that is at least 60% identical to that presented in SEQ ID NO: 8, a promoter of a tomato E8 gene, wherein said gene is composed of a series of nucleotides that is at least 60% identical to that presented in SEQ ID NO: 27, and an avocado cellulase gene promoter, where expression regulated by said promoter is induced during fruit ripening or by ethylene biosynthesis by fruit produced by said plant.

19. A plant cell containing the chimeric gene of claim 18.

20. A plant transformation vector containing the chimeric gene of claim 18.

21. A method for modifying ripening fruit of a fruit bearing plant, comprising:

growing the plant of claim 3, to produce a transgenic plant bearing fruit, wherein fruit produced by said plant has an initial burst of ethylene production, followed by a reduction in the level of ethylene synthesis by said fruit, resulting in a fruit having a modified ripening phenotype in which the time course of ripening is delayed relative to wild-type fruit.

22. A method for modifying ripening fruit of a fruit bearing plant, comprising:

growing the plant of claim 4, to produce a transgenic plant bearing fruit, wherein fruit produced by said plant has an initial burst of ethylene production, followed by a reduction in the level of ethylene synthesis by said fruit, resulting in a fruit having a modified ripening phenotype in which the time course of ripening is delayed relative to wild-type fruit.

23. A fruit produced by the plant of claim 3.

24. A fruit produced by the plant of claim 4.

25. A kit for use in transforming a fruit bearing plant, comprising the vector of claim 15.

26. A chimeric gene of claim 18, wherein the promoter is from a tomato E4 or E8 gene.

27. A chimeric gene of claim 18, wherein the promoter is an avocado cellulase gene promoter.

28. A plant cell containing the chimeric gene of claim 26.

29. A plant cell containing the chimeric gene of claim 27.

30. A transgenic plant of claim 1, wherein the nucleotide sequence of said promoter comprises SEQ ID NO: 24.

31. A transgenic plant of claim 1, wherein said promoter comprises nucleotide 1087 to nucleotide 2211 of SEQ ID NO:24.

32. A method of claim 7, wherein the nucleotide sequence of said promoter comprises SEQ ID NO: 24.

33. A method of claim 7, wherein said promoter comprises nucleotide 1087 to nucleotide 2211 of SEQ ID NO: 24.

34. An expression vector of claim 12, wherein the nucleotide sequence of said promoter comprises SEQ ID NO: 24.

35. An expression vector of claim 12, wherein said promoter comprises nucleotide 1087 to nucleotide 2211 of SEQ ID NO: 24.

* * * * *

UNITED STATES PATENT AND TRADEMARK OFFICE
CERTIFICATE OF CORRECTION

PATENT NO : 5,859,330
DATED : January 12, 1999
INVENTOR(S): R. Bestwick and A. Ferro It is certified that error appears in the above-identified patent and that said Letters Patent is hereby corrected as shown below:

On the title page, item [73] Assignee "Epitope, Inc." should read-- Agritope, Inc. --.

The designated assignee address "Beaverton, OR" should be -Portland, OR-.

Signed and Sealed this

Tenth Day of August, 1999

*Attest:*

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Figure 2 - top strand of synthetic
            oligo ( i x ) FEATURE:
        ( A ) NAME/KEY: CDS
        ( B ) LOCATION: 12..38

( x i ) SEQUENCE DESCRIPTION: SEQ ID NO:1:

```
GATCCGCCAC C ATG GTT TTC ACT AAA GAG CCT GCG AAC G          39
            Met Val Phe Thr Lys Glu Pro Ala Asn
             1               5
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Phe Thr Lys Glu Pro Ala Asn
 1               5
```

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Figure 2, bottom strand of synthetic
            oligo ( x i ) SEQUENCE DESCRIPTION: SEQ ID NO:3:

```
CGTTCGCAGG CTCTTTAGTG AAAACCATGG TGGCG          35
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid (C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Figure 16 - E4 promoter, 5'primer (xi) SEQUENCE DESCRIPTION: SEQ ID NO:4:

AGCCCATTGA AGCTTAAAGT AAACTT 26

(2) INFORMATION FOR SEQ ID NO:5:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Figure 16 - E4 promoter, 3'primer (xi) SEQUENCE DESCRIPTION: SEQ ID NO:5:

TACCCTCCAT GGCTCAATCT CT 22

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: E4 gene 5'primer (xi) SEQUENCE DESCRIPTION: SEQ ID NO:6:

ACGCATGGAG GGTAACAA 18

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: tomato E4 gene 3'primer (xi) SEQUENCE DESCRIPTION: SEQ ID NO:7:

GAAGCAAGAC AGCAAATG                                                                                      18

(2) INFORMATION FOR SEQ ID NO:8:

(i) SEQUENCE CHARACTERISTICS:
        (A) LENGTH: 2796 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: Figure 24 - E4 tomato gene DNA (ix) FEATURE:
        (A) NAME/KEY: CDS
        (B) LOCATION: 1439..1774

(ix) FEATURE:
        (A) NAME/KEY: exon
        (B) LOCATION: 1439..1774

(ix) FEATURE:
        (A) NAME/KEY: CDS
        (B) LOCATION: 1859..2113

(ix) FEATURE:
        (A) NAME/KEY: exon
        (B) LOCATION: 1859..2113

(ix) FEATURE:
        (A) NAME/KEY: intron
        (B) LOCATION: 1775..1858

(xi) SEQUENCE DESCRIPTION: SEQ ID NO:8:

```
GAATTCTCAA TTGAGCCCAA TTCAATCTCC AATTTCAACC CGTTTTAAAA CTTTTTATTA      60
AGATATGTTT CTATATTGAA AGTATGAATT ATTATCTATT TAACATCTTT TAGGATTTAT     120
CTATCCATTT GCTACTTTTT TAACAAAAAA TTCTTGAGTG AAAATTCAAA TTGTGATTAT     180
AAAAGTTAAA TATCAATATG TTAAATTATT AAGATTAATC GGGTCAAATT GGCGGGTCAA     240
GGCCCAATTC TTTTTTAGCC CATTTAAGCT CAAAGTAAAC TTGGGTGGGT CAAGACCCAA     300
CTCGATTTCT GTTCAACCCA TTTTAATATT TCTATTTTCA ACCTAACCCG CTCATTTGAT     360
ACCCCTACAA ATATCATATT TGTGTGTGAA ATATTTTTTG GGCTGGAGAG AGAGGCCCCG     420
AGGGGAGTGG AGGGGTGGGG TGGGAGAGA GAGCGAGAAA GAGTGGAGAG AGAAATTTGA     480
TATGAAATCC TACATATATT ACAGATTGTA ATGTTCTAAA CTATAACGAT TTGTCATAAA     540
CACATATCAT GGATTTGTCT TTTTGTGTAA TTTTCCCAAT TGTAAATAGG ACTTCGTTAT     600
TTGAAACTTG AAAGTGAAGT CACATAGATT AAGTACAAAC ATTAATTAAA GACCGTGGTG     660
GAATGATAAA TATTTATTTA TCTTTAATTA GTTATTTTTT TGGGAGCTCT TTATTCCAAT     720
GTGAGACTTT TGCGACATAT ATTCAAATTT AATCGAATCA CAATATGTAT TAGATTGATA     780
AAAAAATAAT TTTTTTACAA TGTTAGTTGA GACTCATAAC TTACTGCCTA TTGGTAATCT     840
ATGACTCCTA ATTCCTTAAT TATTTAAATA TATCATCTTG ATCGTTAACA AAGTAATTTC     900
GAAAGACCAC GAGTAAGAAG ACAAACGAGA ATACCAAAAA ATTCAAAAAT TAATGTGAT     960
TTGGTCAATC GATCTACGTC CATAAGGAG ATGAGTAATC TACTATAAAT ATGAGAGTAC    1020
AAAATACAGA GAGAAACAAC CTCAACTAAT TCACTCGGAA TACATGAGAA GTTCACACAA    1080
GTGATAACGT ATCAAACTTG TGACCCACAC TTTTCCCTCT AACCAAAGCT CTTAAAACTA    1140
```

-continued

```
TATTGTGAAT GCTGATTAAG TTAAACGAAA CAGTCCTAAA TCTTTTCCGT CCTATGAGAA      1200

ACAAGATTAA TCAATTCACA ATTTTTTTAA AAAGAAAAAC CTGTAAGAAA TTTAGGCAAA      1260

CAAAACCTAA CACAAGTTTG TTTTTGTTTT TACTACCAAC AAGAAATTCA AATGGCAAAT      1320

GTATAACGCA TCTTAGCTAA TTATATGACC AGATTCAGAT TAATATACAT CTTCACCCAT      1380

GCAATCCATT TCTATATAAA GAAACATACA CGAACTTGAT ATTATTAGAG ATTGAGCA       1438

ATG GAG GGT AAC AAC AGC AGT AGC AAG TCA ACC ACC AAT CCA GCA TTG      1486
Met Glu Gly Asn Asn Ser Ser Ser Lys Ser Thr Thr Asn Pro Ala Leu
 1               5                  10                  15

GAT CCG GAT CTG GAC AGC CCG GAT CAG CCG GGT CTG GAG TTT GCC CAA      1534
Asp Pro Asp Leu Asp Ser Pro Asp Gln Pro Gly Leu Glu Phe Ala Gln
            20                  25                  30

TTT GCT GCC GGC TGC TTT TGG GGA GTC GAA TTG GCT TTC CAG AGG GTT      1582
Phe Ala Ala Gly Cys Phe Trp Gly Val Glu Leu Ala Phe Gln Arg Val
        35                  40                  45

GGA GGA GTA GTG AAG ACG GAG GTT GGG TAC TCT CAG GGG AAT GTC CAT      1630
Gly Gly Val Val Lys Thr Glu Val Gly Tyr Ser Gln Gly Asn Val His
    50                  55                  60

GAC CCG AAC TAC AAG CTT ATT TGC TCC GGA ACA ACC GAA CAT GCC GAG      1678
Asp Pro Asn Tyr Lys Leu Ile Cys Ser Gly Thr Thr Glu His Ala Glu
65                  70                  75                  80

GCC ATT CGG ATC CAG TTT GAC CCG AAT GTC TGC CCG TAT TCC AAT CTC      1726
Ala Ile Arg Ile Gln Phe Asp Pro Asn Val Cys Pro Tyr Ser Asn Leu
                85                  90                  95

CTT TCT CTA TTT TGG AGT CGC CAT GAC CCG ACC ACT CTA AAT CGC CAG      1774
Leu Ser Leu Phe Trp Ser Arg His Asp Pro Thr Thr Leu Asn Arg Gln
            100                 105                 110

GTATCAAATT CCTTTGGTGT TTCATTTTAT GTGATTAATA TTAAAAATTT TTTATATAAA     1834

TGTCATGATG ATGGTTGTTG CTAG GGT AAT GAT GTG GGA AAG CAA TAC CGC       1885
                          Gly Asn Asp Val Gly Lys Gln Tyr Arg
                           1                   5

TCA GGA ATA TAT TAC TAT AAT GAT GCT CAG GCT CAA CTG GCA AGG GAG      1933
Ser Gly Ile Tyr Tyr Tyr Asn Asp Ala Gln Ala Gln Leu Ala Arg Glu
 10              15                  20                  25

TCG TTA GAA GCT AAG CAG AAG GAA TTT ATG GAT AAG AAA ATT GTC ACT      1981
Ser Leu Glu Ala Lys Gln Lys Glu Phe Met Asp Lys Lys Ile Val Thr
            30                  35                  40

GAA ATT CTT CCT GCT AAG AGA TTT TAT AGA GCT GAA GAG TAT CAC CAG      2029
Glu Ile Leu Pro Ala Lys Arg Phe Tyr Arg Ala Glu Glu Tyr His Gln
        45                  50                  55

CAA TAT CTA GAG AAG GGT GGG GGC AGA GGT TGT AAG CAG TCG GCT GCA      2077
Gln Tyr Leu Glu Lys Gly Gly Gly Arg Gly Cys Lys Gln Ser Ala Ala
    60                  65                  70

AAG GGC TGC AAT GAC CCA ATA AGG TGC TAC GGT TGACAGCAGA TCTTTGAATG    2130
Lys Gly Cys Asn Asp Pro Ile Arg Cys Tyr Gly
75                  80                  85

TCATAGCAAC TACAAAAGAA CTTGTTAGAC ATTTGCTGTC TTGCTTCTTT AAATTTGAAT    2190

AAACATGACA ATGATTCTTA TAACTACTTG CTCTCTTGGA TGGAATAACT AGTTGTCGTA    2250

AAGTATTCTC CTCTTGCTAA TTATTATCTC TCTTTATATG GTACCTGCAA TTTGTTGCTT    2310

TAGTTACAGA ATAATGGACG TCAATTCTAT ATCTTAATTT GTTTAAGTC TTAAATGAGG     2370

TGGTTTGTGT TTGAAAGCAA TATCAAGCAT AGTAATACCA ATGATTTAGT AGATGAACTT    2430

AATCAAATCA AATTCCAAAA TGCAGTCTAC AAATTGACAA CATGAAGTTA AGTGTATCTT    2490

ATGTAAATTG ACATCTTTCC TAGTAGATGC CTAATACTTT TGTAAAGACT AAAATAAGCA    2550

CAGATGAGGC TTGTGCATTT AACTTAGAGT TCATCCTTAG GTGTGGCTGC AGGAGACCCT    2610
```

```
GTAGGGTTGC TTGAAGTCTT GATGGGGTAG GAGGGTTGCA TTGCTATACC ACACAACCCC    2670

TCTTCAGCGT CAACCTTGCG CTGCATTCTA ATGTATCCTT TTTCTCCCCA TTCAGCTCCC    2730

CATGAGTTCT TCACAATCCA GTATTTGGTT CCATCGACGG TTGTGCCATA CCCCACAATA    2790

GCCACA                                                                 2796
```

( 2 ) INFORMATION FOR SEQ ID NO:9:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Glu Gly Asn Asn Ser Ser Ser Lys Ser Thr Thr Asn Pro Ala Leu
 1               5                   10                  15
Asp Pro Asp Leu Asp Ser Pro Asp Gln Pro Gly Leu Glu Phe Ala Gln
            20                  25                  30
Phe Ala Ala Gly Cys Phe Trp Gly Val Glu Leu Ala Phe Gln Arg Val
        35                  40                  45
Gly Gly Val Val Lys Thr Glu Val Gly Tyr Ser Gln Gly Asn Val His
    50                  55                  60
Asp Pro Asn Tyr Lys Leu Ile Cys Ser Gly Thr Thr Glu His Ala Glu
65                  70                  75                  80
Ala Ile Arg Ile Gln Phe Asp Pro Asn Val Cys Pro Tyr Ser Asn Leu
                85                  90                  95
Leu Ser Leu Phe Trp Ser Arg His Asp Pro Thr Thr Leu Asn Arg Gln
            100                 105                 110
Gly Asn Asp Val Gly Lys Gln Tyr Arg Ser Gly Ile Tyr Tyr Tyr Asn
        115                 120                 125
Asp Ala Gln Ala Gln Leu Ala Arg Glu Ser Leu Glu Ala Lys Gln Lys
    130                 135                 140
Glu Phe Met Asp Lys Lys Ile Val Thr Glu Ile Leu Pro Ala Lys Arg
145                 150                 155                 160
Phe Tyr Arg Ala Glu Glu Tyr His Gln Gln Tyr Leu Glu Lys Gly Gly
                165                 170                 175
Gly Arg Gly Cys Lys Gln Ser Ala Ala Lys Gly Cys Asn Asp Pro Ile
            180                 185                 190
Arg Cys Tyr Gly
            195
```

( 2 ) INFORMATION FOR SEQ ID NO:10:

( i ) SEQUENCE CHARACTERISTICS:
        ( A ) LENGTH: 1678 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Figure 25 - E4 tomato promoter /
            AdoMetase gene DNA ( i x ) FEATURE:
        ( A ) NAME/KEY: CDS (B) LOCATION: 1174..1629

(xi) SEQUENCE DESCRIPTION: SEQ ID NO:10:

| | | | | | |
|---|---|---|---|---|---|
| AAGCTTAAAG | TAAACTTGGG | TGGGTCAAGA | CCCAACTCGA | TTTCTGTTCA | ACCCATTTTA | 60 |
| ATATTTCTAT | TTTCAACCTA | ACCCGCTCAT | TTGATACCCC | TACAAATATC | ATATTTGTGT | 120 |
| GTGAAATATT | TTTTGGGCTG | GAGAGAGAGG | CCCCGAGGGG | AGTGGAGGGG | TGGGGTGGGG | 180 |
| AGAGAGAGCG | AGAAAGAGTG | GAGAGAGAAA | TTTGATATGA | AATCCTACAT | ATATTACAGA | 240 |
| TTGTAATGTT | CTAAACTATA | ACGATTTGTC | ATAAACACAT | ATCATGGATT | TGTCTTTTTG | 300 |
| TGTAATTTTC | CCAATTGTAA | ATAGGACTTC | GTTATTTGAA | ACTTGAAAGT | GAAGTCACAT | 360 |
| AGATTAAGTA | CAAACATTAA | TTAAAGACCG | TGGTGGAATG | ATAAATATTT | ATTTATCTTT | 420 |
| AATTAGTTAT | TTTTTTGGGA | GCTCTTTATT | CCAATGTGAG | ACTTTTGCGA | CATATATTCA | 480 |
| AATTTAATCG | AATCACAATA | TGTATTAGAT | TGATAAAAAA | ATAATTTTTT | TACAATGTTA | 540 |
| GTTGAGACTC | ATAACTTACT | GCCTATTGGT | AATCTATGAC | TCCTAATTCC | TTAATTATTT | 600 |
| AAATATATCA | TCTTGATCGT | TAACAAAGTA | ATTTCGAAAG | ACCACGAGTA | AGAAGACAAA | 660 |
| CGAGAATACC | AAAAAATTCA | AAAATTTAAT | GTGATTTGGT | CAATCGATCT | ACGTCCATAA | 720 |
| AGGAGATGAG | TAATCTACTA | TAAATATGAG | AGTACAAAAT | ACAGAGAGAA | ACAACCTCAA | 780 |
| CTAATTCACT | CGGAATACAT | GAGAAGTTCA | CACAAGTGAT | AACGTATCAA | ACTTGTGACC | 840 |
| CACACTTTTC | CCTCTAACCA | AAGCTCTTAA | AACTATATTG | TGAATGCTGA | TTAAGTTAAA | 900 |
| CGAAACAGTC | CTAAATCTTT | TCCGTCCTAT | GAGAACAAG | ATTAATCAAT | TCACAATTTT | 960 |
| TTAAAAAGA | AAAACCTGTA | AGAAATTTAG | GCAAACAAAA | CCTAACACAA | GTTTGTTTTT | 1020 |
| GTTTTTACTA | CCAACAAGAA | ATTCAAATGG | CAAATGTATA | ACGCATCTTA | GCTAATTATA | 1080 |
| TGACCAGATT | CAGATTAATA | TACATCTTCA | CCCATGCAAT | CCATTTCTAT | ATAAAGAAAC | 1140 |
| ATACACGAAC | TTGATATTAT | TAGAGATTGA | GCC ATG GTT TTC ACT AAA GAG CCT | | | 1194 |
| | | | Met Val Phe Thr Lys Glu Pro | | | |
| | | | 1 5 | | | |

| | | | | | | | | | | | | | | | |
|---|---|---|---|---|---|---|---|---|---|---|---|---|---|---|---|
| GCG | AAC | GTC | TTC | TAT | GTA | CTG | GTT | TCC | GCT | TTC | CGT | TCT | AAC | CTC | TGC | 1242 |
| Ala | Asn | Val | Phe | Tyr | Val | Leu | Val | Ser | Ala | Phe | Arg | Ser | Asn | Leu | Cys | |
| | | 10 | | | | 15 | | | | 20 | | | | | | |

| | | | | | | | | | | | | | | | |
|---|---|---|---|---|---|---|---|---|---|---|---|---|---|---|---|
| GAT | GAG | GTG | AAT | ATG | AGC | AGA | CAC | CGC | CAC | ATG | GTA | AGC | ACT | TTA | CGT | 1290 |
| Asp | Glu | Val | Asn | Met | Ser | Arg | His | Arg | His | Met | Val | Ser | Thr | Leu | Arg | |
| | 25 | | | | 30 | | | | | 35 | | | | | | |

| | | | | | | | | | | | | | | | |
|---|---|---|---|---|---|---|---|---|---|---|---|---|---|---|---|
| GCC | GCA | CCG | GGT | CTT | TAT | GGC | TCC | GTT | GAG | TCA | ACC | GAT | TTG | ACC | GGG | 1338 |
| Ala | Ala | Pro | Gly | Leu | Tyr | Gly | Ser | Val | Glu | Ser | Thr | Asp | Leu | Thr | Gly | |
| 40 | | | | | 45 | | | | 50 | | | | | | 55 | |

| | | | | | | | | | | | | | | | |
|---|---|---|---|---|---|---|---|---|---|---|---|---|---|---|---|
| TGC | TAT | CGT | GAG | GCA | ATC | TCA | AGC | GCA | CCA | ACT | GAG | GAA | AAA | ACT | GTT | 1386 |
| Cys | Tyr | Arg | Glu | Ala | Ile | Ser | Ser | Ala | Pro | Thr | Glu | Glu | Lys | Thr | Val | |
| | | | | 60 | | | | | 65 | | | | | 70 | | |

| | | | | | | | | | | | | | | | |
|---|---|---|---|---|---|---|---|---|---|---|---|---|---|---|---|
| CGT | GTA | CGC | TAC | AAG | GAC | AAA | GCG | CAG | CCA | CTC | AAT | GTT | GCA | CGC | CTA | 1434 |
| Arg | Val | Arg | Tyr | Lys | Asp | Lys | Ala | Gln | Pro | Leu | Asn | Val | Ala | Arg | Leu | |
| | | | 75 | | | | 80 | | | | | 85 | | | | |

| | | | | | | | | | | | | | | | |
|---|---|---|---|---|---|---|---|---|---|---|---|---|---|---|---|
| GCT | TCT | AAT | GAG | TGG | GAG | CAA | GAT | TGC | GTA | CTG | GTA | TAC | AAA | TCA | CAG | 1482 |
| Ala | Ser | Asn | Glu | Trp | Glu | Gln | Asp | Cys | Val | Leu | Val | Tyr | Lys | Ser | Gln | |
| | | 90 | | | | 95 | | | | 100 | | | | | | |

| | | | | | | | | | | | | | | | |
|---|---|---|---|---|---|---|---|---|---|---|---|---|---|---|---|
| ACT | CAC | ACG | GCT | GGT | CTG | GTG | TAC | GCT | AAA | GGT | ATC | GAC | GGG | TAT | AAG | 1530 |
| Thr | His | Thr | Ala | Gly | Leu | Val | Tyr | Ala | Lys | Gly | Ile | Asp | Gly | Tyr | Lys | |
| | 105 | | | | 110 | | | | | 115 | | | | | | |

| | | | | | | | | | | | | | | | |
|---|---|---|---|---|---|---|---|---|---|---|---|---|---|---|---|
| GCT | GAA | CGT | CTG | CCG | GGT | AGT | TTC | CAA | GAG | GTT | CCT | AAA | GGC | GCA | CCG | 1578 |
| Ala | Glu | Arg | Leu | Pro | Gly | Ser | Phe | Gln | Glu | Val | Pro | Lys | Gly | Ala | Pro | |
| 120 | | | | | 125 | | | | 130 | | | | | | 135 | |

| | | | | | | | | | | | | | | | |
|---|---|---|---|---|---|---|---|---|---|---|---|---|---|---|---|
| CTG | CAA | GGC | TGC | TTC | ACT | ATT | GAT | GAG | TTC | GGT | CGC | CGC | TGG | CAA | GTA | 1626 |
| Leu | Gln | Gly | Cys | Phe | Thr | Ile | Asp | Glu | Phe | Gly | Arg | Arg | Trp | Gln | Val | |

```
                        1 4 0                        1 4 5                        1 5 0
CAA  TAACGTGTTA  AACTCAAGGT  CATGCACGAT  GCGTGGCGGA  TCGGGTACC                      1 6 7 8
Gln
```

( 2 ) INFORMATION FOR SEQ ID NO:11:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Val  Phe  Thr  Lys  Glu  Pro  Ala  Asn  Val  Phe  Tyr  Val  Leu  Val  Ser
  1             5                       10                      15

Ala  Phe  Arg  Ser  Asn  Leu  Cys  Asp  Glu  Val  Asn  Met  Ser  Arg  His  Arg
            20                       25                      30

His  Met  Val  Ser  Thr  Leu  Arg  Ala  Ala  Pro  Gly  Leu  Tyr  Gly  Ser  Val
          35                       40                      45

Glu  Ser  Thr  Asp  Leu  Thr  Gly  Cys  Tyr  Arg  Glu  Ala  Ile  Ser  Ser  Ala
      50                       55                      60

Pro  Thr  Glu  Glu  Lys  Thr  Val  Arg  Val  Arg  Tyr  Lys  Asp  Lys  Ala  Gln
 65                      70                       75                          80

Pro  Leu  Asn  Val  Ala  Arg  Leu  Ala  Ser  Asn  Glu  Trp  Glu  Gln  Asp  Cys
                85                       90                       95

Val  Leu  Val  Tyr  Lys  Ser  Gln  Thr  His  Thr  Ala  Gly  Leu  Val  Tyr  Ala
              100                      105                     110

Lys  Gly  Ile  Asp  Gly  Tyr  Lys  Ala  Glu  Arg  Leu  Pro  Gly  Ser  Phe  Gln
            115                      120                     125

Glu  Val  Pro  Lys  Gly  Ala  Pro  Leu  Gln  Gly  Cys  Phe  Thr  Ile  Asp  Glu
          130                      135                     140

Phe  Gly  Arg  Arg  Trp  Gln  Val  Gln
145                      150
```

( 2 ) INFORMATION FOR SEQ ID NO:12:

( i ) SEQUENCE CHARACTERISTICS:
        ( A ) LENGTH: 225 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Figure 25 - raspberry E4 gene DNA ( i x ) FEATURE:
        ( A ) NAME/KEY: CDS
        ( B ) LOCATION: 1..213

( x i ) SEQUENCE DESCRIPTION: SEQ ID NO:12:

```
GAG  CTC  AGG  TTT  CAG  CGA  GTG  GCC  GGT  GTG  GTC  AAG  ACC  GAG  GTT  GGG       4 8
Glu  Leu  Arg  Phe  Gln  Arg  Val  Ala  Gly  Val  Val  Lys  Thr  Glu  Val  Gly
  1             5                       10                      15

TAC  TCC  CAG  GGC  CAC  GTC  CAC  GAT  CCG  AAT  TAC  AAA  CTG  GTC  TGC  TCC       9 6
Tyr  Ser  Gln  Gly  His  Val  His  Asp  Pro  Asn  Tyr  Lys  Leu  Val  Cys  Ser
            20                       25                      30

GGA  ACT  ACC  AAC  CAT  TCG  GAG  GTC  GTT  CGG  GTC  CAG  TTC  GAC  CCG  CAA      1 4 4
```

```
Gly Thr Thr Asn His Ser Glu Val Val Arg Val Gln Phe Asp Pro Gln
         35                  40                      45

GTC TAC CCA TAC TCG GAC CTG CTT TCC GTC TTT TGG TCT CGT CAT GAT         192
Val Tyr Pro Tyr Ser Asp Leu Leu Ser Val Phe Trp Ser Arg His Asp
     50                      55                  60

CCA ACG ACT GTC AAT CGC CAG GTATGGGGAT TG                                225
Pro Thr Thr Val Asn Arg Gln
 65                      70
```

(2) INFORMATION FOR SEQ ID NO:13:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:13:

```
Glu Leu Arg Phe Gln Arg Val Ala Gly Val Val Lys Thr Glu Val Gly
 1               5                  10                      15

Tyr Ser Gln Gly His Val His Asp Pro Asn Tyr Lys Leu Val Cys Ser
         20                  25                      30

Gly Thr Thr Asn His Ser Glu Val Val Arg Val Gln Phe Asp Pro Gln
         35                  40                      45

Val Tyr Pro Tyr Ser Asp Leu Leu Ser Val Phe Trp Ser Arg His Asp
     50                      55                  60

Pro Thr Thr Val Asn Arg Gln
 65                      70
```

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: original T3 sequence (xi) SEQUENCE DESCRIPTION: SEQ ID NO:14:

CACCAAATGA                                        10

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Kozak sequence (xi) SEQUENCE DESCRIPTION: SEQ ID NO:15:

GCCACCATGG                                                                                                              10

( 2 ) INFORMATION FOR SEQ ID NO:16:

( i ) SEQUENCE CHARACTERISTICS:
            ( A ) LENGTH: 81 base pairs
            ( B ) TYPE: nucleic acid
            ( C ) STRANDEDNESS: double
            ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
            ( C ) INDIVIDUAL ISOLATE: Fig. 2, first DNA sequence ( i x ) FEATURE:
            ( A ) NAME/KEY: CDS
            ( B ) LOCATION: 49..81

( x i ) SEQUENCE DESCRIPTION: SEQ ID NO:16:

AAGCTTGCAT  GCCTGCAGGT  CGACTCTAGA  GGATCCCCGT  AACACCAA ATG ATT TTC        57
                                                                               Met Ile Phe
                                                                                 1

ACT AAA GAG CCT GCG AAC GTC TTC                                                              81
Thr Lys Glu Pro Ala Asn Val Phe
    5                    10

( 2 ) INFORMATION FOR SEQ ID NO:17:

( i ) SEQUENCE CHARACTERISTICS:
            ( A ) LENGTH: 11 amino acids
            ( B ) TYPE: amino acid
            ( D ) TOPOLOGY: linear ( i i ) MOLECULE TYPE: protein ( x i ) SEQUENCE DESCRIPTION: SEQ ID NO:17:

Met Ile Phe Thr Lys Glu Pro Ala Asn Val Phe
  1                 5                   10

( 2 ) INFORMATION FOR SEQ ID NO:18:

( i ) SEQUENCE CHARACTERISTICS:
            ( A ) LENGTH: 12 base pairs
            ( B ) TYPE: nucleic acid
            ( C ) STRANDEDNESS: double
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
            ( C ) INDIVIDUAL ISOLATE: Fig. 2, T3 SAMase ( x i ) SEQUENCE DESCRIPTION: SEQ ID NO:18:

CACCAAATGA TT                                                                                           12

( 2 ) INFORMATION FOR SEQ ID NO:19:

( i ) SEQUENCE CHARACTERISTICS:
            ( A ) LENGTH: 12 base pairs
            ( B ) TYPE: nucleic acid
            ( C ) STRANDEDNESS: double
            ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Fig. 2, SAM- K ( x i ) SEQUENCE DESCRIPTION: SEQ ID NO:19:

GCCACCATGG TT 12

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 3, E8 5'primer ( x i ) SEQUENCE DESCRIPTION: SEQ ID NO:20:

GGTCTAGAAG GAATTTCACG 20

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 3, E8 3'primer ( x i ) SEQUENCE DESCRIPTION: SEQ ID NO:21:

ATTCACAGTG CAAAAGACCA TGGAA 25

( 2 ) INFORMATION FOR SEQ ID NO:22:

( i ) SEQUENCE CHARACTERISTICS:
        ( A ) LENGTH: 586 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Fig. 11, pUC19-SAM-K ( i x ) FEATURE:
        ( A ) NAME/KEY: CDS
        ( B ) LOCATION: 66..521

( x i ) SEQUENCE DESCRIPTION: SEQ ID NO:22:

```
ACAGCTATGA CCATGATTAC GCCAAGCTTG CATGCCTGCA GGTCGACTCT AGAGGATCCG                    60

CCACC ATG GTT TTC ACT AAA GAG CCT GCG AAC GTC TTC TAT GTA CTG                       107
      Met Val Phe Thr Lys Glu Pro Ala Asn Val Phe Tyr Val Leu
       1           5                   10

GTT TCC GCT TTC CGT TCT AAC CTC TGC GAT GAG GTG AAT ATG AGC AGA                     155
Val Ser Ala Phe Arg Ser Asn Leu Cys Asp Glu Val Asn Met Ser Arg
 15              20                  25                      30

CAC CGC CAC ATG GTA AGC ACT TTA CGT GCC GCA CCG GGT CTT TAT GGC                     203
His Arg His Met Val Ser Thr Leu Arg Ala Ala Pro Gly Leu Tyr Gly
             35                  40                      45

TCC GTT GAG TCA ACC GAT TTG ACC GGG TGC TAT CGT GAG GCA ATC TCA                     251
Ser Val Glu Ser Thr Asp Leu Thr Gly Cys Tyr Arg Glu Ala Ile Ser
             50                  55                      60

AGC GCA CCA ACT GAG GAA AAA ACT GTT CGT GTA CGC TAC AAG GAC AAA                     299
Ser Ala Pro Thr Glu Glu Lys Thr Val Arg Val Arg Tyr Lys Asp Lys
         65                  70                  75

GCG CAG GCA CTC AAT GTT GCA CGC CTA GCT TGT AAT GAG TGG GAG CAA                     347
Ala Gln Ala Leu Asn Val Ala Arg Leu Ala Cys Asn Glu Trp Glu Gln
         80                  85                  90

GAT TGC GTA CTG GTA TAC AAA TCA CAG ACT CAC ACG GCT GGT CTG GTG                     395
Asp Cys Val Leu Val Tyr Lys Ser Gln Thr His Thr Ala Gly Leu Val
 95              100                 105                     110

TAC GCT AAA GGT ATC GAC GGG TAT AAG GCT GAA CGT CTG CCG GGT AGT                     443
Tyr Ala Lys Gly Ile Asp Gly Tyr Lys Ala Glu Arg Leu Pro Gly Ser
             115                 120                     125

TTC CAA GAG GTT CCT AAA GGC GCA CCG CTG CAA GGC TGC TTC ACT ATT                     491
Phe Gln Glu Val Pro Lys Gly Ala Pro Leu Gln Gly Cys Phe Thr Ile
             130                 135                     140

GAT GAG TTC GGT CGC CGC TGG CAA GTA CAA TAAGTGTTAA ACTCAAGGTC                       541
Asp Glu Phe Gly Arg Arg Trp Gln Val Gln
             145                 150

ATGCACGATG CGTGGCGGAT CGGGTACCGA GCTCGAATTC ACTGG                                   586
```

(2) INFORMATION FOR SEQ ID NO:23:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:23:

```
Met Val Phe Thr Lys Glu Pro Ala Asn Val Phe Tyr Val Leu Val Ser
 1               5                   10                      15

Ala Phe Arg Ser Asn Leu Cys Asp Glu Val Asn Met Ser Arg His Arg
             20                  25                      30

His Met Val Ser Thr Leu Arg Ala Ala Pro Gly Leu Tyr Gly Ser Val
             35                  40                      45

Glu Ser Thr Asp Leu Thr Gly Cys Tyr Arg Glu Ala Ile Ser Ser Ala
         50                  55                      60

Pro Thr Glu Glu Lys Thr Val Arg Val Arg Tyr Lys Asp Lys Ala Gln
 65                  70                  75                  80

Ala Leu Asn Val Ala Arg Leu Ala Cys Asn Glu Trp Glu Gln Asp Cys
             85                  90                      95

Val Leu Val Tyr Lys Ser Gln Thr His Thr Ala Gly Leu Val Tyr Ala
             100                 105                     110

Lys Gly Ile Asp Gly Tyr Lys Ala Glu Arg Leu Pro Gly Ser Phe Gln
             115                 120                     125
```

Glu Val Pro Lys Gly Ala Pro Leu Gln Gly Cys Phe Thr Ile Asp Glu
    130             135             140

Phe Gly Arg Arg Trp Gln Val Gln
145             150

( 2 ) INFORMATION FOR SEQ ID NO:24:

( i ) SEQUENCE CHARACTERISTICS:
        ( A ) LENGTH: 2216 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 13, E8 promoter ( x i ) SEQUENCE DESCRIPTION: SEQ ID NO:24:

| | | | | | |
|---|---|---|---|---|---|
| GAATTCATTT | TTGACATCCC | TAATGATATT | GTTCACGTAA | TTAAGTTTTG | TGGAAGTGAG | 60 |
| AGAGTCCAAT | TTTGATAAGA | AAAGAGTCAG | AAAACGTAAT | ATTTTAAAAG | TCTAAATCTT | 120 |
| TCTACAAATA | AGAGCAAATT | TATTTATTTT | TTAATCCAAT | AAATATTAAT | GGAGGACAAA | 180 |
| TTCAATTCAC | TTGGTTGTAA | AATAAACTTA | AACCAATAAC | CAAAGANCTA | ATAAATCTGA | 240 |
| AGTGGAATTA | TTAAGGATAA | TGTACATAGA | CAATGAAGAA | ATAATAGGTT | CGATGAATTA | 300 |
| ATAATAATTA | AGGATGTTAC | AATCATCATG | TGCCAAGTAT | ATACACAATA | TTCTATGGGA | 360 |
| TTTATAATTT | CGTTACTTCA | CTTAACTTTT | GCGTAAATAA | AACGAATTAT | CTGATATTTT | 420 |
| ATAATAAAAC | AGTTAATTAA | GAACCATCAT | TTTTAACAAC | ATAGATATAT | TATTTCTAAT | 480 |
| AGTTTAATGA | TACTTTTAAA | TCTTTTAAAT | TTTATGTTTC | TTTTAGAAAA | TAAAAATTCA | 540 |
| AAAAAATTAA | ATATATTTAC | AAAAACTACA | ATCAAACACA | ACTTCATATA | TTAAAAGCAA | 600 |
| AATATATTTT | GAAAATTTCA | AGTGTCCTAA | CAAATAAGAC | AAGAGGAAAA | TGTACGATGA | 660 |
| GAGACATAAA | GAGAACTAAT | AATTGAGGAG | TCCTATAATA | TATAATAAAG | TTTATTAGTA | 720 |
| AACTTAATTA | TTAAGGACTC | CTAAAATATA | TGATAGGAGA | AAATGAATGG | TGAGAGATAT | 780 |
| TGGAAAACTT | AATAATTAAG | GATNTTAAAA | TATATGGTAA | AAGATAGGCA | AAGTATCCAT | 840 |
| TATCCCCTTT | TAACTTGAAG | TCTACCTAGG | CGCATGTGAA | AGGTTGATTT | TTTGTCACGT | 900 |
| CATATAGCTA | TAACGTAAAA | AAAGAAAGTA | AAATTTTTAA | TTTTTTTTAA | TATATGACAT | 960 |
| ATTTTAAACG | AAATATAGGA | CAAAATGTAA | ATGAATAGTA | AAGGAAACAA | AGATTAATAC | 1020 |
| TTACTTTGTA | AGAATTTAAG | ATAAATTTAA | AATTTAATAG | ATCAACTTTA | CGTCTAGAAA | 1080 |
| GACCCATATC | TAGAAGGAAT | TTCACGAAAT | CGGCCCTTAT | TCAAAAATAA | CTTTTAAATA | 1140 |
| ATGAATTTTA | AATTTAAGA | AATAATATCC | AATGAATAAA | TGACATGTAG | CATTTTACCT | 1200 |
| AAATATTTCA | ACTATTTTAA | TCCAATATTA | ATTTGTTTTA | TTCCAACAA | TAGAAAGTCT | 1260 |
| TGTGCAGACA | TTTAATCTGA | CTTTTCCAGT | ACTAAATATT | AATTTTCTGA | AGATTTTCGG | 1320 |
| GTTTAGTCCA | CAAGTTTTAG | TGAGAAGTTT | TGCTCAAAAT | TTTAGGTGAG | AAGGTTTGAT | 1380 |
| ATTTATCTTT | TGTTAAATTA | ATTTATCTAG | GTGACTATTA | TTTATTTAAG | TAGAAATTCA | 1440 |
| TATCATTACT | TTTGCCAACT | TGTAGTCATA | ATAGGAGTAG | GTGTATATGA | TGAAGGAATA | 1500 |
| AACAAGTTCA | GTGAAGTGAT | TAAAATAAAA | TATAATTTAG | GTGTACATCA | AATAAAAACC | 1560 |
| TTAAAGTTTA | GAAAGGCACC | GAATAATTTT | GCATAGAAGA | TATTAGTAAA | TTTATAAAAA | 1620 |

| | | | | | | |
|---|---|---|---|---|---|---|
| TAAAAGAAAT | GTAGTTGTCA | AGTTGTCTTC | TTTTTTTGG | ATAAAAATAG | CAGTTGGCTT | 1680 |
| ATGTCATTCT | TTTACAACCT | CCATGCCACT | TGTCCAATTG | TTGACACTTA | ACTAATTAGT | 1740 |
| TTGATTCATG | TATGAATACT | AAATAATTTT | TTAGGACTGA | CTCAAATATT | TTTATATTAT | 1800 |
| CATAGTAATA | TTTATCTAAT | TTTTAGGACC | ACTTATTACT | AAATAATAAA | TTAACTACTA | 1860 |
| CTATATTATT | GTTGTGAAAC | AACAACGTTT | TGGTTGTTAT | GATGAAACGT | ACACTATATC | 1920 |
| AGTATGAAAA | ATTCAAAACG | ATTAGTATAA | ATTATATTGA | AAATTTGATA | TTTTTCTATT | 1980 |
| CTTAATCAGA | CGTATTGGGT | TTCATATTTT | AAAAGGGAC | TAAACTTAGA | AGAGAAGTTT | 2040 |
| GTTTGAAACT | ACTTTTGTCT | CTTTCTTGTT | CCCATTTCTC | TCTTAGATTT | CAAAAAGTGA | 2100 |
| ACTACTTTAT | CTCTTTCTTT | GTTCACATTT | TATTTTATTC | TATTATAAAT | ATGGCATCCT | 2160 |
| CATATTGAGA | TTTTAGAAA | TTATTCTAAT | CATTCACAGT | GCAAAGACC | ATGGAA | 2216 |

( 2 ) INFORMATION FOR SEQ ID NO:25:

( i ) SEQUENCE CHARACTERISTICS:
        ( A ) LENGTH: 2708 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: RASPBERRY E4 GENE ( i x ) FEATURE:
        ( A ) NAME/KEY: misc_feature
        ( B ) LOCATION: 1468..1469
        ( D ) OTHER INFORMATION: /note= "small sequencing gap of
            unknown size"

( x i ) SEQUENCE DESCRIPTION: SEQ ID NO:25:

| | | | | | | |
|---|---|---|---|---|---|---|
| AAGCTTAATT | GAGATGATTA | GCCCAGACCC | AGCAGGATTA | GGCTTAATGG | TGGTCCATTT | 60 |
| GAGAAAAAGA | TTAAAAATGA | TGTCATAAAA | AAACNTGGTC | GBCAGGATTC | NAACCTGCGC | 120 |
| GGGCAAAGCC | ACATGATTTC | TAGTCATGCC | CGATAACCAC | TCCGGCACGA | CCACAATGAT | 180 |
| GCTACAATTG | CTTTGTTGTA | ATCATTAACT | TATGGTTGAG | TTTGATGCTG | ATTAATACTA | 240 |
| TTATGTTTCC | ATTAACTACT | TTGAAGTAT | ACAAAATTAC | GAATTTATAA | CCAAATTTGA | 300 |
| GGTATAATAT | GCGAGAGCTA | CCTAAATTTT | TCTTACTTAA | TTTTAAAGTA | CATTCAAATT | 360 |
| CTGAATTTAT | ATTGTGTATA | GTCAGAAAAC | AATCTACATA | TTTAAACACA | TAAATTTCTC | 420 |
| ACGTTTATAA | TCAATTTTGT | CGGTTCCTGT | AATTTTTCTA | AAATAAAAAG | CAACCAAAAT | 480 |
| TGTGCATCAA | CTTATTACAT | ACCATGGGAA | ATGCAAACTT | CAAAACTTAT | GGACTCAAAG | 540 |
| GGTACATATC | TAAACTACAT | ATTGTCAGAT | TCTTCACTCT | TATTTCTTGA | GGGCCTCGAG | 600 |
| GCATTACCAA | CCAAATCCAA | AAATTGCTTT | CGAATCTCAA | TAAAAGGAT | AACCCCATGA | 660 |
| AAAAGACGTG | GACGGCAGGA | TTCGAACCTG | CGCGCAGAGC | CCACATGATT | TCTAGTCATG | 720 |
| CCCGATAACC | ACTCCGGCAC | GTCCACTTCA | CTGTTAACGT | TTACAGTAAC | AAGTCACTAA | 780 |
| CTACTAATCA | ACATTAGCTC | AGGAAATCAA | AACTAGATTA | TTTACATTTA | CAACGACATG | 840 |
| TCGTTCGAAG | TAGTTGGTCT | GTATCTGAGT | AGCTTGGCG | GGTAGATTCA | ATCGCATTTC | 900 |
| TGCATATAAA | ACTGATCCTC | CCTCTATCGC | CAAAGTCAAA | CTGAAAATGG | CTTCCACCAC | 960 |
| CACCAACAAC | CCAGCTCTAG | ACCCAGATTC | GGACACTCCG | GATAATCCGG | GTCACGAGTT | 1020 |

| | | | | | | |
|---|---|---|---|---|---|---|
| TGCTCAATTC | GGATCCGGGT | GCTTCTGGGG | AGCCGAGCTC | AGGTTTCAGC | GAGTGGCCGG | 1080 |
| TGTGGTCAAG | ACCGAGGTTG | GGTACTCCCA | GGGCCACGTC | CACGATCCGA | ATTACAAACT | 1140 |
| GGTCTGCTCC | GGAACTACCA | ACCATTCGGA | GGTCGTTCGG | GTCCAGTTCG | ACCCGCAAGT | 1200 |
| CTACCCATAC | TCGGACCTGC | TTTCCGTCTT | TTGGTCTCGT | CATGATCCAA | CGACTGTCAA | 1260 |
| TCGCCAGGTA | TGGGGATTGG | GGACTTCTGT | TTTCATTTGA | ATTTGATGC | TAAAAAATTT | 1320 |
| CTTGCTTTTT | CATACTACAC | AGTACACACA | AAAAGTTGTG | TTTTTTTTCA | TTCTTTTAAA | 1380 |
| TAGTAGTTGG | AAAAGTGCTC | TTGGAGTTGA | AGAGTACTTC | AGTATTGCAT | ATGGTCTCAG | 1440 |
| TGAAATGATA | GTGATTATCA | TAAGGAGTTT | AAAGGCAGGA | TGCATTTGT | GTATGANTGA | 1500 |
| TTTTGGGTAG | AATATTTTG | GAACAGTTAA | AATTTATGGG | CTGCTGCACA | CTGGCTATGA | 1560 |
| ACAAATGTAT | AGCATTAAAG | TGCTTATGAC | AAATTCACAA | TTGTATATTA | GCAGCAGAGA | 1620 |
| CATTAAAGTT | TCTAAATGCC | TTTTAAGTAG | ATTGGAAAAA | AGTGCTTTTT | TTGGTTGAAG | 1680 |
| AAGCACATTC | ACTATTTGCC | TGTTAATGGA | ATTGGTAATG | ATGAATCACA | AGGATATTTG | 1740 |
| TGAATACAAG | CAGGATGCTT | TTAGTGTGCA | AGTGATCTTT | CGGAACATTT | AAAATCGTCA | 1800 |
| TAACAAAGGT | GTAACATAAG | AAGGCTTTGA | AATATTCTCA | ATTTCTCATT | GATTGAATGA | 1860 |
| ATTATGTGTT | AGGGTGGAGA | TGTGGGTACT | CAATATCGAT | CTGGAATATA | CTACTACAAC | 1920 |
| GAAACGCAGG | CCCGTCTAGC | ACAGGAATCA | AAGGAAGCAA | AGCAACTGGA | GTTTAAGGAT | 1980 |
| AAGAAGGTGG | TGACAGAGAT | TCTTCCAGCA | AAGAGGTTTT | ACAGGGCAGA | GGAGTACCAT | 2040 |
| CAGCAATATC | TCGCAAAGGG | AGGAGGTAAT | GGCAACAAAC | AATCTGCTGA | AAAAGGTTGC | 2100 |
| AATGATCCTA | TTCGATGCTA | TGGTTGAGAA | ACTAATGCAT | TATGCCATTA | TTAAAACTCT | 2160 |
| ACTGGTTTAC | TATGCAGAAA | CACCTATGTC | AGTTCAATTA | TACTGAAGGC | ACCAAAGTGT | 2220 |
| CATCTTAAAT | TATATGGCAA | TGTTTTACTC | GTTATGAATA | AAGGAGGTCC | AAGTCGACCA | 2280 |
| GATATGAACA | AATGAAATAT | TGCCATGTTA | ATTGGAATCC | AGTAGTAATT | AGGATTTGTT | 2340 |
| TTGGTGTATG | TACTCCGATA | TCAAGATATG | CAAATGATGC | ATTGTGTTTT | TATATATTGA | 2400 |
| CAAGTTCCAA | ATTATAGTAC | TTCGTATGTG | TTATGCGGTT | TAATTAGTGT | TGCTTACTTG | 2460 |
| AATGGTATAT | TACTATTATG | CTTAGTAGGA | ACTAGGAACT | AGGGAATATG | TTGTGATAGA | 2520 |
| GTTGTCCAAC | GAAATTTTTG | ACCAAAGTTA | TTTCATTGAA | TAAAAACTAC | AGTCTTAGAG | 2580 |
| ATACATCCAA | TTCTATAAAG | TGAAAGAAGC | AAATATTATT | TGTTCATGAG | CTATGAGTC | 2640 |
| ATGAACTTTA | TGCTATAACC | GAAGCAACCT | CAGAAAAGTC | GAAGTAAATT | GTGTATTGTT | 2700 |
| TAGAGCTC | | | | | | 2708 |

( 2 ) INFORMATION FOR SEQ ID NO:26:

( i ) SEQUENCE CHARACTERISTICS:
        ( A ) LENGTH: 191 amino acids
        ( B ) TYPE: amino acid
        ( C ) STRANDEDNESS: double
        ( D ) TOPOLOGY: linear ( i i ) MOLECULE TYPE: protein ( i i i ) HYPOTHETICAL: NO ( i v ) ANTI-SENSE: NO ( v ) ORIGINAL SOURCE:
        ( C ) INDIVIDUAL ISOLATE: RASPBERRY E4 PROTEIN ( x i ) SEQUENCE DESCRIPTION: SEQ ID NO:26:

Met  Ala  Ser  Thr  Thr  Thr  Asn  Asn  Pro  Ala  Leu  Asp  Pro  Asp  Ser  Asp

|  | 1 |  |  |  | 5 |  |  |  |  | 10 |  |  |  |  | 15 |  |
|---|---|---|---|---|---|---|---|---|---|---|---|---|---|---|---|---|
| Thr | Pro | Asp | Asn | Pro | Gly | His | Glu | Phe | Ala | Gln | Phe | Gly | Ser | Gly | Cys |
|  |  |  | 20 |  |  |  |  | 25 |  |  |  |  | 30 |  |  |
| Phe | Trp | Gly | Ala | Glu | Leu | Arg | Phe | Gln | Arg | Val | Ala | Gly | Val | Val | Lys |
|  |  | 35 |  |  |  |  | 40 |  |  |  |  | 45 |  |  |  |
| Thr | Glu | Val | Gly | Tyr | Ser | Gln | Gly | His | Val | His | Asp | Pro | Asn | Tyr | Lys |
|  | 50 |  |  |  |  | 55 |  |  |  |  | 60 |  |  |  |  |
| Leu | Val | Cys | Ser | Gly | Thr | Thr | Asn | His | Ser | Glu | Val | Val | Arg | Val | Gln |
| 65 |  |  |  |  | 70 |  |  |  |  | 75 |  |  |  |  | 80 |
| Phe | Asp | Pro | Gln | Val | Tyr | Pro | Tyr | Ser | Asp | Leu | Leu | Ser | Val | Phe | Trp |
|  |  |  |  | 85 |  |  |  |  | 90 |  |  |  |  | 95 |  |
| Ser | Arg | His | Asp | Pro | Thr | Thr | Val | Asn | Arg | Gln | Gly | Gly | Asp | Val | Gly |
|  |  |  | 100 |  |  |  |  | 105 |  |  |  |  | 110 |  |  |
| Thr | Gln | Tyr | Arg | Ser | Gly | Ile | Tyr | Tyr | Asn | Glu | Thr | Gln | Ala | Arg |  |
|  |  | 115 |  |  |  |  | 120 |  |  |  |  | 125 |  |  |  |
| Leu | Ala | Gln | Glu | Ser | Lys | Glu | Ala | Lys | Gln | Leu | Glu | Phe | Lys | Asp | Lys |
|  | 130 |  |  |  |  | 135 |  |  |  |  | 140 |  |  |  |  |
| Lys | Val | Val | Thr | Glu | Ile | Leu | Pro | Ala | Lys | Arg | Phe | Tyr | Arg | Ala | Glu |
| 145 |  |  |  |  | 150 |  |  |  |  | 155 |  |  |  |  | 160 |
| Glu | Tyr | His | Gln | Gln | Tyr | Leu | Ala | Lys | Gly | Gly | Gly | Asn | Gly | Asn | Lys |
|  |  |  |  | 165 |  |  |  |  | 170 |  |  |  |  | 175 |  |
| Gln | Ser | Ala | Glu | Lys | Gly | Cys | Asn | Asp | Pro | Ile | Arg | Cys | Tyr | Gly |  |
|  |  |  | 180 |  |  |  |  | 185 |  |  |  |  | 190 |  |  |

( 2 ) INFORMATION FOR SEQ ID NO:27:

( i ) SEQUENCE CHARACTERISTICS:
        ( A ) LENGTH: 3042 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Solanum lycopersicum ( v i i ) IMMEDIATE SOURCE:
        ( A ) LIBRARY: charon 35
        ( B ) CLONE: lambda E8-3

( i x ) FEATURE:
        ( A ) NAME/KEY: promoter
        ( B ) LOCATION: 1002..1014

( i x ) FEATURE:
        ( A ) NAME/KEY: TATA_signal
        ( B ) LOCATION: 1055..1063

( i x ) FEATURE:
        ( A ) NAME/KEY: polyA_signal
        ( B ) LOCATION: 2830..2836

( x ) PUBLICATION INFORMATION:
        ( A ) AUTHORS: Deikman, Jill
                     Fischer, Robert L.
        ( C ) JOURNAL: EMBO J.
        ( D ) VOLUME: 7
        ( E ) ISSUE: 11
        ( F ) PAGES: 3315-3320
        ( G ) DATE: 1988

( x i ) SEQUENCE DESCRIPTION: SEQ ID NO:27:

| | | | | | | |
|---|---|---|---|---|---|---|
|CTAGAAGGAA|TTTCACGAAA|TCGGCCCTTA|TTCAAAAATA|ACTTTTAAAT|AATGAATTTT|60|
|AAATTTTAAG|AAATAATATC|CAATGAATAA|ATGACATGTA|GCATTTTACC|TAAATATTTC|120|
|AACTATTTTA|ATCCAATATT|AATTTGTTTT|ATTCCCAACA|ATAGAAAGTC|TTGTGCAGAC|180|
|ATTTAATCTG|ACTTTTCCAG|TACTAAATAT|TAATTTTCTG|AAGATTTTCG|GGTTTAGTCC|240|
|ACAAGTTTTA|GTGAGAAGTT|TTGCTCAAAA|TTTTAGGTGA|GAAGGTTTGA|TATTTATCTT|300|
|TTGTTAAATT|AATTTATCTA|GGTGACTATT|ATTTATTTAA|GTAGAAATTC|ATATCATTAC|360|
|TTTTGCCAAC|TTGTAGTCAT|AATAGGAGTA|GGTGTATATG|ATGAAGGAAT|AAACAAGTTC|420|
|AGTGAAGTGA|TTAAAATAAA|ATATAATTTA|GGTGTACATC|AAATAAAAAC|CTTAAAGTTT|480|
|AGAAAGGCAC|CGAATAATTT|TGCATAGAAG|ATATTAGTAA|ATTTATAAAA|ATAAAAGAAA|540|
|TGTAGTTGTC|AAGTTGTCTT|CTTTTTTTTG|GATAAAAATA|GCAGTTGGCT|TATGTCATTC|600|
|TTTTACAACC|TCCATGCCAC|TTGTCCAATT|GTTGACACTT|AACTAATTAG|TTTGATTCAT|660|
|GTATGAATAC|TAAATAATTT|TTTAGGACTG|ACTCAAATAT|TTTTATATTA|TCATAGTAAT|720|
|ATTTATCTAA|TTTTTAGGAC|CACTTATTAC|TAAATAATAA|ATTAACTACT|ACTATATTAT|780|
|TGTTGTGAAA|CAACAACGTT|TTGGTTGTTA|TGATGAAACG|TACACTATAT|CAGTATGAAA|840|
|AATTCAAAAC|GATTAGTATA|AATTATATTG|AAAATTTGAT|ATTTTTCTAT|TCTTAATCAG|900|
|ACGTATTGGG|TTTCATATTT|TAAAAGGGA|CTAAACTTAG|AAGAGAAGTT|TGTTTGAAAC|960|
|TACTTTTGTC|TCTTTCTTGT|TCCCATTTCT|CTCTTAGATT|TCAAAAAGTG|AACTACTTTA|1020|
|TCTCTTTCTT|TGTTCACATT|TTATTTTATT|CTATTATAAA|TATGGCATCC|TCATATTGAG|1080|
|ATTTTTAGAA|ATTATTCTAA|TCATTCACAG|TGCAAAAGAA|GATGGAAAGC|CCTAGAGTTG|1140|
|AGGAGAGTTA|TGACAAAATG|AGTGAATTAA|AAGCGTTTGA|TGATACTAAG|GCCGGTGTTA|1200|
|AAGGACTTGT|TGATTCTGGA|ATTACTAAAG|TACCTCAAAT|ATTCGTTCTA|CCGCCAAAAG|1260|
|ACAGGGCTAA|AAAATGTGAA|ACACATTTCG|TTTTTCCAGT|GATAGACCTT|CAAGGTATCG|1320|
|ATGAGGATCC|GATTAAGCAT|AAGGAGATAG|TGGACAAAGT|TCGAGATGCA|TCGGAGAAAT|1380|
|GGGGTTTTTT|CCAAGTGGTT|AATCATGGGA|TTCCAACATC|CGTCTTGGAC|AGAACGTTGC|1440|
|AAGGAACACG|ACAGTTCTTT|GAGCAAGATA|ACGAGGTTAA|GAAACAGTAT|TACACTCGAG|1500|
|ATACTGCGAA|AAAAGTGGTT|TATACTAGCA|ATCTTGATTT|GTATAAATCT|TCTGTTCCAG|1560|
|CTGCAAGTTG|GAGAGACACG|ATTTTCTGTT|ACATGGCTCC|GAATCCTCCC|AGTCTACAAG|1620|
|AATTTCCAAC|TCCATGCGGG|TAAGTATTTT|CATTTCTTAG|TCTGGAGATT|CTTTAGTAGC|1680|
|TCAGTGGCAG|AGGCGGACCC|TCCGCCGTGC|TCGAGCACCC|ATTAATTTCG|TTACGGAATA|1740|
|TATATATATC|TACGTAGAAA|TTAATATGTA|TTTGTATAAA|ATTAACATAG|AGCACCCAAT|1800|
|GAATAAACGA|TTTAGTTGGC|CCAATGGCTC|CTGGATGAAT|ACTCTGTTAA|CACATATTTT|1860|
|TTATATTTTC|AGTTTAAATT|TCTAGATCCG|CCACTGCTCA|GTTGATTGAC|TATCTAAAGA|1920|
|CAGCAAAAAT|TCCTAGATCT|GTCGCTGCTC|AGTTGATTGA|GTATCTAAAT|ACAGCAAATT|1980|
|CTTAGATCCG|CCATTGCTTA|GTTGATTGAC|TATCTAAAGA|CGTCTGATTT|TATATAAAAA|2040|
|TATGTCATGT|TTCAATGCAG|GGAGTCATTA|ATAGACTTCT|CCAAGGATGT|GAAGAAACTG|2100|
|GGATTCACTT|TACTTGAATT|ATTGTCTGAA|GGTCTCGGTC|TCGATCGTAG|TTATCTCAAA|2160|
|GATTATATGG|ATTGTTTTCA|TCTTTTCTGT|TCTTGCAACT|ACTACCCACC|ATGTCCTCAG|2220|
|CCAGAACTCA|CCATGGGCAC|CATTCAACAT|ACCGATATTG|GTTTTGTAAC|GATCCTTCTA|2280|
|CAAGATGATA|TGGGAGGGCT|CCAAGTTCTT|CACCAGAATC|ATTGGGTTGA|TGTTCCTCCT|2340|
|ACACCCGGTT|CTCTAGTGGT|GAATATTGGA|GATTTTCTGC|AGGTTAGTAG|TCGATATTAT|2400|

-continued

| | | | | | | |
|---|---|---|---|---|---|---|
| ATACAAAGTT | TATCGCGCAA | CACATTTAGA | AAATCTTTTT | TTTAATTATT | TTTTGCAGCT | 2460 |
| CTTGTCAAAT | GACAAGTACT | TAAGTGTCGA | GCACAGAGCA | ATCTCAAACA | ATGTTGGATC | 2520 |
| AAGAATGTCA | ATCACGTGCT | TCTTCGGTGA | AAGTCCATAT | CAATCTTCCA | AGCTTTATGG | 2580 |
| ACCGATAACT | GAATTGTTAT | CAGAAGATAA | TCCTCCAAAA | TATCGCGCAA | CCACAGTGAA | 2640 |
| AGACCACACT | AGTTACCTCC | ATAACAGAGG | CCTAGATGGA | ACTTCTGCAT | TGTCCCGTTA | 2700 |
| CAAGATCTAA | GAATAAGAAT | AATAATGTTA | TCTATTATTA | CTATTTATAC | TTCTGCAGAT | 2760 |
| TGTACCTTTG | AATTTGAAGC | AAATGTTTGA | GTTAAATACT | TTCACGTTTC | TAAGCAATGT | 2820 |
| AATATAATTT | ATAAAGTATG | TGCTTGCTAT | ATATTGTTGT | TTAAAACATT | AAATAATATT | 2880 |
| ACATAAATAT | AAACACCATA | ATATAAGGAT | GTTTAGCATT | GTGGGAAAAT | GAAGGATTAA | 2940 |
| TAAGTCATAT | TAGTATTTCT | CTATGTCACA | TAAATGTGCC | TTCAACTCAA | TTTCCGCTGA | 3000 |
| TATTTATCTT | CTTTTATTTT | AAGTAGACGC | TTAAACTATT | GT | | 3042 |